(12) United States Patent
Miraglia et al.

(10) Patent No.: US 6,184,212 B1
(45) Date of Patent: Feb. 6, 2001

(54) ANTISENSE MODULATION OF HUMAN MDM2 EXPRESSION

(75) Inventors: Loren J. Miraglia, Encinitas; Pamela Nero, Oceanside; Mark J. Graham, San Clemente; Brett P. Monia, La Costa; Lex M. Cowsert, Carlsbad, all of CA (US)

(73) Assignee: Isis Pharmaceuticals Inc., Carlsbad, CA (US)

( * ) Notice: Under 35 U.S.C. 154(b), the term of this patent shall be extended for 0 days.

This patent is subject to a terminal disclaimer.

(21) Appl. No.: 09/280,805

(22) Filed: Mar. 26, 1999

Related U.S. Application Data

(63) Continuation-in-part of application No. 09/048,810, filed on Mar. 26, 1998.

(51) Int. Cl.[7] .......... C07H 21/04; A61K 48/00; C12Q 1/68; C12N 15/85; C12N 15/86
(52) U.S. Cl. .......... 514/44; 536/23.1; 536/24.3; 536/24.33; 536/24.5; 435/6; 435/91.1; 435/325; 435/375
(58) Field of Search .......... 514/44; 435/375, 435/325, 91.1, 6; 536/23.1, 24.5, 24.3

(56) References Cited

U.S. PATENT DOCUMENTS

| | | | |
|---|---|---|---|
| 5,652,355 | * | 7/1997 | Metelev et al. .......... 536/24.5 |
| 5,856,462 | * | 1/1999 | Agrawal .......... 536/24.5 |
| 6,013,786 | | 1/2000 | Chen et al. .......... 536/24.5 |

FOREIGN PATENT DOCUMENTS

| | | |
|---|---|---|
| 0 635 068 B1 | 11/1997 | (EP) . |
| WO 9320238 | * 10/1993 | (WO) . |
| WO 99/10486 | 3/1999 | (WO) . |

OTHER PUBLICATIONS

Andrea D. Branch, A good antisense molecule is hard to find, TIBS, 47–48, Feb. 1998.*
Trisha Gura, Antisense Has Growing Pains, Science, pp. 575–577, Oct. 1995.*
Stanley Crooke, Antisense '97: A roundtable on the state of the industry, Nature Biotechnology, p. 522, Jun. 1997.*
Stanley Crooke, Antisense Research and Applications, Chapter 1, Basic Principles of Antisense Therapeutics, Springer–Verlag Press, Berlin, Heidelberg, New York, p. 3, Jul. 1998.*
Kondo et al. MDM2 protein confers the resistance of a human gliobalstoma cell line to cisplatin–induced apoptosis, Oncogene, vol. 10, pp. 2001–2006, Apr. 1995.*

* cited by examiner

*Primary Examiner*—George C. Elliott
*Assistant Examiner*—Janet Epps
(74) *Attorney, Agent, or Firm*—Law Offices of Jane Massey Licata

(57) ABSTRACT

Compounds, compositions and methods are provided for inhibiting the expression of human mdm2. The compositions include antisense compounds targeted to nucleic acids encoding mdm2. Methods of using these oligonucleotides for inhibition of mdm2 expression and for treatment of diseases such as cancers associated with overexpression of mdm2 are provided.

20 Claims, No Drawings

ANTISENSE MODULATION OF HUMAN MDM2 EXPRESSION

This application is a continuation in-part of applicaton Ser. No. 09/048,810 filed Mar. 26, 1998.

FIELD OF THE INVENTION

This invention relates to compositions and methods for modulating expression of the human mdm2 gene, a naturally present cellular gene implicated in abnormal cell proliferation and tumor formation. This invention is also directed to methods for inhibiting hyperproliferation of cells; these methods can be used diagnostically or therapeutically. Furthermore, this invention is directed to treatment of conditions associated with expression of the human mdm2 gene.

BACKGROUND OF THE INVENTION

Inactivation of tumor suppressor genes leads to unregulated cell proliferation and is a cause of tumorigenesis. In many tumors, the tumor suppressors, p53 or Rb (retinoblastoma) are inactivated. This can occur either by mutations within these genes, or by overexpression of the mdm2 gene. The mdm2 protein physically associates with both p53 and Rb, inhibiting their function. The levels of mdm2 are maintained through a feedback loop mechanism with p53. Overexpression of mdm2 effectively inactivates p53 and promotes cell proliferation.

The role of p53 in apoptosis and tumorigenesis is well-known in the art (see, in general, Canman, C. E. and Kastan, M. B., *Adv. Pharmacol.*, 1997, 41, 429–460). Mdm2 has been shown to regulate p53's apoptotic functions (Chen, J., et al., *Mol. Cell Biol.*, 1996, 16, 2445–2452; Haupt, Y., et al., *EMBO J.*, 1996, 15, 1596–1606). Overexpression of mdm2 protects tumor cells from p53-mediated apoptosis. Thus, mdm2 is an attractive target for cancers associated with altered p53 expression.

Amplification of the mdm2 gene is found in many human cancers, including soft tissue sarcomas, astrocytomas, glioblastomas, breast cancers and non-small cell lung carcinomas. In many blood cancers, overexpression of mdm2 can occur with a normal copy number. This has been attributed to enhanced translation of mdm2 mRNA, which is thought to be related to a distinct 5'-untranslated region (5'-UTR) which causes the transcript to be translated more efficiently than the normal mdm2 transcript. Landers et al., *Cancer Res.* 57, 3562, (1997).

Several approaches have been used to disrupt the interaction between p53 and mdm2. Small peptide inhibitors, screened from a phage display library, have been shown in ELISA assays to disrupt this interaction [Bottger et al., *J. Mol. Biol.*, 269, 744 (1997)]. Microinjection of an anti-mdm2 antibody targeted to the p53-binding domain of mdm2 increased p53-dependent transcription [Blaydes et al., *Oncogene*, 14, 1859 (1997)].

A vector-based antisense approach has been used to study the function of mdm2. Using a rhabdomyosarcoma model, Fiddler et al. [*Mol. Cell Biol.*, 16, 5048 (1996)] demonstrated that amplified mdm2 inhibits the ability of MyoD to function as a transcription factor. Furthermore, expression of full-length antisense mdm2 from a cytomegalovirus promoter-containing vector restores muscle-specific gene expression.

Antisense oligonucleotides have also been useful in understanding the role of mdm2 in regulation of p53. An antisense oligonucleotide directed to the mdm2 start codon allowed cisplatin-induced p53-mediated apoptosis to occur in a cell line overexpressing mdm2 [Kondo et al., *Oncogene*, 10, 2001 (1995)]. The same oligonucleotide was found to inhibit the expression of P-glycoprotein [Kondo et al., *Br. J. Cancer*, 74, 1263 (1996)]. P-glycoprotein was shown to be induced by mdm2. Teoh et al [*Blood*, 90, 1982 (1997)] demonstrated that treatment with an identical mdm2 antisense oligonucleotide or a shorter version within the same region in a tumor cell line decreased DNA synthesis and cell viability and triggered apoptosis.

Chen et al. [*Proc. Natl. Acad. Sci. USA*, 95, 195 (1998); WO 99/10486] disclose antisense oligonucleotides targeted to the coding region of mdm2. A reduction in mdm2 RNA and protein levels was seen, and transcriptional activity from a p53-responsive promoter was increased after oligonucleotide treatment of JAR (choriocarcinoma) or SJSA (osteosarcoma) cells.

WO 93/20238 and WO 97/09343 disclose, in general, the use of antisense constructs, antisense oligonucleotides, ribozymes and triplex-forming oligonucleotides to detect or to inhibit expression of mdm2. EP 635068B1, issued Nov. 5, 1997, describes methods of treating in vitro neoplastic cells with an inhibitor of mdm2, and inhibitory compounds, including antisense oligonucleotides and triple-strand forming oligonucleotides.

There remains a long-felt need for improved compositions and methods for inhibiting mdm2 gene expression.

SUMMARY OF THE INVENTION

The present invention provides antisense compounds which are targeted to nucleic acids encoding human mdm2 and are capable of modulating, and preferably, inhibiting mdm2 expression. The present invention also provides chimeric compounds targeted to nucleic acids encoding human mdm2. The antisense compounds of the invention are believed to be useful both diagnostically and therapeutically, and are believed to be particularly useful in the methods of the present invention.

The present invention also comprises methods of inhibiting the expression of human mdm2, particularly the increased expression resulting from amplification of mdm2. These methods are believed to be useful both therapeutically and diagnostically as a consequence of the association between mdm2 expression and hyperproliferation. These methods are also useful as tools, for example, for detecting and determining the role of mdm2 expression in various cell functions and physiological processes and conditions and for diagnosing conditions associated with mdm2 expression.

The present invention also comprises methods of inhibiting hyperproliferation of cells using compounds of the invention. These methods are believed to be useful, for example, in diagnosing mdm2-associated cell hyperproliferation. Methods of treating abnormal proliferative conditions associated with mdm2 are also provided. These methods employ the antisense compounds of the invention. These methods are believed to be useful both therapeutically and as clinical research and diagnostic tools.

DETAILED DESCRIPTION OF THE INVENTION

Tumors often result from genetic changes in cellular regulatory genes. Among the most important of these are the tumor suppressor genes, of which p53 is the most widely studied. Approximately half of all human tumors have a mutation in the p53 gene. This mutation disrupts the ability of the p53 protein to bind to DNA and act as a transcription factor. Hyperproliferation of cells occurs as a result. Another mechanism by which p53 can be inactivated is through overexpression of mdm2, which regulates p53 activity in a feedback loop. The mdm2 protein binds to p53 in its DNA binding region, preventing its activity. Mdm2 is amplified in some human tumors, and this amplification is diagnostic of neoplasia or the potential therefor. Over one third of human sarcomas have elevated mdm2 sequences. Elevated expression may also be involved in other tumors including but not limited to those in which p53 inactivation has been implicated. These include colorectal carcinoma, lung cancer and chronic myelogenous leukemia.

Many abnormal proliferative conditions, particularly hyperproliferative conditions, are believed to be associated with increased mdm2 expression and are, therefore believed to be responsive to inhibition of mdm2 expression. Examples of these hyperproliferative conditions are cancers, psoriasis, blood vessel stenosis (e.g., restenosis or atherosclerosis), and fibrosis, e.g., of the lung or kidney. Increased levels of wild-type or mutated p53 have been found in some cancers (Nagashima, G., et al., Acta Neurochir. (Wein), 1999, 141, 53–61; Fiedler, A., et al., Langenbecks Arch. Surg., 1998, 383, 269–275). Increased levels of p53 is also associated with resistance of a cancer to a chemotherapeutic drug (Brown, R., et al., Int. J. Cancer, 1993, 55, 678–684). These diseases or conditions may be amenable to treatment by induction of mdm2 expression.

The present invention employs antisense compounds, particularly oligonucleotides, for use in modulating the function of nucleic acid molecules encoding mdm2, ultimately modulating the amount of mdm2 produced. This is accomplished by providing oligonucleotides which specifically hybridize with nucleic acids, preferably mRNA, encoding mdm2.

This relationship between an antisense compound such as an oligonucleotide and its complementary nucleic acid target, to which it hybridizes, is commonly referred to as "antisense". "Targeting" an oligonucleotide to a chosen nucleic acid target, in the context of this invention, is a multistep process. The process usually begins with identifying a nucleic acid sequence whose function is to be modulated. This may be, as examples, a cellular gene (or mRNA made from the gene) whose expression is associated with a particular disease state, or a foreign nucleic acid from an infectious agent. In the present invention, the target is a nucleic acid encoding mdm2; in other words, a mdm2 gene or RNA expressed from a mdm2 gene. mdm2 mRNA is presently the preferred target. The targeting process also includes determination of a site or sites within the nucleic acid sequence for the antisense interaction to occur such that modulation of gene expression will result.

In accordance with this invention, persons of ordinary skill in the art will understand that messenger RNA includes not only the information to encode a protein using the three letter genetic code, but also associated ribonucleotides which form a region known to such persons as the 5'-untranslated region, the 3'-untranslated region, the 5' cap region and intron/exon junction ribonucleotides. Thus, oligonucleotides may be formulated in accordance with this invention which are targeted wholly or in part to these associated ribonucleotides as well as to the informational ribonucleotides. The oligonucleotide may therefore be specifically hybridizable with a transcription initiation site region, a translation initiation codon region, a 5' cap region, an intron/exon junction, coding sequences, a translation termination codon region or sequences in the 5'- or 3'-untranslated region. Since, as is known in the art, the translation initiation codon is typically 5'-AUG (in transcribed mRNA molecules; 5'-ATG in the corresponding DNA molecule), the translation initiation codon is also referred to as the "AUG codon," the "start codon" or the "AUG start codon." A minority of genes have a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (prokaryotes). It is also known in the art that eukaryotic and prokaryotic genes may have two or more alternative start codons, any one of which may be preferentially utilized for translation initiation in a particular cell type or tissue, or under a particular set of conditions. In the context of the invention, "start codon" and "translation initiation codon" refer to the codon or codons that are used in vivo to initiate translation of an mRNA molecule transcribed from a gene encoding mdm2, regardless of the sequence(s) of such codons. It is also known in the art that a translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively). The terms "start codon region" and "translation initiation codon region" refer to a portion of such an mRNA or gene that encompasses from about 25 to about 50 contiguous nucleotides in either direction (i.e., 5' or 3') from a translation initiation codon. This region is a preferred target region. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon. This region is a preferred target region. The open reading frame (ORF) or "coding region," which is known in the art to refer to the region between the translation initiation codon and the translation termination codon, is also a region which may be targeted effectively. Other preferred target regions include the 5' untranslated region (5' UTR), known in the art to refer to the portion of an mRNA in the 5' direction from the translation initiation codon, and thus including nucleotides between the 5' cap site and the translation initiation codon of an mRNA or corresponding nucleotides on the gene) and the 3' untranslated region (3' UTR), known in the art to refer to the portion of an mRNA in the 3' direction from the translation termination codon, and thus including nucleotides between the translation termination codon and 3' end of an mRNA or corresponding nucleotides on the gene). mdm2 is believed to have alternative transcripts which differ in their 5'-UTR regions. The S-mdm2 transcript class is translated approximately 8-fold more efficiently than the L-mdm2 transcripts produced by the constitutive promoter. Landers et al., Cancer Res., 57, 3562 (1997). Accordingly, both the 5'-UTR of the S-mdm transcript and the 5'-UTR of the L-mdm2 transcript are preferred target regions, with the S-mdm2 5'-UTR being more preferred. mRNA splice sites may also be preferred target regions, and are particularly useful in situations where aberrant splicing is implicated in disease, or where an overproduction of a particular mRNA splice product is implicated in disease. Aberrant fusion junctions due to rearrangements or deletions may also be preferred targets.

Once the target site or sites have been identified, oligonucleotides are chosen which are sufficiently complementary to the target, i.e., hybridize sufficiently well and with sufficient specificity, to give the desired modulation.

"Hybridization", in the context of this invention, means hydrogen bonding, also known as Watson-Crick base pairing, between complementary bases, usually on opposite nucleic acid strands or two regions of a nucleic acid strand. Guanine and cytosine are examples of complementary bases which are known to form three hydrogen bonds between them. Adenine and thymine are examples of complementary bases which form two hydrogen bonds between them.

"Specifically hybridizable" and "complementary" are terms which are used to indicate a sufficient degree of complementarity such that stable and specific binding occurs between the DNA or RNA target and the oligonucleotide.

It is understood that an oligonucleotide need not be 100% complementary to its target nucleic acid sequence to be specifically hybridizable. An oligonucleotide is specifically hybridizable when binding of the oligonucleotide to the target interferes with the normal function of the target molecule to cause a loss of utility, and there is a sufficient degree of complementarity to avoid non-specific binding of the oligonucleotide to non-target sequences under conditions in which specific binding is desired, i.e., under physiological conditions in the case of in vivo assays or therapeutic treatment and, in the case of in vitro assays, under conditions in which the assays are conducted.

Hybridization of antisense oligonucleotides with mRNA interferes with one or more of the normal functions of mRNA. The functions of mRNA to be interfered with include all vital functions such as, for example, translocation of the RNA to the site of protein translation, translation of protein from the RNA, splicing of the RNA to yield one or more mRNA species, and catalytic activity which may be engaged in by the RNA.

The overall effect of interference with mRNA function is modulation of mdm2 expression. In the context of this invention "modulation" means either inhibition or stimulation; i.e., either a decrease or increase in expression. This modulation can be measured in ways which are routine in the art, for example by Northern blot assay of mRNA expression as taught in the examples of the instant application or by Western blot or ELISA assay of protein expression, or by an immunoprecipitation assay of protein expression, as taught in the examples of the instant application. Effects on cell proliferation or tumor cell growth can also be measured, as taught in the examples of the instant application.

The antisense compounds of this invention can be used in diagnostics, therapeutics, prophylaxis, and as research reagents and in kits. Since these compounds hybridize to nucleic acids encoding mdm2, sandwich, calorimetric and other assays can easily be constructed to exploit this fact. Furthermore, since the antisense compounds of this invention hybridize specifically to nucleic acids encoding particular isozymes of mdm2, such assays can be devised for screening of cells and tissues for particular mdm2 isozymes. Such assays can be utilized for diagnosis of diseases associated with various mdm2 forms. Provision of means for detecting hybridization of oligonucleotide with a mdm2 gene or mRNA can routinely be accomplished. Such provision may include enzyme conjugation, radiolabelling or any other suitable detection systems. Kits for detecting the presence or absence of mdm2 may also be prepared.

The present invention is also suitable for diagnosing abnormal proliferative states in tissue or other samples from patients suspected of having a hyperproliferative disease such as cancer or psoriasis. The ability of the oligonucleotides of the present invention to inhibit cell proliferation may be employed to diagnose such states. A number of assays may be formulated employing the present invention, which assays will commonly comprise contacting a tissue sample with an antisense compound of the invention under conditions selected to permit detection and, usually, quantitation of such inhibition. In the context of this invention, to "contact" tissues or cells with an antisense compound means to add the compound(s), usually in a liquid carrier, to a cell suspension or tissue sample, either in vitro or ex vivo, or to administer the antisense compound(s) to cells or tissues within an animal. Similarly, the present invention can be used to distinguish mdm2-associated tumors, particularly tumors associated with mdm2α, from tumors having other etiologies, in order that an efficacious treatment regime can be designed.

The antisense compounds of this invention may also be used for research purposes. Thus, the specific hybridization exhibited by oligonucleotides may be used for assays, purifications, cellular product preparations and in other methodologies which may be appreciated by persons of ordinary skill in the art.

In the context of this invention, the term "oligonucleotide" refers to an oligomer or polymer of ribonucleic acid or deoxyribonucleic acid. This term includes oligonucleotides composed of naturally-occurring nucleobases, sugars and covalent intersugar (backbone) linkages as well as oligonucleotides having non-naturally-occurring portions which function similarly. Such modified or substituted oligonucleotides are often preferred over native forms because of desirable properties such as, for example, enhanced cellular uptake, enhanced binding to target and increased stability in the presence of nucleases.

The antisense compounds in accordance with this invention preferably comprise from about 5 to about 50 nucleobases. Particularly preferred are antisense oligonucleotides comprising from about 8 to about 30 linked nucleobases (i.e. from about 8 to about 30 nucleosides). As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. In turn, the respective ends of this linear polymeric structure can be further joined to form a circular structure, however, open linear structures are generally preferred. Within the oligonucleotide structure, the phosphate groups are commonly referred to as forming the internucleoside backbone of the oligonucleotide. The normal linkage or backbone of RNA and DNA is a 3' to 5' phosphodiester linkage.

Specific examples of some preferred modified oligonucleotides envisioned for this invention include those containing phosphorothioates, phosphotriesters, methyl phosphonates, short chain alkyl or cycloalkyl intersugar linkages or short chain heteroatomic or heterocyclic intersugar linkages. Most preferred are oligonucleotides with phosphorothioates (usually abbreviated in the art as P=S) and those with $CH_2$—NH—O—$CH_2$, $CH_2$—N($CH_3$)—O—$CH_2$ [known as a methylene(methylimino) or MMI backbone], $CH_2$—O—N($CH_3$)—$CH_2$, $CH_2$—N($CH_3$)—N($CH_3$)—$CH_2$ and O—N($CH_3$)—$CH_2$—$CH_2$ backbones, wherein the native phosphodiester (usually abbreviated in the art as P=O) backbone is represented as O—P—O—CH$_2$). Also preferred are oligonucleotides having morpholino backbone structures (Summerton and Weller, U.S. Pat. No. 5,034,506). Further preferred are oligonucleotides with NR—C(*)—CH$_2$—CH$_2$, CH$_2$—NR—C(*)—CH$_2$, CH$_2$—CH$_2$—NR—C(*), C(*)—NR—CH$_2$—CH$_2$ and CH$_2$—C(*)—NR—CH$_2$ backbones, wherein "*" represents O or S (known as amide backbones; DeMesmaeker et al., WO 92/20823, published Nov. 26, 1992). In other preferred embodiments, such as the peptide nucleic acid (PNA) backbone, the phosphodiester backbone of the oligonucleotide is replaced with a polyamide backbone, the nucleobases being bound directly or indirectly to the aza nitrogen atoms of the polyamide backbone (Nielsen et al., Science, 254, 1497 (1991); U.S. Pat. No. 5,539,082). Other preferred modified oligonucleotides may contain one or more substituted sugar moieties comprising one of the following at the 2' position: OH, SH, SCH$_3$, F, OCN, OCH$_3$OCH$_3$, OCH$_3$O(CH$_2$)$_n$CH$_3$, O(CH$_2$)$_n$NH$_2$ or O(CH$_2$)$_n$CH$_3$ where n is from 1 to about 10; C$_1$ to C$_{10}$ lower alkyl, alkoxyalkoxy, substituted lower alkyl, alkaryl or aralkyl; Cl; Br; CN; CF$_3$; OCF$_3$; O—, S—, or N-alkyl; O—, S—, or N-alkenyl; SOCH$_3$; SO$_2$CH$_3$; ONO$_2$; NO$_2$; N$_3$; NH$_2$; heterocycloalkyl; heterocycloalkaryl; aminoalkylamino; polyalkylamino; substituted silyl; an RNA cleaving group; a reporter group; an intercalator; a group for improving the pharmacokinetic properties of an oligonucleotide; or a group for improving the pharmacodynamic properties of an oligonucleotide and other substituents having similar properties. A preferred modification includes 2'-O-methoxyethyl [which can be written as 2'-O—CH$_2$CH$_2$OCH$_3$, and is also known in the art as 2'-O-(2-methoxyethyl) or 2'-methoxyethoxy] [Martin et al., Helv. Chim. Acta, 78, 486 (1995)]. Other preferred modifications include 2'-methoxy (2'-O—CH$_3$), 2'-propoxy (2'-OCH$_2$CH$_2$CH$_3$), 2'-aminopropoxy (2'-OCH$_2$CH$_2$CH$_2$NH$_2$) and 2'-fluoro (2'-F). A further preferred modification includes 2'-dimethylaminooxyethoxy, i.e., a O(CH$_2$)$_2$ON(CH$_3$)$_2$ group, also known as 2'-DMAOE, as described in examples hereinbelow. Similar modifications may also be made at other positions on the oligonucleotide, particularly the 3' position of the sugar on the 3' terminal nucleotide and the 5' position of the 5' terminal nucleotide. Oligonucleotides may also have sugar mimetics such as cyclobutyls in place of the pentofuranosyl group.

The oligonucleotides of the invention may additionally or alternatively include nucleobase modifications or substitutions. As used herein, "unmodified" or "natural" nucleobases include adenine (A), guanine (G), thymine (T), cytosine (C) and uracil (U). Modified nucleobases include nucleobases found only infrequently or transiently in natural nucleic acids, e.g., hypoxanthine, 6-methyladenine and 5-methylcytosine, as well as synthetic nucleobases, e.g., 5-bromouracil, 5-hydroxymethyluracil, 8-azaguanine, 7-deazaguanine, N$^6$(6-aminohexyl)adenine and 2,6-diaminopurine [Kornberg, A., DNA Replication, 1974, W.H. Freeman & Co., San Francisco, 1974, pp. 75–77; Gebeyhu, G., et al., Nucleic Acids Res., 15, 4513 (1987)]. 5-methylcytosine (5-me-C) is presently a preferred nucleobase, particularly in combination with 2'-O-methoxyethyl modifications.

Another preferred additional or alternative modification of the oligonucleotides of the invention involves chemically linking to the oligonucleotide one or more lipophilic moieties which enhance the cellular uptake of the oligonucleotide. Such lipophilic moieties may be linked to an oligonucleotide at several different positions on the oligonucleotide. Some preferred positions include the 3' position of the sugar of the 3' terminal nucleotide, the 5' position of the sugar of the 5' terminal nucleotide, and the 2' position of the sugar of any nucleotide. The N$^6$ position of a purine nucleobase may also be utilized to link a lipophilic moiety to an oligonucleotide of the invention (Gebeyehu, G., et al., Nucleic Acids Res., 1987, 15, 4513). Such lipophilic moieties include but are not limited to a cholesteryl moiety [Letsinger et al., Proc. Natl. Acad. Sci. USA., 86, 6553 (1989)], cholic acid [Manoharan et al., Bioorg. Med. Chem. Let., 4, 1053 (1994)], a thioether, e.g., hexyl-S-tritylthiol [Manoharan et al., Ann. N.Y. Acad. Sci., 660, 306 (1992); Manoharan et al., Bioorg. Med. Chem. Let., 3, 2765 (1993)], a thiocholesterol [Oberhauser et al., Nucl. Acids Res., 20, 533 (1992)], an aliphatic chain, e.g., dodecandiol or undecyl residues [Saison-Behmoaras et al., EMBO J., 10, 111 (1991); Kabanov et al., FEBS Lett., 259, 327 (1990); Svinarchuk et al., Biochimie., 75, 49(1993)], a phospholipid, e.g., di-hexadecyl-rac-glycerol or triethylammonium 1,2-di-O-hexadecyl-rac-glycero-3-H-phosphonate [Manoharan et al., Tetrahedron Lett., 36, 3651 (1995); Shea et al., Nucl. Acids Res., 18, 3777 (1990)], a polyamine or a polyethylene glycol chain [Manoharan et al., Nucleosides & Nucleotides, 14, 969 (1995)], or adamantane acetic acid [Manoharan et al., Tetrahedron Lett., 36, 3651 (1995)], a palmityl moiety [Mishra et al., Biochim. Biophys. Acta, 1264, 229 (1995)], or an octadecylamine or hexylamino-carbonyl-oxycholesterol moiety [Crooke et al., J. Pharmacol. Exp. Ther., 277, 923 (1996)]. Oligonucleotides comprising lipophilic moieties, and methods for preparing such oligonucleotides, as disclosed in U.S. Pat. Nos. 5,138,045, 5,218,105 and 5,459,255, the contents of which are hereby incorporated by reference.

The present invention also includes oligonucleotides which are chimeric oligonucleotides. "Chimeric" oligonucleotides or "chimeras," in the context of this invention, are oligonucleotides which contain two or more chemically distinct regions, each made up of at least one nucleotide. These oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of antisense inhibition of gene expression. Cleavage of the RNA target can be routinely detected by gel electrophoresis and, if necessary, associated nucleic acid hybridization techniques known in the art. This RNAse H-mediated cleavage of the RNA target is distinct from the use of ribozymes to cleave nucleic acids. Ribozymes are not comprehended by the present invention.

Examples of chimeric oligonucleotides include but are not limited to "gapmers," in which three distinct regions are present, normally with a central region flanked by two regions which are chemically equivalent to each other but distinct from the gap. A preferred example of a gapmer is an oligonucleotide in which a central portion (the "gap") of the oligonucleotide serves as a substrate for RNase H and is preferably composed of 2'-deoxynucleotides, while the flanking portions (the 5' and 3' "wings") are modified to have greater affinity for the target RNA molecule but are unable to support nuclease activity (e.g., 2'-fluoro- or 2'-O-methoxyethyl-substituted). Other chimeras include "wingmers," also known in the art as "hemimers," that is, oligonucleotides with two distinct regions. In a preferred example of a wingmer, the 5' portion of the oligonucleotide serves as a substrate for RNase H and is preferably composed of 2'-deoxynucleotides, whereas the 3' portion is modified in such a fashion so as to have greater affinity for the target RNA molecule but is unable to support nuclease activity (e.g., 2'-fluoro- or 2'-O-methoxyethyl-substituted), or vice-versa. In one embodiment, the oligonucleotides of the present invention contain a 2'-O-methoxyethyl (2'-O—CH$_2$CH$_2$OCH$_3$) modification on the sugar moiety of at least one nucleotide. This modification has been shown to increase both affinity of the oligonucleotide for its target and nuclease resistance of the oligonucleotide. According to the invention, one, a plurality, or all of the nucleotide subunits of the oligonucleotides of the invention may bear a 2'-O-methoxyethyl (—O—CH$_2$CH$_2$OCH$_3$) modification. Oligonucleotides comprising a plurality of nucleotide subunits having a 2'-O-methoxyethyl modification can have such a modification on any of the nucleotide subunits within the oligonucleotide, and may be chimeric oligonucleotides. Aside from or in addition to 2'-O-methoxyethyl modifications, oligonucleotides containing other modifications which enhance antisense efficacy, potency or target affinity are also preferred. Chimeric oligonucleotides comprising one or more such modifications are presently preferred. Through use of such modifications, active oligonucleotides have been identified which are shorter than conventional "first generation" oligonucleotides active against mdm2. Oligonucleotides in accordance with this invention are from 5 to 50 nucleotides in length, preferably from about 8 to about 30. In the context of this invention it is understood that this encompasses non-naturally occurring oligomers as hereinbefore described, having from 5 to 50 monomers, preferably from about 8 to about 30.

The oligonucleotides used in accordance with this invention may be conveniently and routinely made through the well-known technique of solid phase synthesis. Equipment for such synthesis is sold by several vendors including Applied Biosystems. Any other means for such synthesis may also be employed; the actual synthesis of the oligonucleotides is well within the talents of the routineer. It is well known to use similar techniques to prepare oligonucleotides such as the phosphorothioates and 2'-alkoxy or 2'-alkoxyalkoxy derivatives, including 2'-O-methoxyethyl oligonucleotides [Martin, P., *Helv. Chim. Acta*, 78, 486 (1995)]. It is also well known to use similar techniques and commercially available modified amidites and controlled-pore glass (CPG) products such as biotin, fluorescein, acridine or psoralen-modified amidites and/or CPG (available from Glen Research, Sterling Va.) to synthesize fluorescently labeled, biotinylated or other conjugated oligonucleotides.

The antisense compounds of the present invention include bioequivalent compounds, including pharmaceutically acceptable salts and prodrugs. This is intended to encompass any pharmaceutically acceptable salts, esters, or salts of such esters, or any other compound which, upon administration to an animal including a human, is capable of providing (directly or indirectly) the biologically active metabolite or residue thereof. Accordingly, for example, the disclosure is also drawn to pharmaceutically acceptable salts of the nucleic acids of the invention and prodrugs of such nucleic acids.

Pharmaceutically acceptable "salts" are physiologically and pharmaceutically acceptable salts of the nucleic acids of the invention: i.e., salts that retain the desired biological activity of the parent compound and do not impart undesired toxicological effects thereto [see, for example, Berge et al., "Pharmaceutical Salts," *J. of Pharma Sci.*, 66:1 (1977)].

For oligonucleotides, examples of pharmaceutically acceptable salts include but are not limited to (a) salts formed with cations such as sodium, potassium, ammonium, magnesium, calcium, polyamines such as spermine and spermidine, etc.; (b) acid addition salts formed with inorganic acids, for example hydrochloric acid, hydrobromic acid, sulfuric acid, phosphoric acid, nitric acid and the like; © salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (d) salts formed from elemental anions such as chlorine, bromine, and iodine.

The oligonucleotides of the invention may additionally or alternatively be prepared to be delivered in a "prodrug" form. The term "prodrug" indicates a therapeutic agent that is prepared in an inactive form that is converted to an active form (i.e., drug) within the body or cells thereof by the action of endogenous enzymes or other chemicals and/or conditions. In particular, prodrug versions of the oligonucleotides of the invention are prepared as SATE [(S-acetyl-2-thioethyl) phosphate] derivatives according to the methods disclosed in WO 93/24510 to Gosselin et al., published Dec. 9, 1993.

For therapeutic or prophylactic treatment, oligonucleotides are administered in accordance with this invention. Oligonucleotide compounds of the invention may be formulated in a pharmaceutical composition, which may include pharmaceutically acceptable carriers, thickeners, diluents, buffers, preservatives, surface active agents, neutral or cationic lipids, lipid complexes, liposomes, penetration enhancers, carrier compounds and other pharmaceutically acceptable carriers or excipients and the like in addition to the oligonucleotide. Such compositions and formulations are comprehended by the present invention.

Pharmaceutical compositions comprising the oligonucleotides of the present invention may include penetration enhancers in order to enhance the alimentary delivery of the oligonucleotides. Penetration enhancers may be classified as belonging to one of five broad categories, i.e., fatty acids, bile salts, chelating agents, surfactants and non-surfactants (Lee et al., *Critical Reviews in Therapeutic Drug Carrier Systems*, 1991, 8:91–192; Muranishi, *Critical Reviews in Therapeutic Drug Carrier Systems*, 1990, 7:1). One or more penetration enhancers from one or more of these broad categories may be included. Compositions comprising oligonucleotides and penetration enhancers are disclosed in co-pending U.S. patent application Ser. No. 08/886,829 to Teng et al., filed Jul. 1, 1997, which is herein incorporated by reference in its entirety.

The compositions of the present invention may additionally contain other adjunct components conventionally found in pharmaceutical compositions, at their art-established usage levels. Thus, for example, the compositions may contain additional compatible pharmaceutically-active materials such as, e.g., antipruritics, astringents, local anesthetics or anti-inflammatory agents, or may contain additional materials useful in physically formulating various dosage forms of the composition of present invention, such as dyes, flavoring agents, preservatives, antioxidants, opacifiers, thickening agents and stabilizers. However, such materials, when added, should not unduly interfere with the biological activities of the components of the compositions of the invention.

Regardless of the method by which the oligonucleotides of the invention are introduced into a patient, colloidal dispersion systems may be used as delivery vehicles to enhance the in vivo stability of the oligonucleotides and/or to target the oligonucleotides to a particular organ, tissue or cell type. Colloidal dispersion systems include, but are not limited to, macromolecule complexes, nanocapsules, microspheres, beads and lipid-based systems including oil-in-water emulsions, micelles, mixed micelles, liposomes and lipid:oligonucleotide complexes of uncharacterized structure. A preferred colloidal dispersion system is a plurality of liposomes. Liposomes are microscopic spheres having an aqueous core surrounded by one or more outer layers made up of lipids arranged in a bilayer configuration [see, generally, Chonn et al., *Current Op. Biotech.*, 6, 698 (1995)]. Liposomal antisense compositions are prepared according to the disclosure of co-pending U.S. patent application Ser. No. 08/961,469 to Hardee et al., filed Oct. 31, 1997, herein incorporated by reference in its entirety.

The pharmaceutical compositions of the present invention may be administered in a number of ways depending upon whether local or systemic treatment is desired and upon the area to be treated. Administration may be topical (including ophthalmic, vaginal, rectal, intranasal, epidermal and transdermal), oral or parenteral. Parenteral administration includes intravenous drip, subcutaneous, intraperitoneal or intramuscular injection, pulmonary administration, e.g., by inhalation or insufflation, or intracranial, e.g., intrathecal or intraventricular, administration. Oligonucleotides with at least one 2'-O-methoxyethyl modification are believed to be particularly useful for oral administration. Modes of administering oligonucleotides are disclosed in co-pending U.S. patent application Ser. No. 08/961,469 to Hardee et al., filed Oct. 31, 1997, herein incorporated by reference in its entirety.

Formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

Compositions for oral administration include powders or granules, suspensions or solutions in water or non-aqueous media, capsules, sachets or tablets. Thickeners, flavoring agents, diluents, emulsifiers, dispersing aids or binders may be desirable.

Compositions for parenteral administration may include sterile aqueous solutions which may also contain buffers, diluents and other suitable additives. In some cases it may be more effective to treat a patient with an oligonucleotide of the invention in conjunction with other traditional therapeutic modalities in order to increase the efficacy of a treatment regimen. In the context of the invention, the term "treatment regimen" is meant to encompass therapeutic, palliative and prophylactic modalities. For example, a patient may be treated with conventional chemotherapeutic agents, particularly those used for tumor and cancer treatment. Examples of such chemotherapeutic agents include but are not limited to daunorubicin, daunomycin, dactinomycin, doxorubicin, epirubicin, idarubicin, esorubicin, bleomycin, mafosfamide, ifosfamide, cytosine arabinoside, bis-chloroethylnitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine (CA), 5-azacytidine, hydroxyurea, deoxycoformycin, 4-hydroxyperoxycyclophosphoramide, 5-fluorouracil (5-FU), 5-fluorodeoxyuridine (5-FUdR), methotrexate (MTX), colchicine,taxol,vincristine,vinblastine,etoposide, trimetrexate, teniposide, cisplatin and diethylstilbestrol (DES). See, generally, *The Merck Manual of Diagnosis and Therapy*, 15th Ed., pp. 1206–1228, Berkow et al., eds., Rahay, N.J., 1987). When used with the compounds of the invention, such chemotherapeutic agents may be used individually (e.g., 5-FU and oligonucleotide), sequentially (e.g., 5-FU and oligonucleotide for a period of time followed by MTX and oligonucleotide), or in combination with one or more other such chemotherapeutic agents (e.g., 5-FU, MTX and oligonucleotide, or 5-FU, radiotherapy and oligonucleotide).

The formulation of therapeutic compositions and their subsequent administration is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on $EC_{50}$s found to be effective in in vitro and in vivo animal models. In general, dosage is from 0.01 µg to 100 g per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 µg to 100 g per kg of body weight, once or more daily, to once every 20 years.

Thus, in the context of this invention, by "therapeutically effective amount" is meant the amount of the compound which is required to have a therapeutic effect on the treated mammal. This amount, which will be apparent to the skilled artisan, will depend upon the type of mammal, the age and weight of the mammal, the type of disease to be treated, perhaps even the gender of the mammal, and other factors which are routinely taken into consideration when treating a mammal with a disease. A therapeutic effect is assessed in the mammal by measuring the effect of the compound on the disease state in the animal. For example, if the disease to be treated is cancer, therapeutic effects are assessed by measuring the rate of growth or the size of the tumor, or by measuring the production of compounds such as cytokines, production of which is an indication of the progress or regression of the tumor.

The following examples illustrate the present invention and are not intended to limit the same.

EXAMPLES

Example 1

Synthesis of Oligonucleotides

Unmodified oligodeoxynucleotides are synthesized on an automated DNA synthesizer (Applied Biosystems model 380B) using standard phosphoramidite chemistry with oxidation by iodine. β-cyanoethyldiisopropyl-phosphoramidites are purchased from Applied Biosystems (Foster City, Calif.). For phosphorothioate oligonucleotides, the standard oxidation bottle was replaced by a 0.2 M solution of $^3$H-1,2-benzodithiole-3-one 1,1-dioxide in acetonitrile for the stepwise thiation of the phosphite linkages. The thiation cycle wait step was increased to 68 seconds and was followed by the capping step.

2'-methoxy oligonucleotides are synthesized using 2'-methoxy β-cyanoethyldiisopropyl-phosphoramidites (Chemgenes, Needham, Mass.) and the standard cycle for unmodified oligonucleotides, except the wait step after pulse delivery of tetrazole and base was increased to 360 seconds. Other 2'-alkoxy oligonucleotides were synthesized by a modification of this method, using appropriate 2'-modified amidites such as those available from Glen Research, Inc., Sterling, Va.

2'-fluoro oligonucleotides were synthesized as described in Kawasaki et al., *J. Med. Chem.*, 36, 831 (1993). Briefly, the protected nucleoside $N^6$-benzoyl-2'-deoxy-2'-fluoroadenosine was synthesized utilizing commercially available 9-β-D-arabinofuranosyladenine as starting material and by modifying literature procedures whereby the 2'-α-fluoro atom is introduced by a $S_N2$-displacement of a 2'-β-O-trifyl group. Thus $N^6$-benzoyl-9-β-D-arabinofuranosyladenine was selectively protected in moderate yield as the 3',5'-ditetrahydropyranyl (THP) intermediate. Deprotection of the THP and $N^6$-benzoyl groups was accomplished using standard methodologies and standard methods were used to obtain the 5'-dimethoxytrityl-(DMT) and 5'-DMT-3'-phosphoramidite intermediates.

The synthesis of 2'-deoxy-2'-fluoroguanosine was accomplished using tetraisopropyldisiloxanyl (TPDS) protected 9-β-D-arabinofuranosylguanine as starting material, and conversion to the intermediate diisobutyryl-arabinofuranosylguanosine. Deprotection of the TPDS group was followed by protection of the hydroxyl group with THP to give diisobutyryl di-THP protected arabinofuranosylguanine. Selective O-deacylation and triflation was followed by treatment of the crude product with fluoride, then deprotection of the THP groups. Standard methodologies were used to obtain the 5'-DMT- and 5'-DMT-3'-phosphoramidites.

Synthesis of 2'-deoxy-2'-fluorouridine was accomplished by the modification of a known procedure in which 2,2'-anhydro-1-β-D-arabinofuranosyluracil was treated with 70% hydrogen fluoride-pyridine. Standard procedures were used to obtain the 5'-DMT and 5'-DMT-3' phosphoramidites.

2'-deoxy-2'-fluorocytidine was synthesized via amination of 2'-deoxy-2'-fluorouridine, followed by selective protection to give $N^4$-benzoyl-2'-deoxy-2'-fluorocytidine. Standard procedures were used to obtain the 5'-DMT and 5'-DMT-3' phosphoramidites.

2'-(2-methoxyethyl)-modified amidites are synthesized according to Martin, P., *Helv. Chim. Acta*, 78,486 (1995). For ease of synthesis, the last nucleotide was a deoxynucleotide. 2'-O—$CH_2CH_2OCH_3$-cytosines may be 5-methyl cytosines.

Synthesis of 5-Methyl Cytosine Monomers 2,2'-Anhydro[1-(β-D-arabinofuranosyl)-5-methyluridine]:

5-Methyluridine (ribosylthymine, commercially available through Yamasa, Choshi, Japan) (72.0 g, 0.279 M), diphenylcarbonate (90.0 g, 0.420 M) and sodium bicarbonate (2.0 g, 0.024 M) were added to DMF (300 mL). The mixture was heated to reflux, with stirring, allowing the evolved carbon dioxide gas to be released in a controlled manner. After 1 hour, the slightly darkened solution was concentrated under reduced pressure. The resulting syrup was poured into diethylether (2.5 L), with stirring. The product formed a gum. The ether was decanted and the residue was dissolved in a minimum amount of methanol (ca. 400 mL). The solution was poured into fresh ether (2.5 L) to yield a stiff gum. The ether was decanted and the gum was dried in a vacuum oven (60° C. at 1 mm Hg for 24 hours) to give a solid which was crushed to a light tan powder (57 g, 85% crude yield). The material was used as is for further reactions.

2'-O-Methoxyethyl-5-methyluridine:

2,2'-Anhydro-5-methyluridine (195 g, 0.81 M), tris(2-methoxyethyl)borate (231 g, 0.98 M) and 2-methoxyethanol (1.2 L) were added to a 2 L stainless steel pressure vessel and placed in a pre-heated oil bath at 160° C. After heating for 48 hours at 155–160° C., the vessel was opened and the solution evaporated to dryness and triturated with MeOH (200 mL). The residue was suspended in hot acetone (1 L). The insoluble salts were filtered, washed with acetone (150 mL) and the filtrate evaporated. The residue (280 g) was dissolved in $CH_3CN$ (600 mL) and evaporated. A silica gel column (3 kg) was packed in $CH_2Cl_2$/acetone/MeOH (20:5:3) containing 0.5% $Et_3NH$. The residue was dissolved in $CH_2Cl_2$ (250 mL) and adsorbed onto silica (150 g) prior to loading onto the column. The product was eluted with the packing solvent to give 160 g (63%) of product.

2'-O-Methoxyethyl-5'-O-dimethoxytrityl-5-methyluridine:

2'-O-Methoxyethyl-5-methyluridine (160 g, 0.506 M) was co-evaporated with pyridine (250 mL) and the dried residue dissolved in pyridine (1.3 L). A first aliquot of dimethoxytrityl chloride (94.3 g, 0.278 M) was added and the mixture stirred at room temperature for one hour. A second aliquot of dimethoxytrityl chloride (94.3 g, 0.278 M) was added and the reaction stirred for an additional one hour. Methanol (170 mL) was then added to stop the reaction. HPLC showed the presence of approximately 70% product. The solvent was evaporated and triturated with $CH_3CN$ (200 mL). The residue was dissolved in $CHCl_3$ (1.5 L) and extracted with 2×500 mL of saturated $NaHCO_3$ and 2×500 mL of saturated NaCl. The organic phase was dried over $Na_2SO_4$, filtered and evaporated. 275 g of residue was obtained. The residue was purified on a 3.5 kg silica gel column, packed and eluted with EtOAc/Hexane/Acetone (5:5:1) containing 0.5% $Et_3NH$. The pure fractions were evaporated to give 164 g of product. Approximately 20 g additional was obtained from the impure fractions to give a total yield of 183 g (57%).

3'-O-Acetyl-2'-O-methoxyethyl-5'-O-dimethoxytrityl-5-methyluridine:

2'-O-Methoxyethyl-5'-O-dimethoxytrityl-5-methyluridine (106 g, 0.167 M), DMF/pyridine (750 mL of a 3:1 mixture prepared from 562 mL of DMF and 188 mL of pyridine) and acetic anhydride (24.38 mL, 0.258 M) were combined and stirred at room temperature for 24 hours. The reaction was monitored by tlc by first quenching the tlc sample with the addition of MeOH. Upon completion of the reaction, as judged by tlc, MeOH (50 mL) was added and the mixture evaporated at 35° C. The residue was dissolved in $CHCl_3$ (800 mL) and extracted with 2×200 mL of saturated sodium bicarbonate and 2×200 mL of saturated NaCl. The water layers were back extracted with 200 mL of $CHCl_3$. The combined organics were dried with sodium sulfate and evaporated to give 122 g of residue (approx. 90% product). The residue was purified on a 3.5 kg silica gel column and eluted using EtOAc/Hexane(4:1). Pure product fractions were evaporated to yield 96 g (84%).

3'-O-Acetyl-2'-O-methoxyethyl-5'-O-dimethoxytrityl-5-methyl-4-triazoleuridine:

A first solution was prepared by dissolving 3'-O-acetyl-2'-O-methoxyethyl-5'-O-dimethoxytrityl-5-methyluridine (96 g, 0.144 M) in $CH_3CN$ (700 mL) and set aside. Triethylamine (189 mL, 1.44 M) was added to a solution of triazole (90 g, 1.3 M) in $CH_3CN$ (1 L), cooled to −5° C. and stirred for 0.5 h using an overhead stirrer. $POCl_3$ was added dropwise, over a 30 minute period, to the stirred solution maintained at 0–10° C., and the resulting mixture stirred for an additional 2 hours. The first solution was added dropwise, over a 45 minute period, to the later solution. The resulting reaction mixture was stored overnight in a cold room. Salts were filtered from the reaction mixture and the solution was evaporated. The residue was dissolved in EtOAc (1 L) and the insoluble solids were removed by filtration. The filtrate was washed with 1×300 mL of $NaHCO_3$ and 2×300 mL of saturated NaCl, dried over sodium sulfate and evaporated. The residue was triturated with EtOAc to give the title compound.

2'-O-Methoxyethyl-5'-O-dimethoxytrityl-5-methylcytidine:

A solution of 3'-O-acetyl-2'-O-methoxyethyl-5'-O-dimethoxytrityl-5-methyl-4-triazoleuridine (103 g, 0.141 M) in dioxane (500 mL) and $NH_4OH$ (30 mL) was stirred at room temperature for 2 hours. The dioxane solution was evaporated and the residue azeotroped with MeOH (2×200 mL). The residue was dissolved in MeOH (300 mL) and transferred to a 2 liter stainless steel pressure vessel. MeOH (400 mL) saturated with $NH_3$ gas was added and the vessel heated to 100° C. for 2 hours (tlc showed complete conversion). The vessel contents were evaporated to dryness and the residue was dissolved in EtOAc (500 mL) and washed once with saturated NaCl (200 mL). The organics were dried over sodium sulfate and the solvent was evaporated to give 85 g (95%) of the title compound.

$N^4$-N-Benzoyl-2'-O-methoxyethyl-5'-O-dimethoxytrityl-5-methylcytidine:

2'-O-Methoxyethyl-5'-O-dimethoxytrityl-5-methylcytidine (85 g, 0.134 M) was dissolved in DMF (800 mL) and benzoic anhydride (37.2 g, 0.165 M) was added with stirring. After stirring for 3 hours, tlc showed the reaction to be approximately 95% complete. The solvent was evaporated and the residue azeotroped with MeOH (200 mL). The residue was dissolved in $CHCl_3$ (700 mL) and extracted with saturated $NaHCO_3$ (2×300 mL) and saturated NaCl (2×300 mL), dried over $MgSO_4$ and evaporated to give a residue (96 g). The residue was chromatographed on a 1.5 kg silica column using EtOAc/Hexane (1:1) containing 0.5% $Et_3NH$ as the eluting solvent. The pure product fractions were evaporated to give 90 g (90%) of the title compound.

$N^4$-Benzoyl-2'-O-methoxyethyl-5'-O-dimethoxytrityl-5-methylcytidine-3'-amidite:

$N^4$-Benzoyl-2'-O-methoxyethyl-5'-O-dimethoxytrityl-5-methylcytidine (74 g, 0.10 M) was dissolved in $CH_2Cl_2$ (1 L). Tetrazole diisopropylamine (7.1 g) and 2-cyanoethoxytetra(isopropyl)phosphite (40.5 mL, 0.123 M) were added with stirring, under a nitrogen atmosphere. The resulting mixture was stirred for 20 hours at room temperature (tlc showed the reaction to be 95% complete). The reaction mixture was extracted with saturated $NaHCO_3$ (1×300 mL) and saturated NaCl (3×300 mL). The aqueous washes were back-extracted with $CH_2Cl_2$ (300 mL), and the extracts were combined, dried over $MgSO_4$ and concentrated. The residue obtained was chromatographed on a 1.5 kg silica column using EtOAcHexane (3:1) as the eluting solvent. The pure fractions were combined to give 90.6 g (87%) of the title compound.

5-methyl-2'-deoxycytidine (5-me-C) containing oligonucleotides were synthesized according to published methods [Sanghvi et al., *Nucl. Acids Res.*, 21, 3197 (1993)] using commercially available phosphoramidites (Glen Research, Sterling Va. or ChemGenes, Needham Mass.).

2'-O-(dimethylaminooxyethyl) nucleoside amidites

2'-(Dimethylaminooxyethoxy) nucleoside amidites [also known in the art as 2'-O-(dimethylaminooxyethyl) nucleoside amidites] are prepared as described in the following paragraphs. Adenosine, cytidine and guanosine nucleoside amidites are prepared similarly to the thymidine (5-methyluridine) except the exocyclic amines are protected with a benzoyl moiety in the case of adenosine and cytidine and with isobutyryl in the case of guanosine.

5'-O-tert-Butyldiphenylsilyl-$O^2$-2'-anhydro-5-methyluridine $O^2$-2'-anhydro-5-methyluridine (Pro. Bio. Sint., Varese, Italy, 100.0 g, 0.416 mmol), dimethylaminopyridine (0.66 g, 0.013 eq, 0.0054 mmol) were dissolved in dry pyridine (500 ml) at ambient temperature under an argon atmosphere and with mechanical stirring. tert-Butyldiphenylchlorosilane (125.8 g, 119.0 mL, 1.1 eq, 0.458 mmol) was added in one portion. The reaction was stirred for 16 h at ambient temperature. TLC (Rf 0.22, ethyl acetate) indicated a complete reaction. The solution was concentrated under reduced pressure to a thick oil. This was partitioned between dichloromethane (1 L) and saturated sodium bicarbonate (2×1 L) and brine (1 L). The organic layer was dried over sodium sulfate and concentrated under reduced pressure to a thick oil. The oil was dissolved in a 1:1 mixture of ethyl acetate and ethyl ether (600 mL) and the solution was cooled to −10° C. The resulting crystalline product was collected by filtration, washed with ethyl ether (3×200 mL) and dried (40° C., 1 mm Hg, 24 h) to 149 g (74.8%) of white solid. TLC and NMR were consistent with pure product.

5'-O-tert-Butyldiphenylsilyl-2'-O-(2-hydroxyethyl)-5-methyluridine

In a 2 L stainless steel, unstirred pressure reactor was added borane in tetrahydrofuran (1.0 M, 2.0 eq, 622 mL). In the fume hood and with manual stirring, ethylene glycol (350 mL, excess) was added cautiously at first until the evolution of hydrogen gas subsided. 5'-O-tert-Butyldiphenylsilyl-$O^2$-2'-anhydro-5-methyluridine (149 g, 0.311 mol) and sodium bicarbonate (0.074 g, 0.003 eq) were added with manual stirring. The reactor was sealed and heated in an oil bath until an internal temperature of 160° C. was reached and then maintained for 16 h (pressure<100 psig). The reaction vessel was cooled to ambient and opened. TLC (Rf 0.67 for desired product and Rf 0.82 for ara-T side product, ethyl acetate) indicated about 70% conversion to the product. In order to avoid additional side product formation, the reaction was stopped, concentrated under reduced pressure (10 to 1 mm Hg) in a warm water bath (40–100° C.) with the more extreme conditions used to remove the ethylene glycol. [Alternatively, once the low boiling solvent is gone, the remaining solution can be partitioned between ethyl acetate and water. The product will be in the organic phase.] The residue was purified by column chromatography (2 kg silica gel, ethyl acetate-hexanes gradient 1:1 to 4:1). The appropriate fractions were combined, stripped and dried to product as a white crisp foam (84 g, 50%), contaminated starting material (17.4 g) and pure reusable starting material 20 g. The yield based on starting material less pure recovered starting material was 58%. TLC and NMR were consistent with 99% pure product.

2'-O-([2-phthalimidoxy)ethyl]-5'-t-butyldiphenylsilyl-5-methyluridine

5'-O-tert-Butyldiphenylsilyl-2'-O-(2-hydroxyethyl)-5-methyluridine (20 g, 36.98 mmol) was mixed with triphenylphosphine (11.63 g, 44.36 mmol) and N-hydroxyphthalimide (7.24 g, 44.36 mmol). It was then dried over $P_2O_5$ under high vacuum for two days at 40° C. The reaction mixture was flushed with argon and dry THF (369.8 mL, Aldrich, sure seal bottle) was added to get a clear solution. Diethylazodicarboxylate (6.98 mL, 44.36 mmol) was added dropwise to the reaction mixture. The rate of addition is maintained such that resulting deep red coloration is just discharged before adding the next drop. After the addition was complete, the reaction was stirred for 4 hrs. By that time TLC showed the completion of the reaction (ethylacetate:hexane, 60:40). The solvent was evaporated in vacuum. Residue obtained was placed on a flash column and eluted with ethyl acetate:hexane (60:40), to get 2'-O-([2-phthalimidoxy)ethyl]-5'-t-butyldiphenylsilyl-5-methyluridine as white foam (21.819, 86%).

5'-O-tert-butyldiphenylsilyl-2'-O-[(2-formadoximinooxy)ethyl]-5-methyluridine 2'-O-([2-phthalimidoxy)ethyl]-5'-t-butyldiphenylsilyl-5-methyluridine (3.1 g, 4.5 mmol) was dissolved in dry $CH_2Cl_2$ (4.5 mL) and methylhydrazine (300 mL, 4.64 mmol) was added dropwise at –10° C. to 0° C. After 1 hr the mixture was filtered, the filtrate was washed with ice cold $CH_2Cl_2$ and the combined organic phase was washed with water, brine and dried over anhydrous $Na_2SO_4$. The solution was concentrated to get 2'-O-(aminooxyethyl) thymidine, which was then dissolved in MeOH (67.5 mL). To this formaldehyde (20% aqueous solution, w/w, 1.1 eg.) was added and the mixture for 1 hr. Solvent was removed under vacuum; residue chromatographed to get 5'-O-tert-butyldiphenylsilyl-2'-O-[(2-formadoximinooxy)ethyl]-5-methyluridine as white foam (1.95, 78%).

5'-O-tert-Butyldiphenylsilyl-2'-O-[N,N-dimethylaminooxyethyl]-5-methyluridine 5'-O-tert-butyldiphenylsilyl-2'-O-[(2-formadoximinooxy)ethyl]-5-methyluridine (1.77 g, 3.12 mmol) was dissolved in a solution of 1M pyridinium p-toluenesulfonate (PPTS) in dry MeOH (30.6 mL). Sodium cyanoborohydride (0.39 g, 6.13 mmol) was added to this solution at 10° C. under inert atmosphere. The reaction mixture was stirred for 10 minutes at 10° C. After that the reaction vessel was removed from the ice bath and stirred at room temperature for 2 hr, the reaction monitored by TLC (5% MeOH in $CH_2Cl_2$). Aqueous $NaHCO_3$ solution (5%, 10 mL) was added and extracted with ethyl acetate (2×20 mL). Ethyl acetate phase was dried over anhydrous $Na_2SO_4$, evaporated to dryness. Residue was dissolved in a solution of 1M PPTS in MeOH (30.6 mL). Formaldehyde (20% w/w, 30 mL, 3.37 mmol) was added and the reaction mixture was stirred at room temperature for 10 minutes. Reaction mixture cooled to 10° C. in an ice bath, sodium cyanoborohydride (0.39 g, 6.13 mmol) was added and reaction mixture stirred at 10° C. for 10 minutes. After 10 minutes, the reaction mixture was removed from the ice bath and stirred at room temperature for 2 hrs. To the reaction mixture 5% $NaHCO_3$ (25 mL) solution was added and extracted with ethyl acetate (2×25 mL). Ethyl acetate layer was dried over anhydrous $Na_2SO_4$ and evaporated to dryness. The residue obtained was purified by flash column chromatography and eluted with 5% MeOH in $CH_2Cl_2$ to get 5'-O-tert-butyldiphenylsilyl-2'-O-[N,N-dimethylaminooxyethyl]-5-methyluridine as a white foam (14.6 g, 80%).

2'-O-(dimethylaminooxyethyl)-5-methyluridine

Triethylamine trihydrofluoride (3.91 mL, 24.0 mmol) was dissolved in dry THF and triethylamine (1.67 mL, 12 mmol, dry, kept over KOH). This mixture of triethylamine-2HF was then added to 5'-O-tert-butyldiphenylsilyl-2'-O-[N,N-dimethylaminooxyethyl]-5-methyluridine (1.40 g, 2.4 mmol) and stirred at room temperature for 24 hrs. Reaction was monitored by TLC (5% MeOH in $CH_2Cl_2$). Solvent was removed under vacuum and the residue placed on a flash column and eluted with 10% MeOH in $CH_2Cl_2$ to get 2'-O-(dimethylaminooxyethyl)-5-methyluridine (766 mg, 92.5%).

5'-O-DMT-2'-O-(dimethylaminooxyethyl)-5-methyluridine

2'-O-(dimethylaminooxyethyl)-5-methyluridine (750 mg, 2.17 mmol) was dried over $P_2O_5$ under high vacuum overnight at 40° C. It was then co-evaporated with anhydrous pyridine (20 mL). The residue obtained was dissolved in pyridine (11 mL) under argon atmosphere. 4-dimethylaminopyridine (26.5 mg, 2.60 mmol), 4,4'-dimethoxytrityl chloride (880 mg, 2.60 mmol) was added to the mixture and the reaction mixture was stirred at room temperature until all of the starting material disappeared. Pyridine was removed under vacuum and the residue chromatographed and eluted with 10% MeOH in $CH_2Cl_2$ (containing a few drops of pyridine) to get 5'-O-DMT-2'-O-(dimethylamino-oxyethyl)-5-methyluridine (1.13 g, 80%).

5'-O-DMT-2'-O-(2-N,N-dimethylaminooxyethyl)-5-methyluridine-3'-[(2-cyanoethyl)-N,N-diisopropylphosphoramidite]

5'-O-DMT-2'-O-(dimethylaminooxyethyl)-5-methyluridine (1.08 g, 1.67 mmol) was co-evaporated with toluene (20 mL). To the residue N,N-diisopropylamine tetrazonide (0.29 g, 1.67 mmol) was added and dried over $P_2O_5$ under high vacuum overnight at 40° C. Then the reaction mixture was dissolved in anhydrous acetonitrile (8.4 mL) and 2-cyanoethyl-N,N,$N^1$,$N^1$-tetraisopropylphosphoramidite (2.12 mL, 6.08 mmol) was added. The reaction mixture was stirred at ambient temperature for 4 hrs under inert atmosphere. The progress of the reaction was monitored by TLC (hexane:ethyl acetate 1:1). The solvent was evaporated, then the residue was dissolved in ethyl acetate (70 mL) and washed with 5% aqueous $NaHCO_3$ (40 mL) Ethyl acetate layer was dried over anhydrous $Na_2SO_4$ and concentrated. Residue obtained was chromatographed (ethyl acetate as eluent) to get 5'-O-DMT-2'-O-(2-N,N-dimethylaminooxyethyl)-5-methyluridine-3'-[(2-cyanoethyl)-N,N-diisopropylphosphoramidite] as a foam (1.04 g, 74.9%).

2'-(Aminooxyethoxy) nucleoside amidites

2'-(Aminooxyethoxy) nucleoside amidites [also known in the art as 2'-O-(aminooxyethyl) nucleoside amidites] are prepared as described in the following paragraphs. Adenosine, cytidine and thymidine nucleoside amidites are prepared similarly.

N2-isobutyryl-6-O-diphenylcarbamoyl-2'-O-(2-ethylacetyl)-5'-O-(4,4'-dimethoxytrityl)guanosine-3'-[(2-cyanoethyl)-N,N-diisopropylphosphoramidite]

The 2'-O-aminooxyethyl guanosine analog may be obtained by selective 2'-O-alkylation of diaminopurine riboside. Multigram quantities of diaminopurine riboside may be purchased from Schering AG (Berlin) to provide 2'-O-(2-ethylacetyl) diaminopurine riboside along with a minor amount of the 3'-O-isomer. 2'-O-(2-ethylacetyl) diaminopurine riboside may be resolved and converted to 2'-O-(2-ethylacetyl)guanosine by treatment with adenosine deaminase. (McGee, D. P. C., Cook, P. D., Guinosso, C. J., WO 94/02501 A1 940203.) Standard protection procedures should afford 2'-O-(2-ethylacetyl )-5'-O-(4,4'-dimethoxytrityl)guanosine and 2-N-isobutyryl-6-O-diphenylcarbamoyl-2'-O-(2-ethylacetyl)-5'-O-(4,4'-dimethoxy trityl)guanosine which may be reduced to provide 2-N-isobutyryl-6-O-diphenylcarbamoyl-2'-O-(2-ethylacetyl)-5'-O-(4,4'-dimethoxytrityl) guanosine. As before the hydroxyl group may be displaced by N-hydroxyphthalimide via a Mitsunobu reaction, and the protected nucleoside may phosphitylated as usual to yield 2-N-isobutyryl-6-O-diphenylcarbamoyl-2'-O-(2-ethylacetyl)-5'-O-(4,4'-dimethoxytrityl)guanosine-3'-[(2-cyanoethyl)-N,N-diisopropylphosphoramidite].

Oligonucleotides having methylene (methylimino) (MMI) backbones are synthesized according to U.S. Pat. No. 5,378,825, which is coassigned to the assignee of the present invention and is incorporated herein in its entirety. For ease of synthesis, various nucleoside dimers containing MMI linkages were synthesized and incorporated into oligonucleotides. Other nitrogen-containing backbones are synthesized according to WO 92/20823 which is also coassigned to the assignee of the present invention and incorporated herein in its entirety.

Oligonucleotides having amide backbones are synthesized according to De Mesmaeker et al., Acc. Chem. Res., 28, 366 (1995). The amide moiety is readily accessible by simple and well-known synthetic methods and is compatible with the conditions required for solid phase synthesis of oligonucleotides.

Oligonucleotides with morpholino backbones are synthesized according to U.S. Pat. No. 5,034,506 (Summerton and Weller).

Peptide-nucleic acid (PNA) oligomers are synthesized according to P. E. Nielsen et al., Science, 254, 1497 (1991).

After cleavage from the controlled pore glass column (Applied Biosystems) and deblocking in concentrated ammonium hydroxide at 55° C. for 18 hours, the oligonucleotides are purified by precipitation twice out of 0.5 M NaCl with 2.5 volumes ethanol. Synthesized oligonucleotides were analyzed by polyacrylamide gel electrophoresis on denaturing gels and judged to be at least 85% full length material. The relative amounts of phosphorothioate and phosphodiester linkages obtained in synthesis were periodically checked by $^{31}$p nuclear magnetic resonance spectroscopy, and for some studies oligonucleotides were purified by HPLC, as described by Chiang et al., J. Biol. Chem., 266, 18162 (1991). Results obtained with HPLC-purified material were similar to those obtained with non-HPLC purified material.

Example 2

Human mdm2 Oligonucleotide Sequences

The oligonucleotides tested are presented in Table 1. Sequence data are from the cDNA sequence published by Oliner, J. D., et al., Nature, 358, 80 (1992); Genbank accession number Z12020, provided herein as SEQ ID NO: 1. Oligonucleotides were synthesized primarily as chimeric oligonucleotides having a centered deoxy gap of eight nucleotides flanked by 2'-O-methoxyethyl regions.

A549 human lung carcinoma cells (American Type Culture Collection, Manassas, Va.) were routinely passaged at 80–90% confluency in Dulbecco's modified Eagle's medium (DMEM) and 10% fetal bovine serum (Hyclone, Logan, Utah). JEG-3 cells, a human choriocarcinoma cell line (American Type Culture Collection, Manassas, Va.), were maintained in RPMI1640, supplemented with 10% fetal calf serum. All cell culture reagents, except as otherwise indicated, are obtained from Life Technologies (Rockville, Md.).

549 cells were treated with phosphorothioate oligonucleotides at 200 nM for four hours in the presence of 6 µg/ml LIPOFECTINT™, washed and allowed to recover for an additional 20 hours. Total RNA was extracted and 15–20 µg of each was resolved on 1% gels and transferred to nylon membranes. The blots were probed with a $^{32}$p radiolabeled mdm2 cDNA probe and then stripped and reprobed with a radiolabeled G3PDH probe to confirm equal RNA loading. mdm2 transcripts were examined and quantified with a PhosphorImager (Molecular Dynamics, Sunnyvale, Calif.). Results are shown in Table 2. Oligonucleotides 16506 (SEQ ID NO: 3), 16507 (SEQ ID NO: 4), 16508 (SEQ ID NO: 5), 16510 (SEQ ID NO: 7), 16518 (SEQ ID NO: 15), 165020 (SEQ ID NO: 17), 16521 (SEQ ID NO: 18), 16522 (SEQ ID NO: 19) and 16524 (SEQ ID NO: 21) gave at least approximately 50% reduction of mdm2 mRNA levels. Oligonucleotides 16507 and 16518 gave better than 85% reduction of mdm2.

TABLE 1

Nucleotide Sequences of Human mdm2 Phosphorothioate Oligonucleotides

| ISIS NO. | NUCLEOTIDE SEQUENCE[1] (5' → 3') | SEQ ID NO: | TARGET GENE NUCLEOTIDE CO-ORDINATES[2] | GENE TARGET REGION |
|---|---|---|---|---|
| 16506 | CAGCCAAGCTCGCGCGGTGC | 3 | 0001–0020 | 5'-UTR |
| 16507 | TCTTTCCGACACACAGGGCC | 4 | 0037–0056 | 5'-UTR |
| 16508 | CAGCAGGATCTCGGTCAGAG | 5 | 0095–0114 | 5'-UTR |
| 16509 | GGGCGCTCGTACGCACTAAT | 6 | 0147–0166 | 5'-UTR |
| 16510 | TCGGGGATCATTCCACTCTC | 7 | 0181–0200 | 5'-UTR |
| 16511 | CGGGGTTTTCGCGCTTGGAG | 8 | 0273–0292 | 5'-UTR |
| 16512 | CATTTGCCTGCTCCTCACCA | 9 | 0295–0314 | AUG |
| 16513 | GTATTGCACATTTGCCTGCT | 10 | 0303–0322 | AUG |
| 16514 | AGCACCATCAGTAGGTACAG | 11 | 0331–0350 | ORF |
| 16515 | CTACCAAGTTCCTGTAGATC | 12 | 0617–0636 | ORF |
| 16516 | TCAACTTCAAATTCTACACT | 13 | 1047–1066 | ORF |
| 16517 | TTTACAATCAGGAACATCAA | 14 | 1381–1400 | ORF |
| 16518 | AGCTTCTTTGCACATGTAAA | 15 | 1695–1714 | ORF |
| 16519 | CAGGTCAACTAGGGGAAATA | 16 | 1776–1795 | stop |
| 16520 | TCTTATAGACAGGTCAACTA | 17 | 1785–1804 | stop |
| 16521 | TCCTAGGGTTATATAGTTAG | 18 | 1818–1837 | 3'-UTR |

TABLE 1-continued

Nucleotide Sequences of Human mdm2 Phosphorothioate Oligonucleotides

| ISIS NO. | NUCLEOTIDE SEQUENCE[1] (5' → 3') | SEQ ID NO: | TARGET GENE NUCLEOTIDE CO-ORDINATES[2] | GENE TARGET REGION |
|---|---|---|---|---|
| 16522 | AAGTATTCACTATTCCACTA | 19 | 1934–1953 | 3'-UTR |
| 16523 | CCAAGATCACCCACTGCACT | 20 | 2132–2151 | 3'-UTR |
| 16524 | AGGTGTGGTGGCAGATGACT | 21 | 2224–2243 | 3'-UTR |
| 16525 | CCTGTCTCTACTAAAAGTAC | 22 | 2256–2275 | 3'-UTR |
| 17604 | ACAAGCCTTCGCTCTACCGG | 23 | scrambled control | 16507 |
| 17605 | TTCAGCGCATTTGTACATAA | 24 | scrambled control | 16518 |
| 17615 | TCTTTCCGACACACAGGGCC | 25 | 0037–0056 | 5'-UTR |
| 17616 | AGCTTCTTTGCACATGTAAA | 15 | 1695–1714 | ORF |
| 17755 | AGCTTCTTTGCACATGTAAA | 15 | 1695–1714 | ORF |
| 17756 | AGCTTCTTTATACATGTAAA | 26 | 2-base mismatch | 17616 |
| 17757 | AGCTTCTTTACACATGTAAA | 27 | 1-base mismatch | 17616 |

[1]Emboldened residues, 2'-methoxyethoxy- residues (others are 2'-deoxy-) including "C" residues, 5-methyl-cytosines; all linkages are phosphorothioate linkages.
[2]Co-ordinates from Genbank Accession No. Z12020, locus name "HSP53ASSG", SEQ ID NO: 1. Oligonucleotides 16505–16511 are targeted to the 5' UTR of the L-mdm2 transcript as described hereinabove [Landers et al., Cancer Res., 57, 3562 (1997)] Nucleotide coordinates on the Landers sequence [Landers et al., Cancer Res., 57, 3562 (1997) and Genbank accession no. U39736] are identical to those shown in Table 1 except for ISIS 16511, which maps to nucleotides 267–286 on the Landers sequence.

TABLE 2

Activities of Phosphorothioate Oligonucleotides Targeted to Human mdm2

| ISIS No: | SEQ ID NO: | GENE TARGET REGION | % mRNA EXPRESSION | % mRNA INHIBITION |
|---|---|---|---|---|
| LIPOFECTIN ™ only | — | — | 100% | 0% |
| 16506 | 3 | 5'-UTR | 45% | 55% |
| 16507 | 4 | 5'-UTR | 13% | 87% |
| 16508 | 5 | 5'-UTR | 38% | 62% |
| 16509 | 6 | 5'-UTR | 161% | — |
| 16510 | 7 | 5'-UTR | 46% | 54% |
| 16511 | 8 | 5'-UTR | 91% | 9% |
| 16512 | 9 | AUG | 89% | 11% |
| 16513 | 10 | AUG | 174% | — |
| 16514 | 11 | Coding | 92% | 8% |
| 16515 | 12 | Coding | 155% | — |
| 16516 | 13 | Coding | 144% | — |
| 16517 | 14 | Coding | 94% | 6% |
| 16518 | 15 | Coding | 8% | 92% |
| 16519 | 16 | stop | 73% | 27% |
| 16520 | 17 | stop | 51% | 49% |
| 16521 | 18 | 3'-UTR | 38% | 62% |
| 16522 | 19 | 3'-UTR | 49% | 51% |
| 16523 | 20 | 3'-UTR | 109% | — |
| 16524 | 21 | 3'-UTR | 47% | 53% |
| 16525 | 22 | 3'-UTR | 100% | — |

Example 3

Dose Response of Antisense Oligonucleotide Effects on Human mdm2 mRNA Levels in A549 Cells Oligonucleotides 16507 and 16518 were tested at different concentrations. A549 cells were grown, treated and processed as described in Example 2. LIPOFECTIN™ was added at a ratio of 3 μg/ml per 100 nM of oligonucleotide. The control included LIPOFECTIN™ at a concentration of 12 μg/ml. Oligonucleotide 17605, an oligonucleotide with different sequence but identical base composition to oligonucleotide 16518, was used as a negative control. Results are shown in Table 3. Oligonucleotides 16507 and 16518 gave approximately 90% inhibition at concentrations greater than 200 nM. No inhibition was seen with oligonucleotide 17605.

TABLE 3

Dose Response of A549 Cells to mdm2 Antisense Oligonucleotides (ASOs)

| ISIS # | SEQ ID NO: | ASO Gene Target | Dose | % mRNA Expression | % mRNA Inhibition |
|---|---|---|---|---|---|
| control | — | LIPOFECTIN ™ only | — | 100% | 0% |
| 16507 | 4 | 5'-UTR | 25 nM | 55% | 45% |
| 16507 | 4 | " | 50 nM | 52% | 48% |
| 16507 | 4 | " | 100 nM | 24% | 76% |
| 16507 | 4 | " | 200 nM | 12% | 88% |
| 16518 | 15 | Coding | 50 nM | 18% | 82% |
| 16518 | 15 | " | 100 nM | 14% | 86% |
| 16518 | 15 | " | 200 nM | 9% | 91% |
| 16518 | 15 | " | 400 nM | 8% | 92% |
| 17605 | 24 | scrambled | 400 nM | 129% | — |

Example 4

Time Course of Antisense Oligonucleotide Effects mdm2 mRNA Levels in A549 Cells Oligonucleotides 16507 and 17605 were tested by treating for varying times. A549 cells were grown, treated for times indicated in Table 4 and processed as described in Example 2. Results are shown in Table 4. Oligonucleotide 16507 gave greater than 90% inhibition throughout the time course. No inhibition was seen with oligonucleotide 17605.

TABLE 4

Time Course of Response of Cells to
Human mdm2 Antisense Oligonucleotides (ASOs)

| ISIS # | SEQ ID NO: | ASO Gene Target Region | Time | % RNA Expression | % RNA Inhibition |
|---|---|---|---|---|---|
| basal | — | LIPOFECTIN ™ only | 24 h | 100% | 0% |
| basal | — | LIPOFECTIN ™ only | 48 h | 100% | 0% |
| basal | — | LIPOFECTIN ™ only | 72 h | 100% | 0% |
| 16518 | 15 | Coding | 24 h | 3% | 97% |
| 16518 | 15 | " | 48 h | 6% | 94% |
| 16518 | 15 | " | 72 h | 5% | 95% |
| 17605 | 24 | scrambled | 24 h | 195% | — |
| 17605 | 24 | " | 48 h | 100% | — |
| 17605 | 24 | " | 72 h | 102% | — |

Example 5

Effect of Antisense Oligonucleotides on Cell Proliferation in A549 Cells 49 cells were treated on day 0 for four hours with 400 nM oligonucleotide and 12 mg/ml LIPOFECTIN. After four hours, the medium was replaced. Twenty-four, forty-eight or seventy-two hours after initiation of oligonucleotide treatment, live cells were counted on a hemacytometer. Results are shown in Table 5.

TABLE 5

Antisense Inhibition of Cell Proliferation in A549 cells

| ISIS # | SEQ ID NO: | ASO Gene Target Region | Time | % Cell Growth | % Growth Inhibition |
|---|---|---|---|---|---|
| basal | — | LIPOFECTIN ™ only | 24 h | 100% | 0% |
| basal | — | LIPOFECTIN ™ only | 48 h | 100% | 0% |
| basal | — | LIPOFECTIN ™ only | 72 h | 100% | 0% |
| 16518 | 15 | Coding | 24 h | 53% | 47% |
| 16518 | 15 | " | 48 h | 27% | 73% |
| 16518 | 15 | " | 72 h | 17% | 83% |
| 17605 | 24 | scrambled | 24 h | 93% | 7% |
| 17605 | 24 | " | 48 h | 76% | 24% |
| 17605 | 24 | " | 72 h | 95% | 5% |

Example 6

Effect of mdm2 Antisense Oligonucleotide on p53 Protein Levels

JEG3 cells were cultured and treated as described in Example 2, except that 300 nM oligonucleotide and 9 µg/ml of LIPOFECTIN™ was used.

For determination of p53 protein levels by western blot, cellular extracts were prepared using 300 µl of RIPA extraction buffer per 100-mm dish. The protein concentration was quantified by Bradford assay using the BioRad kit (BioRad, Hercules, Calif.). Equal amounts of protein were loaded on 10% or 12% SDS-PAGE mini-gel (Novex, San Diego, Calif.). Once transferred to PVDF membranes (Millipore, Bedford, Mass.), the membranes were then treated for a minimum of 2 h with specific primary antibody (p53 antibody, Transduction Laboratories, Lexington, Ky.) followed by incubation with secondary antibody conjugated to HRP. The results were visualized by ECL Plus Western Blotting Detection System (Amersham Pharmacia Biotech, Piscataway, N.J.). In some experiments, the blots were stripped in stripping buffer (2% SDS, 12.5 mM Tris, pH 6.8) for 30 min. at 50° C. After extensive washing, the blots were blocked and blotted with different primary antibody.

Results are shown in Table 6. Treatment with mdm2 antisense oligonucleotide results in the induction of p53 levels. An approximately three-fold increase in activity was seen under these conditions.

TABLE 6

Activity of ISIS 16518 on p53 Protein Levels

| ISIS No: | SEQ ID NO: | GENE TARGET REGION | % protein EXPRESSION |
|---|---|---|---|
| LIPOFECTIN ™ only | — | — | 100% |
| 16518 | 15 | coding | 289% |

Example 7

Effect of ISIS 16518 on Expression of p53 Mediated Genes p53 is known to regulate the expression of a number of genes and to be involved in apoptosis. Representative genes known to be regulated by p53 include p21 (Deng, C., et al., Cell, 1995, 82, 675), bax (Selvakumaran, M., et al., Oncogene, 1994, 9, 1791–1798) and GADD45 (Carrier, F., et al., J. Biol. Chem., 1994, 269, 32672–32677). The effect of an mdm2 antisense oligonucleotide on these genes is investigated by RPA analysis using the RIBOQUANT™ RPA kit, according to the manufacturer's instructions (Pharmingen, San Diego, Calif.), along with the hSTRESS-1 multi-probe template set. Included in this template set are bclx, p53, GADD45, c-fos, p21, bax, bcl2 and mcl1. The effect of mdm2 antisense oligonucleotides on p53-mediated apoptosis can readily be assessed using commercial kits based on apoptotic markers such as DNA fragmentation or caspase activity.

Example 8

Additional Human mdm2 Chimeric (deoxy gapped) Antisense Oligonucleotides

Additional oligonucleotides targeted to the 5'-untranslated region of human mdm2 MRNA were designed and synthesized. Sequence data are from the cDNA sequence published by Zauberman, A., et al., Nucleic Acids Res., 23, 2584 (1995); Genbank accession number HSU28935. Oligonucleotides were synthesized primarily as chimeric oligonucleotides having a centered deoxy gap of eight nucleotides flanked by 2'-O-methoxyethyl regions. The oligonucleotide sequences are shown in Table 7. These oligonucleotides were tested in A549 cells as described in Example 2. Results are shown in Table 8.

TABLE 7

Nucleotide Sequences of additional Human mdm2 Chimeric (deoxy gapped) Phosphorothioate Oligonucleotides

| ISIS NO. | NUCLEOTIDE SEQUENCE[1] (5' → 3') | SEQ ID NO: | TARGET GENE NUCLEOTIDE CO-ORDINATES[2] | GENE TARGET REGION |
|---|---|---|---|---|
| 21926 | CTACCCTCCAATCGCCACTG | 28 | 0238–0257 | coding |
| 21927 | GGTCTACCCTCCAATCGCCA | 29 | 0241–0260 | coding |
| 21928 | CGTGCCCACAGGTCTACCCT | 30 | 0251–0270 | coding |
| 21929 | AAGTGGCGTGCGTCCGTGCC | 31 | 0265–0284 | coding |
| 21930 | AAAGTGGCGTGCGTCCGTGC | 32 | 0266–0285 | coding |

[1]Emboldened residues, 2'-methoxyethoxy- residues (others are 2'-deoxy-); all 2'-methoxyethoxy-cytosine and 2'-deoxy-cytosine residues, 5-methyl-cytosines; all linkages are phosphorothioate linkages.
[2]Co-ordinates from Genbank Accession No. U28935, locus name "HSU28935", SEQ ID NO: 2.

TABLE 8

Activities of Chimeric (deoxy gapped) Oligonucleotides Targeted to Human mdm2

| ISIS No: | SEQ ID NO: | GENE TARGET REGION | % mRNA EXPRESSION | % mRNA INHIBITION |
|---|---|---|---|---|
| LIPOFECTIN ™ only | — | — | 100% | 0% |
| 21926 | 28 | coding | 345% | — |
| 21927 | 29 | coding | 500% | — |
| 21928 | 30 | coding | 417% | — |
| 21929 | 31 | coding | 61% | 39% |
| 21930 | 32 | coding | 69% | 31% |

These oligonucleotide sequences were also tested for their ability to reduce mdm2 protein levels. JEG3 cells were cultured and treated as described in Example 2, except that 300 nM oligonucleotide and 9 µg/ml of LIPOFECTIN™ was used. Mdm2 protein levels were assayed by Western blotting as described in Example 6, except an mouse anti-mdm2 monoclonal antibody (Santa Cruz Biotechnology, Santa Cruz, Calif.) was used. Results are shown in Table 9.

TABLE 9

Activities of Chimeric (deoxy gapped) Human mdm2 Antisense Oligonucleotides on mdm2 Protein Levels

| ISIS No: | SEQ ID NO: | GENE TARGET REGION | % PROTEIN EXPRESSION | % PROTEIN INHIBITION |
|---|---|---|---|---|
| LIPOFECTIN ™ only | — | — | 100% | 0% |
| 21926 | 28 | coding | 30% | 70% |
| 21927 | 29 | coding | 18% | 82% |
| 21928 | 30 | coding | 43% | 57% |
| 21929 | 31 | coding | 62% | 33% |
| 21930 | 32 | coding | 56% | 44% |

Each oligonucleotide tested reduced mdm2 protein levels by greater than approximately 40%. Maximum inhibition was seen with oligonucleotide 21927 (SEQ ID NO. 29) which gave greater than 80% inhibition of mdm2 protein.

Example 9

Additional Human mdm2 Antisense Oligonucleotides

Additional oligonucleotides targeted to human mdm2 mRNA were designed and synthesized. Sequence data are from the cDNA sequence published by Zauberman, A., et al., *Nucleic Acids Res.*, 23, 2584 (1995); Genbank accession number HSU28935. Oligonucleotides were synthesized in 96 well plate format via solid phase P(III) phosphoramidite chemistry on an automated synthesizer capable of assembling 96 sequences simultaneously in a standard 96 well format. Phosphodiester internucleotide linkages were afforded by oxidation with aqueous iodine. Phosphorothioate internucleotide linkages were generated by sulfurization utilizing 3,H-1,2 benzodithiole-3-one 1,1 dioxide (Beaucage Reagent) in anhydrous acetonitrile. Standard base-protected beta-cyanoethyl-di-isopropyl phosphoramidites were purchased from commercial vendors (e.g. PE-Applied Biosystems, Foster City, Calif., or Pharmacia, Piscataway, N.J.). Non-standard nucleosides are synthesized as per published methods. They are utilized as base protected beta-cyanoethyldiisopropyl phosphoramidites.

Oligonucleotides were cleaved from support and deprotected with concentrated $NH_4OH$ at elevated temperature (55–60° C.) for 12–16 hours and the released product then dried in vacuo. The dried product was then re-suspended in sterile water to afford a master plate from which all analytical and test plate samples are then diluted utilizing robotic pipettors.

Two sets of oligonucleotides were synthesized; one as phosphorothioate oligodeoxynucleotides, the other as chimeric oligonucleotides having a centered deoxy gap of ten nucleotides flanked by regions of five 2'-O-methoxyethyl nucleotides. These oligonucleotides sequences are shown in Tables 10 and 11.

mRNA was isolated using the RNAEASY® kit (Qiagen, Santa Clarita, Calif.).

TABLE 10

Nucleotide Sequences of Human mdm2
Phosphorothioate Oligodeoxynucleotides

| ISIS NO. | NUCLEOTIDE SEQUENCE[1] (5' -> 3') | SEQ ID NO: | TARGET GENE NUCLEOTIDE CO-ORDINATES[2] | GENE TARGET REGION |
| --- | --- | --- | --- | --- |
| 31712 | AAGCAGCCAAGCTCGCGCGG | 33 | 0004–0023 | 5' UTR |
| 31552 | CAGGCCCCAGAAGCAGCCAA | 34 | 0014–0033 | 5' UTR |
| 31713 | GCCACACAGGCCCCAGAAGC | 35 | 0020–0039 | 5' UTR |
| 31394 | ACACACAGGGCCACACAGGC | 36 | 0029–0048 | 5' UTR |
| 31714 | TTCCGACACACAGGGCCACA | 37 | 0034–0053 | 5' UTR |
| 31553 | GCTCCATCTTTCCGACACAC | 38 | 0043–0062 | 5' UTR |
| 31715 | GCTTCTTGCTCCATCTTTCC | 39 | 0050–0069 | 5' UTR |
| 31395 | CCCTCGGGCTCGGCTTCTTG | 40 | 0062–0081 | 5' UTR |
| 31716 | GCGGCCGCCCCTCGGGCTCG | 41 | 0070–0089 | 5' UTR |
| 31554 | AAGCAGCAGGATCTCGGTCA | 42 | 0098–0107 | 5' UTR |
| 31717 | GCTGCGAAAGCAGCAGGATC | 43 | 0105–0124 | 5' UTR |
| 31396 | TGCTCCTGGCTGCGAAAGCA | 44 | 0113–0132 | 5' UTR |
| 31718 | GGGACGGTGCTCCTGGCTGC | 45 | 0120–0139 | 5' UTR |
| 31555 | ACTGGGCGCTCGTACGCACT | 46 | 0150–0169 | 5' UTR |
| 31719 | GCCAGGGCACTGGGCGCTCG | 47 | 0158–0177 | 5' UTR |
| 31397 | TCTCCGGGCCAGGGCACTGG | 48 | 0165–0184 | 5' UTR |
| 31720 | TCATTCCACTCTCCGGGCCA | 49 | 0174–0193 | 5' UTR |
| 31556 | GGAAGCACGACGCCCTGGGC | 50 | 0202–0221 | 5' UTR |
| 31721 | TACTGCGGAAGCACGACGCC | 51 | 0208–0227 | 5' UTR |
| 31398 | GGGACTGACTACTGCGGAAG | 52 | 0217–0236 | 5' UTR |
| 31722 | TCAAGACTCCCCAGTTTCCT | 53 | 0242–0261 | 5' UTR |
| 31557 | CCTGCTCCTCACCATCCGGG | 54 | 0289–0308 | 5' UTR |
| 31399 | TTTGCCTGCTCCTCACCATC | 55 | 0293–0312 | AUG |
| 31400 | ATTTGCCTGCTCCTCACCAT | 56 | 0294–0313 | AUG |
| 31401 | CATTTGCCTGCTCCTCACCA | 9 | 0295–0314 | AUG |
| 31402 | ACATTTGCCTGCTCCTCACC | 57 | 0296–0315 | AUG |
| 31403 | CACATTTGCCTGCTCCTCAC | 58 | 0297–0316 | AUG |
| 31404 | GCACATTTGCCTGCTCCTCA | 59 | 0298–0317 | AUG |
| 31405 | TGCACATTTGCCTGCTCCTC | 60 | 0299–0318 | AUG |
| 31406 | TTGCACATTTGCCTGCTCCT | 61 | 0300–0319 | AUG |
| 31407 | ATTGCACATTTGCCTGCTCC | 62 | 0301–0320 | AUG |
| 31408 | TATTGCACATTTGCCTGCTC | 63 | 0302–0321 | AUG |
| 31409 | GTATTGCACATTTGCCTGCT | 10 | 0303–0322 | AUG |
| 31410 | GGTATTGCACATTTGCCTGC | 64 | 0304–0323 | AUG |
| 31411 | TGGTATTGCACATTTGCCTG | 65 | 0305–0324 | AUG |
| 31412 | TTGGTATTGCACATTTGCCT | 66 | 0306–0325 | AUG |
| 31413 | GTTGGTATTGCACATTTGCC | 67 | 0307–0326 | AUG |
| 31414 | TGTTGGTATTGCACATTTGC | 68 | 0308–0327 | AUG |
| 31415 | ATGTTGGTATTGCACATTTG | 69 | 0309–0328 | AUG |
| 31416 | CATGTTGGTATTGCACATTT | 70 | 0310–0329 | AUG |
| 31417 | ACATGTTGGTATTGCACATT | 71 | 0311–0330 | AUG |
| 31418 | GACATGTTGGTATTGCACAT | 72 | 0312–0331 | AUG |
| 31419 | AGACATGTTGGTATTGCACA | 73 | 0313–0332 | AUG |
| 31420 | CAGACATGTTGGTATTGCAC | 74 | 0314–0333 | AUG |
| 31558 | CAGTAGGTACAGACATGTTG | 75 | 0323–0342 | coding |
| 31723 | TACAGCACCATCAGTAGGTA | 76 | 0334–0353 | coding |
| 31421 | GGAATCTGTGAGGTGGTTAC | 77 | 0351–0370 | coding |
| 31559 | TTCCGAAGCTGGAATCTGTG | 78 | 0361–0380 | coding |
| 31724 | AGGGTCTCTTGTTCCGAAGC | 79 | 0372–0391 | coding |
| 31422 | GCTTTGGTCTAACCAGGGTC | 80 | 0386–0405 | coding |
| 31560 | CAATGGCTTTGGTCTAACC | 81 | 0392–0411 | coding |
| 31725 | TAACTTCAAAAGCAATGGCT | 82 | 0403–0422 | coding |
| 31423 | GTGCACCAACAGACTTTAAT | 83 | 0422–0441 | coding |
| 31561 | ACCTCTTTCATAGTATAAGT | 84 | 0450–0469 | coding |
| 31726 | ATAATATACTGGCCAAGATA | 85 | 0477–0496 | coding |
| 31424 | TAATCGTTTAGTCATAATAT | 86 | 0490–0509 | coding |
| 31727 | ATCATATAATCGTTTAGTCA | 87 | 0496–0515 | coding |
| 31562 | GCTTCTCATCATATAATCGT | 88 | 0503–0522 | coding |
| 31728 | CAATATGTTGTTGCTTCTCA | 89 | 0515–0534 | coding |
| 31425 | GAACAATATACAATATGTTG | 90 | 0525–0544 | coding |
| 31729 | TCATTTGAACAATATACAAT | 91 | 0531–0550 | coding |
| 31563 | TAGAAGATCATTTGAACAAT | 92 | 0538–0557 | coding |
| 31730 | AACAAATCTCCTAGAAGATC | 93 | 0549–0568 | coding |
| 31426 | TGGCACGCCAAACAAATCTC | 94 | 0559–0578 | coding |
| 31731 | AGAAGCTTGGCACGCCAAAC | 95 | 0566–0585 | coding |
| 31564 | CTTTCACAGAGAAGCTTGGC | 96 | 0575–0594 | coding |
| 31732 | TTTTCCTGTGCTCTTTCACA | 97 | 0587–0606 | coding |
| 31427 | TATATATTTTCCTGTGCTCT | 98 | 0593–0612 | coding |
| 31733 | ATCATGGTATATATTTTCCT | 99 | 0600–0619 | coding |
| 31565 | TTCCTGTAGATCATGGTATA | 100 | 0609–0628 | coding |
| 31734 | TACTACCAAGTTCCTGTAGA | 101 | 0619–0638 | coding |
| 31428 | TTCCTGCTGATTGACTACTA | 102 | 0634–0653 | coding |
| 31566 | TGAGTCCGATGATTCCTGCT | 103 | 0646–0665 | coding |

TABLE 10-continued

Nucleotide Sequences of Human mdm2
Phosphorothioate Oligodeoxynucleotides

| ISIS NO. | NUCLEOTIDE SEQUENCE[1] (5' -> 3') | SEQ ID NO: | TARGET GENE NUCLEOTIDE CO-ORDINATES[2] | GENE TARGET REGION |
|---|---|---|---|---|
| 31735 | CAGATGTACCTGAGTCCGAT | 104 | 0656–0675 | coding |
| 31429 | CTGTTCTCACTCACAGATGT | 105 | 0669–0688 | coding |
| 31567 | TTCAAGGTGACACCTGTTCT | 106 | 0682–0701 | coding |
| 31736 | ACTCCCACCTTCAAGGTGAC | 107 | 0691–0710 | coding |
| 31430 | GGTCCTTTTGATCACTCCCA | 108 | 0704–0723 | coding |
| 31568 | AAGCTCTTGTACAAGGTCCT | 109 | 0718–0737 | coding |
| 31737 | CTCTTCCTGAAGCTCTTGTA | 110 | 0727–0746 | coding |
| 31431 | AAGATGAAGGTTTCTCTTCC | 111 | 0740–0759 | coding |
| 31569 | AAACCAAATGTGAAGATGAA | 112 | 0752–0771 | coding |
| 31738 | ATGGTCTAGAAACCAAATGT | 113 | 0761–0780 | coding |
| 31432 | CTAGATGAGGTAGATGGTCT | 114 | 0774–0793 | coding |
| 31570 | AATTGCTCTCCTTCTAGATG | 115 | 0787–0806 | coding |
| 31739 | TCTGTCTCACTAATTGCTCT | 116 | 0798–0817 | coding |
| 31433 | TCTGAATTTTCTTCTGTCTC | 117 | 0810–0829 | coding |
| 31571 | CACCAGATAATTCATCTGAA | 118 | 0824–0843 | coding |
| 31740 | TTTGTCGTTCACCAGATAAT | 119 | 0833–0852 | coding |
| 31434 | GTGGCGTTTTCTTTGTCGTT | 120 | 0844–0863 | coding |
| 31572 | TACTATCAGATTTGTGGCGT | 121 | 0857–0876 | coding |
| 31741 | GAAAGGGAAATACTATCAGA | 122 | 0867–0886 | coding |
| 31435 | GCTTTCATCAAAGGAAAGGG | 123 | 0880–0899 | coding |
| 31573 | TACACACAGAGCCAGGCTTT | 124 | 0895–0914 | coding |
| 31742 | CTCCCTTATTACACACAGAG | 125 | 0904–0923 | coding |
| 31436 | TCACAACATATCTCCCTTAT | 126 | 0915–0934 | coding |
| 31574 | CTACTGCTTCTTCACAACA | 127 | 0927–0946 | coding |
| 31743 | GATTCACTGCTACTGCTTCT | 128 | 0936–0955 | coding |
| 31437 | TGGCGTCCCTGTAGATTCAC | 129 | 0949–0968 | coding |
| 31575 | AAGATCCGGATTCGATGGCG | 130 | 0964–0983 | coding |
| 31744 | CAGCATCAAGATCCGGATTC | 131 | 0971–0990 | coding |
| 31438 | GTTCACTTACACCAGCATCA | 132 | 0983–1002 | coding |
| 31576 | CAATCACCTGAATGTTCACT | 133 | 0996–1015 | coding |
| 31745 | CTGATCCAACCAATCACCTG | 134 | 1006–1025 | coding |
| 31439 | GAAACTGAATCCTGATCCAA | 135 | 1017–1036 | coding |
| 31746 | TGATCTGAAACTGAATCCTG | 136 | 1023–1042 | coding |
| 31577 | CTACACTAAACTGATCTGAA | 137 | 1034–1053 | coding |
| 31747 | CAACTTCAAATTCTACACTA | 138 | 1046–1065 | coding |
| 31440 | AGATTCAACTTCAAATTCTA | 139 | 1051–1070 | coding |
| 31748 | GAGTCGAGAGATTCAACTTC | 140 | 1059–1078 | coding |
| 31578 | TAATCTTCTGAGTCGAGAGA | 141 | 1068–1087 | coding |
| 31749 | CTAAGGCTATAATCTTCTGA | 142 | 1077–1096 | coding |
| 31441 | TTCTTCACTAAGGCTATAAT | 143 | 1084–1103 | coding |
| 31750 | TCTTGTCCTTCTTCACTAAG | 144 | 1092–1111 | coding |
| 31579 | CTGAGAGTTCTTGTCCTTCT | 145 | 1100–1119 | coding |
| 31751 | TTCATCTGAGAGTTCTTGTC | 146 | 1105–1124 | coding |
| 31442 | CCTCATCATCTTCATCTGAG | 147 | 1115–1134 | coding |
| 31752 | CTTGATATACCTCATCATCT | 148 | 1124–1143 | coding |
| 31753 | ATACACAGTAACTTGATATA | 149 | 1135–1154 | coding |
| 31443 | CTCTCCCCTGCCTGATACAC | 150 | 1149–1168 | coding |
| 31580 | GAATCTGTATCACTCTCCCC | 151 | 1161–1180 | coding |
| 31754 | TCTTCAAATGAATCTGTATC | 152 | 1170–1189 | coding |
| 31444 | AAATTTCAGGATCTTCTTCA | 153 | 1184–1203 | coding |
| 31581 | AGTCAGCTAAGGAAATTTCA | 154 | 1196–1215 | coding |
| 31755 | GCATTTCCAATAGTCAGCTA | 155 | 1207–1226 | coding |
| 31445 | CATTGCATGAAGTGCATTTC | 156 | 1220–1239 | coding |
| 31756 | TCATTTCATTGCATGAAGTG | 157 | 1226–1245 | coding |
| 31582 | CATCTGTTGCAATGTGATGG | 158 | 1257–1276 | coding |
| 31757 | GAAGGGCCCAACATCTGTTG | 159 | 1268–1287 | coding |
| 31446 | TTCTCACGAAGGGCCCAACA | 160 | 1275–1294 | coding |
| 31758 | GAAGCCAATTCTCACGAAGG | 161 | 1283–1302 | coding |
| 31583 | TATCTTCAGGAAGCCAATTC | 162 | 1292–1311 | coding |
| 31759 | CTTTCCCTTTATCTTCAGGA | 163 | 1301–1320 | coding |
| 31447 | TCCCCTTTATCTTTCCCTTT | 164 | 1311–1330 | coding |
| 31584 | CTTTCTCAGAGATTTCCCCT | 165 | 1325–1344 | coding |
| 31760 | CAGTTTGGCTTTCTCAGAGA | 166 | 1333–1352 | coding |
| 31448 | GTGTTGAGTTTTCCAGTTTG | 167 | 1346–1365 | coding |
| 31585 | CCTCTTCAGCTTGTGTTGAG | 168 | 1358–1377 | coding |
| 31761 | ACATCAAAGCCCTCTTCAGC | 169 | 1368–1787 | coding |
| 31449 | GAATCATTCACTATAGTTTT | 170 | 1401–1420 | coding |
| 31586 | ATGACTCTCTGGAATCATTC | 171 | 1412–1431 | coding |
| 31762 | CCTCAACACATGACTCTCTG | 172 | 1421–1440 | coding |
| 31450 | TTATCATCATTTCCTCAAC | 173 | 1434–1453 | coding |
| 31763 | TAATTTTATCATCATTTTCC | 174 | 1439–1458 | coding |
| 31587 | GAAGCTTGTGTAATTTTATC | 175 | 1449–1468 | coding |
| 31764 | TGATTGTGAAGCTTGTGTAA | 176 | 1456–1475 | coding |

TABLE 10-continued

Nucleotide Sequences of Human mdm2
Phosphorothioate Oligodeoxynucleotides

| ISIS NO. | NUCLEOTIDE SEQUENCE[1] (5' -> 3') | SEQ ID NO: | TARGET GENE NUCLEOTIDE CO-ORDINATES[2] | GENE TARGET REGION |
|---|---|---|---|---|
| 31451 | CACTTTCTTGTGATTGTGAA | 177 | 1466–1485 | coding |
| 31588 | GCTGAGAATAGTCTTCACTT | 178 | 1481–1500 | coding |
| 31765 | AGTTGATGGCTGAGAATAGT | 179 | 1489–1508 | coding |
| 31452 | TGCTACTAGAAGTTGATGGC | 180 | 1499–1518 | coding |
| 31766 | TAAATAATGCTACTAGAAGT | 181 | 1506–1525 | coding |
| 31589 | CTTGGCTGCTATAAATAATG | 182 | 1517–1536 | coding |
| 31590 | ATCTTCTTGGCTGCTATAAA | 183 | 1522–1541 | coding |
| 31453 | AACTCTTTCACATCTTCTTG | 184 | 1533–1552 | coding |
| 31767 | CCCTTTCAAACTCTTTCACA | 185 | 1541–1560 | coding |
| 31591 | GGGTTTCTTCCCTTTCAAAC | 186 | 1550–1569 | coding |
| 31768 | TCTTTGTCTTGGGTTTCTTC | 187 | 1560–1579 | coding |
| 31454 | CTCTCTTCTTTGTCTTGGGT | 188 | 1566–1585 | coding |
| 31592 | AACTAGATTC6ACACTCTCT | 189 | 1580–1599 | coding |
| 31769 | CAAGGTTCAATGGCATTAAG | 190 | 1605–1624 | coding |
| 31455 | TGACAAATCACACAAGGTTC | 191 | 1617–1636 | coding |
| 31593 | TCGACCTTGACAAATCACAC | 192 | 1624–1643 | coding |
| 31594 | ATGGACAATGCAACCATTTT | 193 | 1648–1667 | coding |
| 31770 | TGTTTTGCCATGGACAATGC | 194 | 1657–1676 | coding |
| 31456 | TAAGATGTCCTGTTTTGCCA | 195 | 1667–1686 | coding |
| 31595 | GCAGGCCATAAGATGTCCTG | 196 | 1675–1694 | coding |
| 31596 | ACATGTAAAGCAGGCCATAA | 197 | 1684–1703 | coding |
| 31771 | CTTTGCACATGTAAAGCAGG | 198 | 1690–1709 | coding |
| 31457 | TTTCTTTAGCTTCTTTGCAC | 199 | 1702–1721 | coding |
| 31597 | TTATTCCTTTTCTTTAGCTT | 200 | 1710–1729 | coding |
| 31598 | TGGGCAGGGCTTATTCCTTT | 201 | 1720–1739 | coding |
| 31772 | ACATACTGGGCAGGGCTTAT | 202 | 1726–1745 | coding |
| 31458 | TTGGTTGTCTACATACTGGG | 203 | 1736–1755 | coding |
| 31599 | TCATTTGAATTGGTTGTCTA | 204 | 1745–1764 | coding |
| 31600 | AAGTTAGCACAATCATTTGA | 2os | 1757–1776 | coding |
| 31601 | TCTCTTATAGACAGGTCAAC | 206 | 1787–1806 | STOP |
| 31459 | AAATATATAATTCTCTTATA | 207 | 1798–1817 | 3' UTR |
| 31602 | AGTTAGAAATATATAATTCT | 208 | 1804–1823 | 3' UTR |
| 31773 | ATATAGTTAGAAATATATAA | 209 | 1808–1827 | 3' UTR |
| 31603 | CTAGGGTTATATAGTTAGAA | 210 | 1816–1835 | 3' UTR |
| 31774 | TAAATTCCTAGGGTTATATA | 211 | 1823–1842 | 3' UTR |
| 31460 | CAGGTTGTCTAAATTCCTAG | 212 | 1832–1851 | 3' UTR |
| 31604 | ATAAATTTCAGGTTGTCTAA | 213 | 1840–1859 | 3' UTR |
| 31605 | ATATATGTGAATAAATTTCA | 214 | 1850–1869 | 3' UTR |
| 31606 | CTTTGATATATGTGAATAAA | 215 | 1855–1874 | 3' UTR |
| 31461 | CATTTTCTCACTTTGATATA | 216 | 1865–1884 | 3' UTR |
| 31607 | ATTGAGGCATTTTCTCACTT | 217 | 1872–1891 | 3' UTR |
| 31608 | AATCTATGTGAATTGAGGCA | 218 | 1883–1902 | 3' UTR |
| 31609 | AGAAGAAATCTATGTGAATT | 219 | 1889–1908 | 3' UTR |
| 31462 | ATACTAAAGAGAAGAAATCT | 220 | 1898–1917 | 3' UTR |
| 31610 | GTCAATTATACTAAAGAGAA | 221 | 1905–1924 | 3' UTR |
| 31775 | TAGGTCAATTATACTAAAGA | 222 | 1908–1927 | 3' UTR |
| 31611 | CAAAGTAGGTCAATTATACT | 223 | 1913–1932 | 3' UTR |
| 31776 | CCACTACCAAAGTAGGTCAA | 224 | 1920–1939 | 3' UTR |
| 31463 | AGTATTCACTATTCCACTAC | 225 | 1933–1952 | 3' UTR |
| 31612 | TATACTAACTATTCACTATT | 226 | 1940–1959 | 3' UTR |
| 31613 | ACTCAAATTATACTAAGTAT | 227 | 1948–1967 | 3' UTR |
| 31777 | CATATTCAACTCAAATTATA | 228 | 1956–1975 | 3' UTR |
| 31464 | AAACCATCACCTACATATTC | 229 | 1969–1988 | 3' UTR |
| 31778 | CTCTAAACCATCACCTACAT | 230 | 1973–1992 | 3' UTR |
| 31614 | TACCACTTCCTCTAAACCAT | 231 | 1982–2001 | 3' UTR |
| 31779 | TTTAAAATTACCACTTCCTC | 232 | 1990–2009 | 3' UTR |
| 31615 | CAAATTATTTAAAATTACCA | 233 | 1997–2016 | 3' UTR |
| 31465 | CACACTACAAATTATTTAAA | 234 | 2004–2023 | 3' UTR |
| 31616 | CTCATTTAACACACACTACA | 235 | 2015–2034 | 3' UTR |
| 31780 | TACTTCTCATTTAACACACA | 236 | 2020–2039 | 3' UTR |
| 31617 | CATATACATATTTAACAAAA | 237 | 2051–2070 | 3' UTR |
| 31466 | TTAAATCTCATATACATATT | 238 | 2059–2078 | 3' UTR |
| 31618 | TAATAACTTACATTTAAATC | 239 | 2072–2091 | 3' UTR |
| 31619 | CTAACACACCAACACTCCCT | 240 | 2103–2122 | 3' UTR |
| 31467 | CACCCTCCCTAACACACCAA | 241 | 2111–2130 | 3' UTR |
| 31781 | CACTCCACCCTCCCTAACAC | 242 | 2116–2135 | 3' UTR |
| 31620 | CCCACTCCACTCCACCCTCC | 243 | 2123–2142 | 3' UTR |
| 31782 | CCCAACATCACCCACTCCAC | 244 | 2133–2152 | 3' UTR |
| 31621 | CCACTCACCCAACATCACCC | 245 | 2140–2159 | 3' UTR |
| 31468 | CACCTTCCACTCACCCAACA | 246 | 2146–2165 | 3' UTR |
| 31783 | CACCCCACACCTTCCACTCA | 247 | 2153–2172 | 3' UTR |
| 31622 | CACCACAATCCTCCCAACCC | 248 | 2176–2195 | 3' UTR |
| 31623 | ACCCTCACCCACCACAATCC | 249 | 2185–2204 | 3' UTR |

TABLE 10-continued

Nucleotide Sequences of Human mdm2
Phosphorothioate Oligodeoxynucleotides

| ISIS NO. | NUCLEOTIDE SEQUENCE[1] (5' -> 3') | SEQ ID NO: | TARGET GENE NUCLEOTIDE CO-ORDINATES[2] | GENE TARGET REGION |
|---|---|---|---|---|
| 31784 | ATTCCCACCCTCACCCACCA | 250 | 2191–2210 | 3' UTR |
| 31469 | CAACCTAATTCCCACCCTCA | 251 | 2198–2217 | 3' UTR |
| 31624 | ACCCCAACCTAATTCCCACC | 252 | 2202–2221 | 3' UTR |
| 31785 | ATCACTCTACCCCAACCTAA | 253 | 2210–2229 | 3' UTR |
| 31625 | CACATCACTCTACCCCAACC | 254 | 2213–2232 | 3' UTR |
| 31786 | GGTGGCAGATGACTGTAGGC | 255 | 2218–2237 | 3' UTR |
| 31626 | AGGTGTGGTGGCAGATGACT | 21 | 2224–2243 | 3' UTR |
| 31470 | AATTAGCCAGGTGTGGTGGC | 256 | 2232–2251 | 3' UTR |
| 31627 | GTCTCTACTAAAAGTACAAA | 257 | 2253–2272 | 3' UTR |
| 31628 | CGGTGAAACCCTGTCTCTAC | 258 | 2265–2284 | 3' UTR |
| 31787 | TGGCTAACACGGTGAAACCC | 259 | 2274–2293 | 3' UTR |
| 31471 | AGACCATCCTGGCTAACACG | 260 | 2283–2302 | 3' UTR |
| 31788 | GAGATCGAGACCATCCTGGC | 261 | 2290–2309 | 3' UTR |
| 31629 | GAGGTCAGGAGATCGAGACC | 262 | 2298–2317 | 3' UTR |
| 31789 | GCGGATCACGAGGTCAGGAG | 263 | 2307–2326 | 3' UTR |
| 31472 | AGGCCGAGGTGGGCGGATCA | 264 | 2319–2338 | 3' UTR |
| 31790 | TTTGGGAGGCCGAGGTGGGC | 265 | 2325–2344 | 3' UTR |
| 31630 | TCCCAGCACTTTGGGAGGCC | 266 | 2334–2353 | 3' UTR |
| 31791 | CCTGTAATCCCAGCACTTTG | 267 | 2341–2360 | 3' UTR |
| 31631 | GTGGCTCATGCCTGTAATCC | 268 | 2351–2370 | 3' UTR |

[1]All deoxy cytosines residues are 5-methyl-cytosines; all linkages are phosphorothioate linkages.
[2]Co-ordinates from Genbank Accession No. Z12020, locus name "HSP53ASSG", SEQ ID NO: 1.

TABLE 11

Nucleotide Sequences of Human mdm2
Chimeric (deoxy gapped) Oligonucleotides

| ISIS NO. | NUCLEOTIDE SEQUENCE[1] (5' -> 3') | SEQ ID NO: | TARGET GENE NUCLEOTIDE CO-ORDINATES[2] | GENE TARGET REGION |
|---|---|---|---|---|
| 31393 | CAGCCAAGCTCGCGCGGTGC | 3 | 0001–0020 | 5' UTR |
| 31712 | AAGCAGCCAAGCTCGCGCGG | 33 | 0004–0023 | 5' UTR |
| 31552 | CAGGCCCCAGAAGCAGCCAA | 34 | 0014–0033 | 5' UTR |
| 31713 | GCCACACAGGCCCCAGAAGC | 35 | 0020–0039 | 5' UTR |
| 31394 | ACACACAGGGCCACACAGGC | 36 | 0029–0048 | 5' UTR |
| 31714 | TTCCGACACACAGGGCCACA | 37 | 0034–0053 | 5' UTR |
| 31553 | GCTCCATCTTTCCGACACAC | 38 | 0043–0062 | 5' UTR |
| 31715 | GCTTCTTGCTCCATCTTTCC | 39 | 0050–0069 | 5' UTR |
| 31395 | CCCTCGGGCTCGGCTTCTTG | 40 | 0062–0081 | 5' UTR |
| 31716 | GCGGCCGCCCCTCGGGCTCG | 41 | 0070–0089 | 5' UTR |
| 31554 | AAGCAGCAGGATCTCGGTCA | 42 | 0098–0107 | 5' UTR |
| 31717 | GCTGCGAAAGCAGCAGGATC | 43 | 0105–0124 | 5' UTR |
| 31396 | TGCTCCTGGCTGCGAAAGCA | 44 | 0113–0132 | 5' UTR |
| 31718 | GGGACGGTGCTCCTGGCTGC | 45 | 0120–0139 | 5' UTR |
| 31555 | ACTGGGCGCTCGTACGCACT | 46 | 0150–0169 | 5' UTR |
| 31719 | GCCAGGGCACTGGGCGCTCG | 47 | 0158–0177 | 5' UTR |
| 31397 | TCTCCGGGCCAGGGCACTGG | 48 | 0165–0184 | 5' UTR |
| 31720 | TCATTCCACTCTCCGGGCCA | 49 | 0174–0193 | 5' UTR |
| 31556 | GGAAGCACGACGCCCTGGGC | 50 | 0202–0221 | 5' UTR |
| 31721 | TACTGCGGAAGCACGACGCC | 51 | 0208–0227 | 5' UTR |
| 31398 | GGGACTGACTACTGCGGAAG | 52 | 0217–0236 | 5' UTR |
| 31722 | TCAAGACTCCCCAGTTTCCT | 53 | 0242–0261 | 5' UTR |
| 31557 | CCTGCTCCTCACCATCCGGG | 54 | 0289–0308 | 5' UTR |
| 31399 | TTTGCCTGCTCCTCACCATC | 55 | 0293–0312 | AUG |
| 31400 | ATTTGCCTGCTCCTCACCAT | 56 | 0294–0313 | AUG |
| 31401 | CATTTGCCTGCTCCTCACCA | 9 | 0295–0314 | AUG |
| 31402 | ACATTTGCCTGCTCCTCACC | 57 | 0296–0315 | AUG |
| 31403 | CACATTTGCCTGCTCCTCAC | 58 | 0297–0316 | AUG |
| 31404 | GCACATTTGCCTGCTCCTCA | 59 | 0298–0317 | AUG |
| 31405 | TGCACATTTGCCTGCTCCTC | 60 | 0299–0318 | AUG |
| 31406 | TTGCACATTTGCCTGCTCCT | 61 | 0300–0319 | AUG |
| 31407 | ATTGCACATTTGCCTGCTCC | 62 | 0301–0320 | AUG |
| 31408 | TATTGCACATTTGCCTGCTC | 63 | 0302–0321 | AUG |
| 31409 | GTATTGCACATTTGCCTGCT | 10 | 0303–0322 | AUG |
| 31410 | GGTATTGCACATTTGCCTGC | 64 | 0304–0323 | AUG |
| 31411 | TGGTATTGCACATTTGCCTG | 65 | 0305–0324 | AUG |
| 31412 | TTGGTATTGCACATTTGCCT | 66 | 0306–0325 | AUG |
| 31413 | GTTGGTATTGCACATTTGCC | 67 | 0307–0326 | AUG |
| 31414 | TGTTGGTATTGCACATTTGC | 68 | 0308–0327 | AUG |

TABLE 11-continued

Nucleotide Sequences of Human mdm2
Chimeric (deoxy gapped) Oligonucleotides

| ISIS NO. | NUCLEOTIDE SEQUENCE[1] (5' -> 3') | SEQ ID NO: | TARGET GENE NUCLEOTIDE CO-ORDINATES[2] | GENE TARGET REGION |
| --- | --- | --- | --- | --- |
| 31415 | ATGTTGGTATTGCACATTTG | 69 | 0309–0328 | AUG |
| 31416 | CATGTTGGTATTGCACATTT | 70 | 0310–0329 | AUG |
| 31417 | ACATGTTGGTATTGCACATT | 71 | 0311–0330 | AUG |
| 31418 | GACATGTTGGTATTGCACAT | 72 | 0312–0331 | AUG |
| 31419 | AGACATGTTGGTATTGCACA | 73 | 0313–0332 | AUG |
| 31420 | CAGACATGTTGGTATTGCAC | 74 | 0314–0333 | AUG |
| 31558 | CAGTAGGTACAGACATGTTG | 75 | 0323–0342 | coding |
| 31723 | TACAGCACCATCAGTAGGTA | 76 | 0334–0353 | coding |
| 31421 | GGAATCTGTGAGGTGGTTAC | 77 | 0351–0370 | coding |
| 31559 | TTCCGAAGCTGGAATCTGTG | 78 | 0361–0380 | coding |
| 31724 | AGGGTCTCTTGTTCCGAAGC | 79 | 0372–0391 | coding |
| 31422 | GCTTTGGTCTAACCAGGGTC | 80 | 0386–0405 | coding |
| 31560 | GCAATGGCTTTGGTCTAACC | 81 | 0392–0411 | coding |
| 31725 | TAACTTCAAAAGCAATGGCT | 82 | 0403–0422 | coding |
| 31423 | GTGCACCAACAGACTTTAAT | 83 | 0422–0441 | coding |
| 31561 | ACCTCTTTCATAGTATAAGT | 84 | 0450–0469 | coding |
| 31726 | ATAATATACTGGCCAAGATA | 85 | 0477–0496 | coding |
| 31424 | TAATCGTTTAGTCATAATAT | 86 | 0490–0509 | coding |
| 31727 | ATCATATAATCGTTTAGTCA | 87 | 0496–0515 | coding |
| 31562 | GCTTCTCATCATATAATCGT | 88 | 0503–0522 | coding |
| 31728 | CAATATGTTGTTGCTTCTCA | 89 | 0515–0534 | coding |
| 31425 | GAACAATATACAATATGTTG | 90 | 0525–0544 | coding |
| 31729 | TCATTTGAACAATATACAAT | 91 | 0531–0550 | coding |
| 31563 | TAGAAGATCATTTGAACAAT | 92 | 0538–0557 | coding |
| 31730 | AACAAATCTCCTAGAAGATC | 93 | 0549–0568 | coding |
| 31426 | TGGCACGCCAAACAAATCTC | 94 | 0559–0578 | coding |
| 31731 | AGAAGCTTGGCACGCCAAAC | 95 | 0566–0585 | coding |
| 31564 | CTTTCACAGAGAAGCTTGGC | 96 | 0575–0594 | coding |
| 31732 | TTTTCCTGTGCTCTTTCACA | 97 | 0587–0606 | coding |
| 31427 | TATATATTTTCCTGTGCTCT | 98 | 0593–0612 | coding |
| 31733 | ATCATGGTATATATTTTCCT | 99 | 0600–0619 | coding |
| 31565 | TTCCTGTAGATCATGGTATA | 100 | 0609–0628 | coding |
| 31734 | TACTACCAAGTTCCTGTAGA | 101 | 0619–0638 | coding |
| 31428 | TTCCTGCTGATTGACTACTA | 102 | 0634–0653 | coding |
| 31566 | TGAGTCCGATGATTCCTGCT | 103 | 0646–0665 | coding |
| 31735 | CAGATGTACCTGAGTCCGAT | 104 | 0656–0675 | coding |
| 31429 | CTGTTCTCACTCACAGATGT | 105 | 0669–0688 | coding |
| 31567 | TTCAAGGTGACACCTGTTCT | 106 | 0682–0701 | coding |
| 31736 | ACTCCCACCTTCAAGGTGAC | 107 | 0691–0710 | coding |
| 31430 | GGTCCTTTTGATCACTCCCA | 108 | 0704–0723 | coding |
| 31568 | AAGCTCTTGTACAAGGTCCT | 109 | 0718–0737 | coding |
| 31737 | CTCTTCCTGAAGCTCTTGTA | 110 | 0727–0746 | coding |
| 31431 | AAGATGAAGGTTTCTCTTCC | 111 | 0740–0759 | coding |
| 31569 | AAACCAAATGTGAAGATGAA | 112 | 0752–0771 | coding |
| 31738 | ATGGTCTAGAAACCAAATGT | 113 | 0761–0780 | coding |
| 31432 | CTAGATGAGGTAGATGGTCT | 114 | 0774–0793 | coding |
| 31570 | AATTGCTCTCCTTCTAGATG | 115 | 0787–0806 | coding |
| 31739 | TCTGTCTCACTAATTGCTCT | 116 | 0798–0817 | coding |
| 31433 | TCTGAATTTTCTTCTGTCTC | 117 | 0810–0829 | coding |
| 31571 | CACCAGATAATTCATCTGAA | 118 | 0824–0843 | coding |
| 31740 | TTTGTCGTTCACCAGATAAT | 119 | 0833–0852 | coding |
| 31434 | GTGGCGTTTTCTTTGTCGTT | 120 | 0844–0863 | coding |
| 31572 | TACTATCAGATTTGTGGCGT | 121 | 0857–0876 | coding |
| 31741 | GAAAGGGAAATACTATCAGA | 122 | 0867–0336 | coding |
| 31435 | GCTTTCATCAAAGGAAAGGG | 123 | 0880–0899 | coding |
| 31573 | TACACACAGAGCCAGGCTTT | 124 | 0395–0914 | coding |
| 31742 | CTCCCTTATTACACACAGAG | 125 | 0904–0923 | coding |
| 31436 | TCACAACATATCTCCCTTAT | 126 | 0915–0934 | coding |
| 31574 | CTACTGCTTCTTTCACAACA | 127 | 0927–0946 | coding |
| 31743 | GATTCACTGCTACTGCTTCT | 128 | 0936–0955 | coding |
| 31437 | TGGCGTCCCTGTAGATTCAC | 129 | 0949–0968 | coding |
| 31575 | AAGATCCGGATTCGATGGCG | 130 | 0964–0983 | coding |
| 31744 | CAGCATCAAGATCCGGATTC | 131 | 0971–0990 | coding |
| 31438 | GTTCACTTACACCAGCATCA | 132 | 0983–1002 | coding |
| 31576 | CAATCACCTGAATGTTCACT | 133 | 0996–1015 | ccding |
| 31745 | CTGATCCAACCAATCACCTG | 134 | 1006–1025 | coding |
| 31439 | GAAACTGAATCCTGATCCAA | 135 | 1017–1036 | coding |
| 31746 | TGATCTGAAACTGAATCCTG | 136 | 1023–1042 | coding |
| 31577 | CTACACTAAACTGATCTGAA | 137 | 1034–1053 | coding |
| 31747 | CAACTTCAAATTCTACACTA | 138 | 1046–1065 | coding |
| 31440 | AGATTCAACTTCAAATTCTA | 139 | 1051–1070 | coding |
| 31748 | GAGTCGAGAGATTCAACTTC | 140 | 1059–1078 | coding |
| 31578 | TAATCTTCTGAGTCGAGAGA | 141 | 1068–1087 | coding |

TABLE 11-continued

Nucleotide Sequences of Human mdm2
Chimeric (deoxy gapped) Oligonucleotides

| ISIS NO. | NUCLEOTIDE SEQUENCE[1] (5' -> 3') | SEQ ID NO: | TARGET GENE NUCLEOTIDE CO-ORDINATES[2] | GENE TARGET REGION |
|---|---|---|---|---|
| 31749 | CTAAGGCTATAATCTTCTGA | 142 | 1077–1096 | coding |
| 31441 | TTCTTCACTAAGGCTATAAT | 143 | 1084–1103 | coding |
| 31750 | TCTTGTCCTTCTTCACTAAG | 144 | 1092–1111 | ccding |
| 31579 | CTGAGAGTTCTTGTCCTTCT | 145 | 1100–1119 | coding |
| 31751 | TTCATCTGAGAGTTCTTGTC | 146 | 1105–1124 | coding |
| 31442 | CCTCATCATCTTCATCTGAG | 147 | 1115–1134 | coding |
| 31752 | CTTGATATACCTCATCATCT | 143 | 1124–1143 | coding |
| 31753 | ATACACAGTAACTTGATATA | 149 | 1135–1154 | coding |
| 31443 | CTCTCCCCTGCCTGATACAC | 150 | 1149–1168 | coding |
| 31580 | GAATCTGTATCACTCTCCCC | 151 | 1161–1180 | coding |
| 31754 | TCTTCAAATGAATCTGTATC | 152 | 1170–1189 | coding |
| 31444 | AAATTTCAGGATCTTCTTCA | 153 | 1184–1203 | coding |
| 31531 | AGTCAGCTAAGGAAATTTCA | 154 | 1196–1215 | coding |
| 31755 | GCATTTCCAATAGTCAGCTA | 155 | 1207–1226 | coding |
| 31445 | CATTGCATGAAGTGCATTTC | 156 | 1220–1239 | coding |
| 31756 | TCATTTCATTGCATGAAGTG | 157 | 1226–1245 | coding |
| 31582 | CATCTGTTGCAATGTGATGG | 158 | 1257–1276 | coding |
| 31757 | GAAGGGCCCAACATCTGTTG | 159 | 1268–1237 | coding |
| 31446 | TTCTCACGAAGGGCCCAACA | 160 | 1275–1294 | coding |
| 31758 | GAAGCCAATTCTCACGAAGG | 161 | 1283–1302 | coding |
| 31583 | TATCTTCAGGAAGCCAATTC | 162 | 1292–1311 | coding |
| 31759 | CTTTCCCTTTATCTTCAGGA | 163 | 1301–1320 | coding |
| 31447 | TCCCCTTTATCTTTCCCTTT | 164 | 1311–1330 | coding |
| 31584 | CTTTCTCAGAGATTTCCCCT | 165 | 1325–1344 | coding |
| 31760 | CAGTTTGGCTTTCTCAGAGA | 166 | 1333–1352 | coding |
| 31448 | GTGTTGAGTTTTCCAGTTTG | 167 | 1346–1365 | coding |
| 31585 | CCTCTTCAGCTTGTGTTGAG | 168 | 1358–1377 | coding |
| 31761 | ACATCAAAGCCCTCTTCAGC | 169 | 1368–1787 | coding |
| 31449 | GAATCATTCACTATAGTTTT | 170 | 1401–1420 | coding |
| 31586 | ATGACTCTCTGGAATCATTC | 171 | 1412–1431 | coding |
| 31762 | CCTCAACACATGACTCTCTG | 172 | 1421–1440 | coding |
| 31450 | TTATCATCATTTTCCTCAAC | 173 | 1434–1453 | coding |
| 31763 | TAATTTATCATCATTTTCC | 174 | 1439–1458 | coding |
| 31587 | GAAGCTTGTGTAATTTATC | 175 | 1449–1468 | coding |
| 31764 | TGATTGTGAAGCTTGTGTAA | 176 | 1456–1475 | coding |
| 31451 | CACTTTCTTGTGATTGTGAA | 177 | 1466–1485 | coding |
| 31588 | GCTGAGAATAGTCTTCACTT | 178 | 1481–1500 | coding |
| 31765 | AGTTGATGGCTGAGAATAGT | 179 | 14S9–150S | coding |
| 31452 | TGCTACTAGAAGTTGATGGC | 180 | 1499–1518 | coding |
| 31766 | TAAATAATGCTACTAGAAGT | 181 | 1506–1525 | coding |
| 31589 | CTTGGCTGCTATAAATAATG | 182 | 1517–1536 | coding |
| 31590 | ATCTTCTTGGCTGCTATAAA | 183 | 1522–1541 | coding |
| 31453 | AACTCTTTCACATCTTCTTG | 1S4 | 1533–1552 | coding |
| 31767 | CCCCTTTCAAACTCTTTCACA | 185 | 1541–1560 | coding |
| 31591 | GGGTTTCTTCCCTTTCAAAC | 186 | 1550–1569 | coding |
| 31768 | TCTTTGTCTTGGGTTTCTTC | 187 | 1560–1579 | coding |
| 31454 | CTCTCTTCTTTGTCTTGGGT | 188 | 1566–1585 | coding |
| 31592 | AACTAGATTCCACACTCTCT | 189 | 1580–1599 | coding |
| 31769 | CAAGGTTCAATGGCATTAAG | 190 | 1605–1624 | coding |
| 31455 | TGACAAATCACACAAGGTTC | 191 | 1617–1636 | coding |
| 31593 | TCGACCTTGACAAATCACAC | 192 | 1624–1643 | coding |
| 31594 | ATGGACAATGCAACCATTTT | 193 | 1648–1667 | coding |
| 31770 | TGTTTTGCCATGGACAATGC | i94 | 1657–1676 | coding |
| 31456 | TAAGATGTCCTGTTTTGCCA | 195 | 1667–1686 | coding |
| 31595 | GCAGGCCATAAGATGTCCTG | 196 | 1675–1694 | coding |
| 31596 | ACATGTAAAGCAGGCCATAA | 197 | 1684–1703 | coding |
| 31771 | CTTTGCACATGTAAAGCAGG | 198 | 1690–1709 | coding |
| 31457 | TTTCTTTAGCTTCTTGCAC | 199 | 1702–1721 | coding |
| 31597 | TTATTCCTTTTCTTTAGCTT | 200 | 1710–1729 | coding |
| 31598 | TGGGCAGGGCTTATTCCTTT | 201 | 1720–1739 | coding |
| 31772 | ACATACTGGGCAGGGCTTAT | 202 | 1726–1745 | coding |
| 31458 | TTGGTTGTCTACATACTGGG | 203 | 1736–1755 | coding |
| 31599 | TCATTTGAATTGGTTGTCTA | 204 | 1745–1764 | coding |
| 31600 | AAGTTAGCACAATCATTTGA | 205 | 1757–1776 | coding |
| 31601 | TCTCTTATAGACAGGTCAAC | 206 | 1787–1806 | STOP |
| 31459 | AAATATATAATTCTCTTATA | 207 | 1798–1817 | 3' UTR |
| 31602 | AGTTAGAAATATATAATTCT | 208 | 1804–1823 | 3' UTR |
| 31773 | ATATAGTTAGAAATATATAA | 209 | 1808–1827 | 3' UTR |
| 31603 | CTAGGGTTATATAGTTAGAA | 210 | 1816–1835 | 3' UTR |
| 31774 | TAAATTCCTAGGGTTATATA | 211 | 1823–1842 | 3' UTR |
| 31460 | CAGGTTGTCTAAATTCCTAG | 212 | 1832–1851 | 3' UTR |
| 31604 | ATAAATTTCAGGTTGTCTAA | 213 | 1340–1359 | 3' UTR |
| 31605 | ATATATGTGAATAAATTTCA | 214 | 1850–1869 | 3' UTR |

TABLE 11-continued

Nucleotide Sequences of Human mdm2
Chimeric (deoxy gapped) Oligonucleotides

| ISIS NO. | NUCLEOTIDE SEQUENCE[1] (5' -> 3') | SEQ ID NO: | TARGET GENE NUCLEOTIDE CO-ORDINATES[2] | GENE TARGET REGION |
|---|---|---|---|---|
| 31606 | CTTTGATATATGTGAATAAA | 215 | 1855–1874 | 3' UTR |
| 31461 | CATTTTCTCACTTTGATATA | 216 | 1865–1884 | 3' UTR |
| 31607 | ATTGAGGCATTTTCTCACTT | 217 | 1872–1891 | 3' UTR |
| 31608 | AATCTATGTGAATTGAGGCA | 218 | 1883–1902 | 3' UTR |
| 31609 | AGAAGAAATCTATGTGAATT | 219 | 1889–1908 | 3' UTR |
| 31462 | ATACTAAAGAGAAGAAATCT | 220 | 1898–1917 | 3' UTR |
| 31610 | GTCAATTATACTAAAGAGAA | 221 | 1905–1924 | 3' UTR |
| 31775 | TAGGTCAATTATACTAAAGA | 222 | 1908–1927 | 3' UTR |
| 31611 | CAAAGTAGGTCAATTATACT | 223 | 1913–1932 | 3' UTR |
| 31776 | CCACTACCAAAGTAGGTCAA | 224 | 1920–1939 | 3' UTR |
| 31463 | AGTATTCACTATTCCACTAC | 225 | 1933–1952 | 3' UTR |
| 31612 | TATAGTAAGTATTCACTATT | 226 | 1940–1959 | 3' UTR |
| 31613 | AGTCAAATTATAGTAAGTAT | 227 | 1948–1967 | 3' UTR |
| 31777 | CATATTCAAGTCAAATTATA | 228 | 1956–1975 | 3' UTR |
| 31464 | AAAGGATGAGCTACATATTC | 229 | 1969–1988 | 3' UTR |
| 31778 | GTGTAAAGGATGAGCTACAT | 230 | 1973–1992 | 3' UTR |
| 31614 | TAGGAGTTGGTGTAAAGGAT | 231 | 1982–2001 | 3' UTR |
| 31779 | TTTAAAATTAGGAGTTGGTG | 232 | 1990–2009 | 3' UTR |
| 31615 | GAAATTATTTAAAATTAGGA | 233 | 1997–2016 | 3' UTR |
| 31465 | CAGAGTAGAAATTATTTAAA | 234 | 2004–2023 | 3' UTR |
| 31616 | CTCATTTAAGACAGAGTAGA | 235 | 2015–2034 | 3' UTR |
| 31780 | TACTTCTCATTTAAGACAGA | 236 | 2020–2039 | 3' UTR |
| 31617 | CATATACATATTTAAGAAAA | 237 | 2051–2070 | 3' UTR |
| 31466 | TTAAATGTCATATACATATT | 238 | 2059–2078 | 3' UTR |
| 31618 | TAATAAGTTACATTTAAATG | 239 | 2072–2091 | 3' UTR |
| 31619 | GTAACAGAGCAAGACTCGGT | 240 | 2103–2122 | 3' UTR |
| 31467 | CAGCCTGGGTAACAGAGCAA | 241 | 2111–2130 | 3' UTR |
| 31781 | CACTCCAGCCTGGGTAACAG | 242 | 2116–2135 | 3' UTR |
| 31620 | CCCACTGCACTCCAGCCTGG | 243 | 2123–2142 | 3' UTR |
| 31782 | GCCAAGATCACCCACTGCAC | 244 | 2133–2152 | 3' UTR |
| 31621 | GCAGTGAGCCAAGATCACCC | 245 | 2140–2159 | 3' UTR |
| 31468 | GAGCTTGCAGTGAGCCAAGA | 246 | 2146–2165 | 3' UTR |
| 31783 | GAGGGCAGAGCTTGCAGTGA | 247 | 2153–2172 | 3' UTR |
| 31622 | CAGGAGAATGGTGCGAACCC | 248 | 2176–2195 | 3' UTR |
| 31623 | AGGCTGAGGCAGGAGAATGG | 249 | 2185–2204 | 3' UTR |
| 31784 | ATTGGGAGGCTGAGGCAGGA | 250 | 2191–2210 | 3' UTR |
| 31469 | CAAGCTAATTGGGAGGCTGA | 251 | 2198–2217 | 3' UTR |
| 31624 | AGGCCAAGCTAATTGGGAGG | 252 | 2202–2221 | 3' UTR |
| 31785 | ATGACTGTAGGCCAAGCTAA | 253 | 2210–2229 | 3' UTR |
| 31625 | CAGATGACTGTAGGCCAAGC | 254 | 2213–2232 | 3' UTR |
| 31786 | GGTGGCAGATGACTGTAGGC | 255 | 2218–2237 | 3' UTR |
| 31626 | AGGTGTGGTGGCAGATGACT | 21 | 2224–2243 | 3' UTR |
| 31470 | AATTAGCCAGGTGTGGTGGC | 256 | 2232–2251 | 3' UTR |
| 31627 | GTCTCTACTAAAAGTACAAA | 257 | 2253–2272 | 3' UTR |
| 31628 | CGGTGAAACCCTGTCTCTAC | 258 | 2265–2284 | 3' UTR |
| 31787 | TGGCTAACACGGTGAAACCC | 259 | 2274–2293 | 3' UTR |
| 31471 | AGACCATCCTGGCTAACACG | 260 | 2283–2302 | 3' UTR |
| 31788 | GAGATCGAGACCATCCTGGC | 261 | 2290–2309 | 3' UTR |
| 31629 | GAGGTCAGGAGATCGAGACC | 262 | 2298–2317 | 3' UTR |
| 31789 | GCGGATCACGAGGTCAGGAG | 263 | 2307–2326 | 3' UTR |
| 31472 | AGGCCGAGGTGGGCGGATCA | 264 | 2319–2338 | 3' UTR |
| 31790 | TTTGGGAGGCCGAGGTGGGC | 265 | 2325–2344 | 3' UTR |
| 31630 | TCCCAGCACTTTGGGAGGCC | 266 | 2334–2353 | 3' UTR |
| 31791 | CCTGTAATCCCAGCACTTTG | 267 | 2341–2360 | 3' UTR |
| 31631 | GTGGCTCATGCCTGTAATCC | 268 | 2351–2370 | 3' UTR |

[1]All deoxy cytosines and 2'-MOE cytosine residues are 5-methyl-cytosines; all linkages are phosphorothioate linkages.
[2]Co-ordinates from Genbank Accession No. Z12020, locus name "HSP53ASSG", SEQ ID NO: 1.

Oligonucleotide activity was assayed by quantitation of mdm2 mRNA levels by real-time PCR (RT-PCR) using the ABI PRISM™ 7700 Sequence Detection System (PE-Applied Biosystems, Foster City, Calif.) according to manufacturer's instructions. This is a closed-tube, non-gel-based, fluorescence detection system which allows high-throughput quantitation of polymerase chain reaction (PCR) products in real-time. As opposed to standard PCR, in which amplification products are quantitated after the PCR is completed, products in RT-PCR are quantitated as they accumulate. This is accomplished by including in the PCR reaction an oligonucleotide probe that anneals specifically between the forward and reverse PCR primers, and contains two fluorescent dyes. The primers and probes used were:

Forward: 5'-GGCAAATGTGCAATACCAACA-3' (SEQ ID NO. 269)
Reverse: 5'-TGCACCAACAGACTTTAATAACTTCA-3' (SEQ ID NO. 270)
Probe: 5'-FAM-CCACCTCACAGATTCCAGCTTCGGA-TAMRA-3' (SEQ ID NO. 271)

A reporter dye (e.g., JOE or FAM, PE-Applied Biosystems, Foster City, Calif.) was attached to the 5' end of the probe and a quencher dye (e.g., TAMRA, PE-Applied Biosystems, Foster City, Calif.) was attached to the 3' end of the probe. When the probe and dyes are intact, reporter dye emission is quenched by the proximity of the 3' quencher dye. During amplification, annealing of the probe to the target sequence creates a substrate that can be cleaved by the 5'-exonuclease activity of Taq polymerase. During the extension phase of the PCR amplification cycle, cleavage of the probe by Taq polymerase releases the reporter dye from the remainder of the probe (and hence from the quencher moiety) and a sequence-specific fluorescent signal is generated. With each cycle, additional reporter dye molecules are cleaved from their respective probes, and the fluorescence intensity is monitored at regular (six-second) intervals by laser optics built into the ABI PRISM™ 7700 Sequence Detection System. In each assay, a series of parallel reactions containing serial dilutions of mRNA from untreated control samples generates a standard curve that is used to quantitate the percent inhibition after antisense oligonucleotide treatment of test samples.

RT-PCR reagents were obtained from PE-Applied Biosystems, Foster City, Calif. RT-PCR reactions were carried out by adding 25 μl PCR cocktail (1× TAQMAN® buffer A, 5.5 mM MgCl$_2$, 300 μM each of dATP, dCTP and dGTP, 600 μM of dUTP, 100 nM each of forward primer, reverse primer, and probe, 20 U RNAse inhibitor, 1.25 units AMPLITAQ GOLD®, and 12.5 U MuLV reverse transcriptase) to 96 well plates containing 25 μl poly(A) mRNA solution. The RT reaction was carried out by incubation for 30 minutes at 48° C. Following a 10 minute incubation at 95° C. to activate the AMPLITAQ GOLD®, 40 cycles of a two-step PCR protocol were carried out: 95° C. for 15 seconds (denaturation) followed by 60° C. for 1.5 minutes (annealing/extension).

Results are shown in Table 12. Oligonucleotides 31394 (SEQ ID NO: 36), 31398 (SEQ ID NO: 52), 31400 (SEQ ID NO: 56), 31402 (SEQ ID NO: 57), 31405 (SEQ ID NO: 60), 31406 (SEQ ID NO: 61), 31415 (SEQ ID NO: 69), 31416 (SEQ ID NO: 70), 31418 (SEQ ID NO: 72), 31434 (SEQ ID NO: 60), 31436 (SEQ ID NO: 126), 31446 (SEQ ID NO: 160), 31451 (SEQ ID NO: 177), 31452 (SEQ ID NO: 180), 31456 (SEQ ID NO: 195), 31461 (SEQ ID NO: 216), 31468 (SEQ ID NO: 246), 31469 (SEQ ID NO: 251), 31471 (SEQ ID NO: 260), and 31472 (SEQ ID NO: 264) gave at least approximately 50% reduction of mdm2 mRNA levels.

TABLE 12

Activities of Phosphorothioate Oligodeoxynucleotides Targeted to Human mdm2

| ISIS No: | SEQ ID NO: | GENE TARGET REGION | % mRNA EXPRESSION | % mRNA INHIBITION |
|---|---|---|---|---|
| LIPOFECTIN ™ only | — | — | 100% | 0% |
| 31393 | 3 | 5' UTR | 59% | 41% |
| 31394 | 36 | 5' UTR | 27% | 73% |
| 31395 | 40 | 5' UTR | 96% | 4% |
| 31396 | 44 | 5' UTR | 99% | 1% |
| 31397 | 48 | 5' UTR | 76% | 24% |
| 31398 | 52 | 5' UTR | 51% | 49% |
| 31399 | 55 | AUG | 138% | — |
| 31400 | 56 | AUG | 22% | 78% |
| 31401 | 9 | AUG | 69% | 31% |
| 31402 | 57 | AUG | 47% | 53% |
| 31403 | 58 | AUG | 77% | 23% |
| 31404 | 59 | AUG | 60% | 40% |
| 31405 | 60 | AUG | 35% | 65% |

TABLE 12-continued

Activities of Phosphorothioate Oligodeoxynucleotides Targeted to Human mdm2

| ISIS No: | SEQ ID NO: | GENE TARGET REGION | % mRNA EXPRESSION | % mRNA INHIBITION |
|---|---|---|---|---|
| 31406 | 61 | AUG | 45% | 55% |
| 31407 | 62 | AUG | 65% | 35% |
| 31408 | 63 | AUG | 71% | 29% |
| 31409 | 10 | AUG | 849% | — |
| 31410 | 64 | AUG | 79% | 21% |
| 31411 | 65 | AUG | 67% | 33% |
| 31412 | 66 | AUG | 99% | 1% |
| 31413 | 67 | AUG | 68% | 32% |
| 31414 | 68 | AUG | 64% | 36% |
| 31415 | 69 | AUG | 48% | 52% |
| 31416 | 70 | AUG | 36% | 64% |
| 31417 | 71 | AUG | 77% | 23% |
| 31418 | 72 | AUG | 53% | 47% |
| 31419 | 73 | AUG | 122% | — |
| 31420 | 74 | AUG | 57% | 43% |
| 31421 | 77 | coding | 111% | — |
| 31422 | 80 | coding | 85% | 15% |
| 31423 | 83 | coding | 126% | — |
| 31424 | 86 | coding | 70% | 30% |
| 31425 | 90 | coding | 95% | 5% |
| 31426 | 94 | coding | 69% | 31% |
| 31427 | 98 | coding | 9465% | — |
| 31428 | 102 | coding | 81% | 19% |
| 31429 | 105 | coding | 138% | — |
| 31430 | 108 | coding | 114% | — |
| 31431 | 111 | coding | 77% | 23% |
| 31432 | 114 | coding | 676% | — |
| 31433 | 117 | coding | 145% | — |
| 31434 | 120 | coding | 40% | 60% |
| 31435 | 123 | coding | 193% | — |
| 31436 | 126 | coding | 49% | 51% |
| 31437 | 129 | coding | 146% | — |
| 31438 | 132 | coding | 76% | 24% |
| 31439 | 135 | coding | 104% | — |
| 31440 | 139 | coding | 95% | 5% |
| 31441 | 143 | coding | 324% | — |
| 31442 | 147 | coding | 1840% | — |
| 31443 | 150 | coding | 369% | — |
| 31444 | 153 | coding | 193% | — |
| 31445 | 156 | coding | 106% | — |
| 31446 | 160 | coding | 29% | 71% |
| 31447 | 164 | coding | 82% | 18% |
| 31448 | 167 | coding | 117% | — |
| 31449 | 170 | coding | 1769% | — |
| 31450 | 173 | coding | 84% | 16% |
| 31451 | 177 | coding | 49% | 51% |
| 31452 | 180 | coding | 33% | 67% |
| 31453 | 184 | coding | 59% | 41% |
| 31454 | 188 | coding | 171% | — |
| 31455 | 191 | coding | 61% | 39% |
| 31456 | 195 | coding | 42% | 58% |
| 31457 | 199 | coding | 70% | 30% |
| 31458 | 203 | coding | 60% | 40% |
| 31459 | 207 | 3' UTR | 149% | — |
| 31460 | 212 | 3' UTR | 71% | 29% |
| 31461 | 216 | 3' UTR | 52% | 48% |
| 31462 | 220 | 3' UTR | 1113% | — |
| 31463 | 225 | 3' UTR | 78% | 22% |
| 31464 | 229 | 3' UTR | 112% | — |
| 31465 | 234 | 3' UTR | 66% | 34% |
| 31466 | 238 | 3' UTR | 212% | — |
| 31467 | 241 | 3' UTR | 77% | 23% |
| 31468 | 246 | 3' UTR | 17% | 83% |
| 31469 | 251 | 3' UTR | 36% | 64% |
| 31470 | 256 | 3' UTR | 60% | 40% |
| 31471 | 260 | 3' UTR | 43% | 57% |
| 31472 | 264 | 3' UTR | 35% | 65% |

Example 10

Effect of mdm2 Antisense Oligonucleotides on the Growth of Human A549 Lung Tumor Cells in Nude Mice 200 μl of A549 cells (5×10⁶ cells) are implanted subcutaneously in the inner thigh of nude mice. mdm2 antisense oligonucleotides are administered twice weekly for four weeks, beginning one week following tumor cell inoculation. Oligonucleotides are formulated with cationic lipids (LIPOFECTIN™) and given subcutaneously in the vicinity of the tumor. Oligonucleotide dosage was 5 mg/kg with 60 mg/kg cationic lipid. Tumor size is recorded weekly.

Activity of the oligonucleotides is measured by reduction in tumor size compared to controls.

Example 11

U-87 Human Glioblastoma Cell Culture and Subcutaneous Xenografts into Nude Mice The U-87 human glioblastoma cell line is obtained from the ATCC (Manassas, Va.) and maintained in Iscove's DMEM medium supplemented with heat-inactivated 10% fetal calf serum (Yazaki, T., et al., *Mol. Pharmacol.*, 1996, 50, 236–242). Nude mice are injected subcutaneously with 2×10⁷ cells. Mice are injected intraperitoneally with oligonucleotide at dosages of either 2 mg/kg or 20 mg/kg for 21 consecutive days beginning 7 days after xenografts were implanted. Tumor volumes are measured on days 14, 21, 24, 31 and 35. Activity is measure by a reduced tumor volume compared to saline or sense oligonucleotide controls.

Example 12

Intracerebral U-87 Glioblastoma Xenografts into Nude Mice

U-87 cells are implanted in the brains of nude mice (Yazaki, T., et al., *Mol. Pharmacol.*, 1996, 50, 236–242). Mice are treated via continuous intraperitoneal administration of antisense oligonucleotide (20 mg/kg), control sense oligonucleotide (20 mg/kg) or saline beginning on day 7 after xenograft implantation. Activity of the oligonucleotide is measured by an increased survival time compared to controls.

---

What is claimed is:

1. An antisense compound 8 to 30 nucleobases in length targeted to nucleobases 1–308 of the 5' untranslated region, 1776–1806 of the translation termination codon region or 1818–2370 of the 3' untranslated region of a nucleic acid molecule encoding human mdm2, wherein said antisense compound modulates the expression of human mdm2.

2. The antisense compound of claim 1 wherein said antisense compound inhibits the expression of human mdm2.

3. The antisense compound of claim 2 comprising SEQ ID NO: 4.

4. A method of reducing hyperproliferation of human cells comprising contacting proliferating human cells in vitro with the antisense compound of claim 2 or a composition comprising said antisense compound.

5. The antisense compound of claim 1 which is an antisense oligonucleotide.

6. The antisense compound of claim 1 which contains at least one phosphorothioate intersugar linkage.

7. The antisense compound of claim 1 which has at least one 2'-O-methoxyethyl modification.

8. The antisense compound of claim 1 which contains at least one 5-methyl cytidine.

9. The antisense compound of claim 7 in which every 2'-O-methoxyethyl modified residue is a 5-methyl cytidine.

10. A method of modulating the expression of human mdm2 in human cells or tissues comprising contacting said cells or tissues in vitro with the antisense compound of claim 1.

11. An antisense compound up to 30 nucleobases in length comprising at least an 8-nucleobase portion of SEQ ID NO: 3, SEQ ID NO: 4, SEQ ID NO: 5, SEQ ID NO: 7, SEQ ID NO: 17, SEQ ID NO: 18, SEQ ID NO: 19, SEQ ID NO: 21, SEQ ID NO: 36, SEQ ID NO: 52, SEQ ID NO: 216, SEQ ID NO: 246, SEQ ID NO: 251, SEQ ID NO: 260, or SEQ ID NO: 264 which inhibits the expression of human mdm2.

12. An antisense compound up to 30 nucleobases in length targeted to a 5' untranslated region of a nucleic acid molecule encoding a S-mdm2 transcript, wherein said antisense compound inhibits the expression of said S-mdm2 transcript and comprises at least an 8 nucleobase portion of SEQ ID NO:3, SEQ ID NO:4, SEQ ID NO:5 or SEQ ID NO:7.

13. An antisense compound up to 30 nucleobases in length comprising at least an 8-nucleobase portion of SEQ ID NO: 15, SEQ ID NO: 56, SEQ ID NO: 57, SEQ ID NO: 120, SEQ ID NO: 126, SEQ ID NO: 160, SEQ ID NO: 177, SEQ ID NO: 180, or SEQ ID NO: 195.

14. The antisense compound of claim 13 which contains at least one phosphorothioate intersugar linkage.

15. The antisense compound of claim 13 which has at least one 2'-O-methoxyethyl modification.

16. The antisense compound of claim 13 which contains at least one 5-methyl cytidine.

17. The antisense compound of claim 15 in which every 2'-O-methoxyethyl modified residue is a 5-methyl cytidine.

18. A method of modulating the expression of human mdm2 in cells or tissues comprising contacting said cells or tissues in vitro with the antisense compound of claim 13.

19. A method of reducing hyperproliferation of human cells comprising contacting proliferating human cells in vitro with the antisense compound of claim 13.

20. An antisense compound consisting of SEQ ID NO: 60, 61, 69 or 70.

* * * * *

UNITED STATES PATENT AND TRADEMARK OFFICE
CERTIFICATE OF CORRECTION

PATENT NO.   : 6,184,212 B1
DATED        : February 6, 2001
INVENTOR(S)  : Miraglia et al.

It is certified that error appears in the above-identified patent and that said Letters Patent is hereby corrected as shown below:

Column 14,
Line 58, please delete "tic" and insert -- tlc --.

Column 22,
Line 60, before "mdm2", please insert -- on human --.

Column 23,
Line 25, please delete "49" and insert -- A549 --.

Column 27, Table 10,
Please insert as the first row following the table header
-- 31393    CAGCCAAGCTCGCGCGGTGC    3        0001-0020       5'UTR --.

Column 31,
Column 3, row 29 of Table 10, please delete "2os" and insert -- 205 --.

Column 31,
Column 2, row 63 of Table 10, please delete "TAATAACTTACATTTAAATC" and insert -- TAATAAGTTACATTTAAATG --.
Column 2, row 64 of Table 10, please delete "CTAACACACCAACACTCCCT" and insert -- GTAACAGAGCAAGACTCGGT --.
Column 2, row 65 of Table 10, please delete "CACCCTCCCTAACACACCAA" and insert -- CAGCCTGGGTAACAGAGCAA --.
Column 2, row 66 of Table 10, please delete "CACTCCACCCTCCCTAACAC" and insert -- CACTCCAGCCTGGGTAACAG --.
Column 2, row 67 of Table 10, please delete "CCCACTCCACTCCACCCTCC" and insert -- CCCACTGCACTCCAGCCTGG --.
Column 2, row 68 of Table 10, please delete "CCCAACATCACCCACTCCAC" and insert -- GCCAAGATCACCCACTGCAC --.
Column 2, row 69 of Table 10, please delete "CCACTCACCCAACATCACCC" and insert -- GCAGTGAGCCAAGATCACCC --.
Column 2, row 70 of Table 10, please delete "CACCTTCCACTCACCCAACA" and insert -- GAGCTTGCAGTGAGCCAAGA --.
Column 2, row 71 of Table 10, please delete "CACCCCACACCTTCCACTCA" and insert -- GAGGGCAGAGCTTGCAGTGA --.
Column 2, row 72 of Table 10, please delete "CACCACAATCCTCCCAACCC" and insert -- CAGGAGAATGGTGCGAACCC --.
Column 2, row 73 of Table 10, please delete "ACCCTCACCCACCACAATCC" and insert -- AGGCTGAGGCAGGAGAATGG --.

UNITED STATES PATENT AND TRADEMARK OFFICE
CERTIFICATE OF CORRECTION

PATENT NO. : 6,184,212 B1
DATED : February 6, 2001
INVENTOR(S) : Miraglia et al.

It is certified that error appears in the above-identified patent and that said Letters Patent is hereby corrected as shown below:

Column 33,
Column 2, row 1 of Table 10, please delete "ATTCCCACCCTCACCCACCA" and insert -- ATTGGGAGGCTGAGGCAGGA --.
Column 2, row 2 of Table 10, please delete "CAACCTAATTCCCACCCTCA" and insert -- CAAGCTAATTGGGAGGCTGA --.
Column 2, row 3 of Table 10, please delete "ACCCCAACCTAATTCCCACC" and insert -- AGGCCAAGCTAATTGGGAGG --.
Column 2, row 4 of Table 10, please delete "ATCACTCTACCCCAACCTAA" and insert -- ATGACTGTAGGCCAAGCTAA --.
Column 2, row 5 of Table 10, please delete "CACATCACTCTACCCCAACC" and insert -- CAGATGACTGTAGGCCAAGC --.

Column 37,
Column 3, row 7 of Table 11, please delete "143" and insert -- 148 --.
Column 3, row 7 of Table 11, please delete "1S4" and insert -- 194 --.
Column 3, row 7 of Table 11, please delete "i94" and insert -- 194 --.

Signed and Sealed this

Eleventh Day of December, 2001

Attest:

NICHOLAS P. GODICI
Attesting Officer  Acting Director of the United States Patent and Trademark Office

SEQUENCE LISTING (1) GENERAL INFORMATION:

(iii) NUMBER OF SEQUENCES: 271

(2) INFORMATION FOR SEQ ID NO: 1:

(i) SEQUENCE CHARACTERISTICS:
      (A) LENGTH: 2372 base pairs
      (B) TYPE: Nucleic Acid
      (C) STRANDEDNESS: Single
      (D) TOPOLOGY: Unknown (iv) ANTI-SENSE: No (x) PUBLICATION INFORMATION:
      (A) AUTHORS: Oliner,J.D.
          Kinzler,K.W.
          Meltzer,P.S.
          George,D.L.
          Vogelstein,B.
      (B) TITLE: Amplification of a gene encoding a
          p53-associated protein in human sarcomas
      (C) JOURNAL: Nature
      (D) VOLUME: 358
      (E) ISSUE: 6381
      (F) PAGES: 80-83
      (G) DATE: 02-JUL-1992

(xi) SEQUENCE DESCRIPTION: SEQ ID NO: 1:

```
GCACCGCGCG AGCTTGGCTG CTTCTGGGGC CTGTGTGGCC CTGTGTGTCG           50

GAAAGATGGA GCAAGAAGCC GAGCCCGAGG GGCGGCCGCG ACCCCTCTGA          100

CCGAGATCCT GCTGCTTTCG CAGCCAGGAG CACCGTCCCT CCCCGGATTA          150

GTGCGTACGA GCGCCCAGTG CCCTGGCCCG GAGAGTGGAA TGATCCCCGA          200

GGCCCAGGGC GTCGTGCTTC CGCAGTAGTC AGTCCCCGTG AAGGAAACTG          250

GGGAGTCTTG AGGGACCCCC GACTCCAAGC GCGAAAACCC CGGATGGTGA          300

GGAGCAGGCA AATGTGCAAT ACCAACATGT CTGTACCTAC TGATGGTGCT          350

GTAACCACCT CACAGATTCC AGCTTCGGAA CAAGAGACCC TGGTTAGACC          400
```

```
AAAGCCATTG CTTTTGAAGT TATTAAAGTC TGTTGGTGCA CAAAAAGACA           450

CTTATACTAT GAAAGAGGTT CTTTTTTATC TTGGCCAGTA TATTATGACT           500

AAACGATTAT ATGATGAGAA GCAACAACAT ATTGTATATT GTTCAAATGA           550

TCTTCTAGGA GATTTGTTTG GCGTGCCAAG CTTCTCTGTG AAAGAGCACA           600

GGAAAATATA TACCATGATC TACAGGAACT TGGTAGTAGT CAATCAGCAG           650

GAATCATCGG ACTCAGGTAC ATCTGTGAGT GAGAACAGGT GTCACCTTGA           700

AGGTGGGAGT GATCAAAAGG ACCTTGTACA AGAGCTTCAG GAAGAGAAAC           750

CTTCATCTTC ACATTTGGTT TCTAGACCAT CTACCTCATC TAGAAGGAGA           800

GCAATTAGTG AGACAGAAGA AAATTCAGAT GAATTATCTG GTGAACGACA           850

AAGAAAACGC CACAAATCTG ATAGTATTTC CCTTTCCTTT GATGAAAGCC           900

TGGCTCTGTG TGTAATAAGG GAGATATGTT GTGAAAGAAG CAGTAGCAGT           950

GAATCTACAG GGACGCCATC GAATCCGGAT CTTGATGCTG GTGTAAGTGA          1000

ACATTCAGGT GATTGGTTGG ATCAGGATTC AGTTTCAGAT CAGTTTAGTG          1050

TAGAATTTGA AGTTGAATCT CTCGACTCAG AAGATTATAG CCTTAGTGAA          1100

GAAGGACAAG AACTCTCAGA TGAAGATGAT GAGGTATATC AAGTTACTGT          1150

GTATCAGGCA GGGGAGAGTG ATACAGATTC ATTTGAAGAA GATCCTGAAA          1200

TTTCCTTAGC TGACTATTGG AAATGCACTT CATGCAATGA AATGAATCCC          1250

CCCCTTCCAT CACATTGCAA CAGATGTTGG GCCCTTCGTG AGAATTGGCT          1300

TCCTGAAGAT AAAGGGAAAG ATAAAGGGGA AATCTCTGAG AAAGCCAAAC          1350

TGGAAAACTC AACACAAGCT GAAGAGGGCT TTGATGTTCC TGATTGTAAA          1400

AAAACTATAG TGAATGATTC CAGAGAGTCA TGTGTTGAGG AAAATGATGA          1450

TAAAATTACA CAAGCTTCAC AATCACAAGA AAGTGAAGAC TATTCTCAGC          1500

CATCAACTTC TAGTAGCATT ATTTATAGCA GCCAAGAAGA TGTGAAAGAG          1550

TTTGAAAGGG AAGAAACCCA AGACAAAGAA GAGAGTGTGG AATCTAGTTT          1600

GCCCCTTAAT GCCATTGAAC CTTGTGTGAT TTGTCAAGGT CGACCTAAAA          1650

ATGGTTGCAT TGTCCATGGC AAAACAGGAC ATCTTATGGC CTGCTTTACA          1700

TGTGCAAAGA AGCTAAAGAA AAGGAATAAG CCCTGCCCAG TATGTAGACA          1750

ACCAATTCAA ATGATTGTGC TAACTTATTT CCCCTAGTTG ACCTGTCTAT          1800

AAGAGAATTA TATATTTCTA ACTATATAAC CCTAGGAATT TAGACAACCT          1850

GAAATTTATT CACATATATC AAAGTGAGAA AATGCCTCAA TTCACATAGA          1900

TTTCTTCTCT TTAGTATAAT TGACCTACTT TGGTAGTGGA ATAGTGAATA          1950

CTTACTATAA TTTGACTTGA ATATGTAGCT CATCCTTTAC ACCAACTCCT          2000

AATTTTAAAT AATTTCTACT CTGTCTTAAA TGAGAAGTAC TTGGTTTTTT          2050

TTTTCTTAAA TATGTATATG ACATTTAAAT GTAACTTATT ATTTTTTTTG          2100

AGACCGAGTC TTGCTCTGTT ACCCAGGCTG GAGTGCAGTG GGTGATCTTG          2150

GCTCACTGCA AGCTCTGCCC TCCCCGGGTT CGCACCATTC TCCTGCCTCA          2200

GCCTCCCAAT TAGCTTGGCC TACAGTCATC TGCCACCACA CCTGGCTAAT          2250

TTTTTGTACT TTTAGTAGAG ACAGGGTTTC ACCGTGTTAG CCAGGATGGT          2300

CTCGATCTCC TGACCTCGTG ATCCGCCCAC CTCGGCCTCC CAAAGTGCTG          2350
```

```
GGATTACAGG CATGAGCCAC CG                                              2372
```

(2) INFORMATION FOR SEQ ID NO: 2:

(i) SEQUENCE CHARACTERISTICS:
        (A) LENGTH: 500 base pairs
        (B) TYPE: Nucleic Acid
        (C) STRANDEDNESS: Single
        (D) TOPOLOGY: Unknown (iv) ANTI-SENSE: No (x) PUBLICATION INFORMATION:
        (A) AUTHORS: Zauberman, A.
                Flusberg, D.
                Haupt, Y.
                Barak, Y.
                Oren, M.
        (B) TITLE: A functional p53-responsive intronic
            promoter is contained within the human mdm2 gene
        (C) JOURNAL: Nucleic Acids Res.
        (D) VOLUME: 23
        (E) ISSUE: 14
        (F) PAGES: 2584-2592
        (G) DATE: 25-JUL-1995

(xi) SEQUENCE DESCRIPTION: SEQ ID NO: 2:

```
GGCTGCGGGC CCCTGCGGCG CGGGAGGTCC GGATGATCGC AGGTGCCTGT      50

CGGGTCACTA GTGTGAACGC TGCGCGTAGT CTGGGCGGGA TTGGGCCGGT     100

TCAGTGGGCA GGTTGACTCA GCTTTTCCTC TTGAGCTGGT CAAGTTCAGA     150

CACGTTCCGA AACTGCAGTA AAAGGAGTTA AGTCCTGACT TGTCTCCAGC     200

TGGGGCTATT TAAACCATGC ATTTTCCCAG CTGTGTTCAG TGGCGATTGG     250

AGGGTAGACC TGTGGGCACG GACGCACGCC ACTTTTTCTC TGCTGATCCA     300

GGTAAGCACC GACTTGCTTG TAGCTTTAGT TTTAACTGTT GTTTATGTTC     350

TTTATATATG ATGTATTTTC CACAGATGTT TCATGATTTC CAGTTTTCAT     400

CGTGTCTTTT TTTTCCTTGT AGGCAAATGT GCAATACCAA CATGTCTGTA     450

CCTACTGATG GGGCTGTAAC CACCCCACAG ATTCCAGCTT CGGAACAAGA     500
```

(2) INFORMATION FOR SEQ ID NO: 3:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 3:

```
CAGCCAAGCT CGCGCGGTGC                                        20
```

(2) INFORMATION FOR SEQ ID NO: 4:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 4:

```
TCTTTCCGAC ACACAGGGCC                                        20
```

(2) INFORMATION FOR SEQ ID NO: 5:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 5:

CAGCAGGATC TCGGTCAGAG                                      20

(2) INFORMATION FOR SEQ ID NO: 6:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 6:

GGGCGCTCGT ACGCACTAAT                                      20

(2) INFORMATION FOR SEQ ID NO: 7:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 7:

TCGGGGATCA TTCCACTCTC                                      20

(2) INFORMATION FOR SEQ ID NO: 8:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 8:

CGGGGTTTTC GCGCTTGGAG                                      20

(2) INFORMATION FOR SEQ ID NO: 9:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 9:

CATTTGCCTG CTCCTCACCA                                      20

(2) INFORMATION FOR SEQ ID NO: 10:

(i) SEQUENCE CHARACTERISTICS:

(A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 10:

GTATTGCACA TTTGCCTGCT                                                   20

(2) INFORMATION FOR SEQ ID NO: 11:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 11:

AGCACCATCA GTAGGTACAG                                                   20

(2) INFORMATION FOR SEQ ID NO: 12:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 12:

CTACCAAGTT CCTGTAGATC                                                   20

(2) INFORMATION FOR SEQ ID NO: 13:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 13:

TCAACTTCAA ATTCTACACT                                                   20

(2) INFORMATION FOR SEQ ID NO: 14:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 14:

TTTACAATCA GGAACATCAA                                                   20

(2) INFORMATION FOR SEQ ID NO: 15:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 15:

AGCTTCTTTG CACATGTAAA                                         20

(2) INFORMATION FOR SEQ ID NO: 16:

(i) SEQUENCE CHARACTERISTICS:
            (A) LENGTH: 20 base pairs
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 16:

CAGGTCAACT AGGGGAAATA                                         20

(2) INFORMATION FOR SEQ ID NO: 17:

(i) SEQUENCE CHARACTERISTICS:
            (A) LENGTH: 20 base pairs
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 17:

TCTTATAGAC AGGTCAACTA                                         20

(2) INFORMATION FOR SEQ ID NO: 18:

(i) SEQUENCE CHARACTERISTICS:
            (A) LENGTH: 20 base pairs
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 18:

TCCTAGGGTT ATATAGTTAG                                         20

(2) INFORMATION FOR SEQ ID NO: 19:

(i) SEQUENCE CHARACTERISTICS:
            (A) LENGTH: 20 base pairs
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 19:

AAGTATTCAC TATTCCACTA                                         20

(2) INFORMATION FOR SEQ ID NO: 20:

(i) SEQUENCE CHARACTERISTICS:
            (A) LENGTH: 20 base pairs
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 20:

```
CCAAGATCAC CCACTGCACT                                                    20

(2) INFORMATION FOR SEQ ID NO: 21:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION:  SEQ ID NO: 21:

AGGTGTGGTG GCAGATGACT                                                    20

(2) INFORMATION FOR SEQ ID NO: 22:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION:  SEQ ID NO: 22:

CCTGTCTCTA CTAAAAGTAC                                                    20

(2) INFORMATION FOR SEQ ID NO: 23:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: No (xi) SEQUENCE DESCRIPTION:  SEQ ID NO: 23:

ACAAGCCTTC GCTCTACCGG                                                    20

(2) INFORMATION FOR SEQ ID NO: 24:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: No (xi) SEQUENCE DESCRIPTION:  SEQ ID NO: 24:

TTCAGCGCAT TTGTACATAA                                                    20

(2) INFORMATION FOR SEQ ID NO: 25:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION:  SEQ ID NO: 25:

TCTTTCCGAC ACACAGGGCC                                                    20
```

(2) INFORMATION FOR SEQ ID NO: 26:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: No (xi) SEQUENCE DESCRIPTION: SEQ ID NO: 26:

AGCTTCTTTA TACATGTAAA                                         20

(2) INFORMATION FOR SEQ ID NO: 27:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: No (xi) SEQUENCE DESCRIPTION: SEQ ID NO: 27:

AGCTTCTTTA CACATGTAAA                                         20

(2) INFORMATION FOR SEQ ID NO: 28:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 28:

CTACCCTCCA ATCGCCACTG                                         20

(2) INFORMATION FOR SEQ ID NO: 29:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 29:

GGTCTACCCT CCAATCGCCA                                       20

(2) INFORMATION FOR SEQ ID NO: 30:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 30:

CGTGCCCACA GGTCTACCCT                                       20

(2) INFORMATION FOR SEQ ID NO: 31:

(i) SEQUENCE CHARACTERISTICS:
        (A) LENGTH: 20 base pairs (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 31:

AAGTGGCGTG CGTCCGTGCC                                                  20

(2) INFORMATION FOR SEQ ID NO: 32:

(i) SEQUENCE CHARACTERISTICS:
            (A) LENGTH: 20 base pairs
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 32:

AAAGTGGCGT GCGTCCGTGC                                                  20

(2) INFORMATION FOR SEQ ID NO: 33:

(i) SEQUENCE CHARACTERISTICS:
            (A) LENGTH: 20 base pairs
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 33:

AAGCAGCCAA GCTCGCGCGG                                                  20

(2) INFORMATION FOR SEQ ID NO: 34:

(i) SEQUENCE CHARACTERISTICS:
            (A) LENGTH: 20 base pairs
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 34:

CAGGCCCCAG AAGCAGCCAA                                                  20

(2) INFORMATION FOR SEQ ID NO: 35:

(i) SEQUENCE CHARACTERISTICS:
            (A) LENGTH: 20 base pairs
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 35:

GCCACACAGG CCCCAGAAGC                                                  20

(2) INFORMATION FOR SEQ ID NO: 36:

(i) SEQUENCE CHARACTERISTICS:
            (A) LENGTH: 20 base pairs
            (B) TYPE: Nucleic Acid
            (C) STRANDEDNESS: Single
            (D) TOPOLOGY: Linear (iv) ANTI-SENSE: Yes (xi) SEQUENCE DESCRIPTION:  SEQ ID NO: 36:

ACACACAGGG CCACACAGGC                                                    20

(2) INFORMATION FOR SEQ ID NO: 37:

(i) SEQUENCE CHARACTERISTICS:
            (A) LENGTH: 20 base pairs
            (B) TYPE: Nucleic Acid
            (C) STRANDEDNESS: Single
            (D) TOPOLOGY: Linear (iv) ANTI-SENSE: Yes (xi) SEQUENCE DESCRIPTION:  SEQ ID NO: 37:

TTCCGACACA CAGGGCCACA                                                    20

(2) INFORMATION FOR SEQ ID NO: 38:

(i) SEQUENCE CHARACTERISTICS:
            (A) LENGTH: 20 base pairs
            (B) TYPE: Nucleic Acid
            (C) STRANDEDNESS: Single
            (D) TOPOLOGY: Linear (iv) ANTI-SENSE: Yes (xi) SEQUENCE DESCRIPTION:  SEQ ID NO: 38:

GCTCCATCTT TCCGACACAC                                                    20

(2) INFORMATION FOR SEQ ID NO: 39:

(i) SEQUENCE CHARACTERISTICS:
            (A) LENGTH: 20 base pairs
            (B) TYPE: Nucleic Acid
            (C) STRANDEDNESS: Single
            (D) TOPOLOGY: Linear (iv) ANTI-SENSE: Yes (xi) SEQUENCE DESCRIPTION:  SEQ ID NO: 39:

GCTTCTTGCT CCATCTTTCC                                                    20

(2) INFORMATION FOR SEQ ID NO: 40:

(i) SEQUENCE CHARACTERISTICS:
            (A) LENGTH: 20 base pairs
            (B) TYPE: Nucleic Acid
            (C) STRANDEDNESS: Single
            (D) TOPOLOGY: Linear (iv) ANTI-SENSE: Yes (xi) SEQUENCE DESCRIPTION:  SEQ ID NO: 40:

CCCTCGGGCT CGGCTTCTTG                                                    20

(2) INFORMATION FOR SEQ ID NO: 41:

(i) SEQUENCE CHARACTERISTICS:
            (A) LENGTH: 20 base pairs
            (B) TYPE: Nucleic Acid
            (C) STRANDEDNESS: Single
            (D) TOPOLOGY: Linear (iv) ANTI-SENSE: Yes (xi) SEQUENCE DESCRIPTION:  SEQ ID NO: 41:

GCGGCCGCCC CTCGGGCTCG                                                   20

(2) INFORMATION FOR SEQ ID NO: 42:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION:  SEQ ID NO: 42:

AAGCAGCAGG ATCTCGGTCA                                                   20

(2) INFORMATION FOR SEQ ID NO: 43:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION:  SEQ ID NO: 43:

GCTGCGAAAG CAGCAGGATC                                                   20

(2) INFORMATION FOR SEQ ID NO: 44:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION:  SEQ ID NO: 44:

TGCTCCTGGC TGCGAAAGCA                                                   20

(2) INFORMATION FOR SEQ ID NO: 45:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION:  SEQ ID NO: 45:

GGGACGGTGC TCCTGGCTGC                                                   20

(2) INFORMATION FOR SEQ ID NO: 46:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION:  SEQ ID NO: 46:

ACTGGGCGCT CGTACGCACT                                                   20

(2) INFORMATION FOR SEQ ID NO: 47:

(i) SEQUENCE CHARACTERISTICS:
    (A) LENGTH: 20 base pairs
    (B) TYPE: Nucleic Acid
    (C) STRANDEDNESS: Single
    (D) TOPOLOGY: Linear (iv) ANTI-SENSE: Yes (xi) SEQUENCE DESCRIPTION: SEQ ID NO: 47:

GCCAGGGCAC TGGGCGCTCG                                               20

(2) INFORMATION FOR SEQ ID NO: 48:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 48:

TCTCCGGGCC AGGGCACTGG                                               20

(2) INFORMATION FOR SEQ ID NO: 49:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 49:

TCATTCCACT CTCCGGGCCA                                               20

(2) INFORMATION FOR SEQ ID NO: 50:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 50:

GGAAGCACGA CGCCCTGGGC                                               20

(2) INFORMATION FOR SEQ ID NO: 51:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 51:

TACTGCGGAA GCACGACGCC                                               20

(2) INFORMATION FOR SEQ ID NO: 52:

(i) SEQUENCE CHARACTERISTICS:
        (A) LENGTH: 20 base pairs
        (B) TYPE: Nucleic Acid (C) STRANDEDNESS: Single
            (D) TOPOLOGY: Linear (iv) ANTI-SENSE: Yes (xi) SEQUENCE DESCRIPTION: SEQ ID NO: 52:

GGGACTGACT ACTGCGGAAG                                            20

(2) INFORMATION FOR SEQ ID NO: 53:

(i) SEQUENCE CHARACTERISTICS:
            (A) LENGTH: 20 base pairs
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 53:

TCAAGACTCC CCAGTTTCCT                                            20

(2) INFORMATION FOR SEQ ID NO: 54:

(i) SEQUENCE CHARACTERISTICS:
            (A) LENGTH: 20 base pairs
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 54:

CCTGCTCCTC ACCATCCGGG                                            20

(2) INFORMATION FOR SEQ ID NO: 55:

(i) SEQUENCE CHARACTERISTICS:
            (A) LENGTH: 20 base pairs
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 55:

TTTGCCTGCT CCTCACCATC                                            20

(2) INFORMATION FOR SEQ ID NO: 56:

(i) SEQUENCE CHARACTERISTICS:
            (A) LENGTH: 20 base pairs
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 56:

ATTTGCCTGC TCCTCACCAT                                            20

(2) INFORMATION FOR SEQ ID NO: 57:

(i) SEQUENCE CHARACTERISTICS:
            (A) LENGTH: 20 base pairs
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 57:

ACATTTGCCT GCTCCTCACC                                                        20

(2) INFORMATION FOR SEQ ID NO: 58:

(i) SEQUENCE CHARACTERISTICS:
            (A) LENGTH: 20 base pairs
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 58:

CACATTTGCC TGCTCCTCAC                                                        20

(2) INFORMATION FOR SEQ ID NO: 59:

(i) SEQUENCE CHARACTERISTICS:
            (A) LENGTH: 20 base pairs
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 59:

GCACATTTGC CTGCTCCTCA                                                        20

(2) INFORMATION FOR SEQ ID NO: 60:

(i) SEQUENCE CHARACTERISTICS:
            (A) LENGTH: 20 base pairs
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 60:

TGCACATTTG CCTGCTCCTC                                                        20

(2) INFORMATION FOR SEQ ID NO: 61:

(i) SEQUENCE CHARACTERISTICS:
            (A) LENGTH: 20 base pairs
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 61:

TTGCACATTT GCCTGCTCCT                                                        20

(2) INFORMATION FOR SEQ ID NO: 62:

(i) SEQUENCE CHARACTERISTICS:
            (A) LENGTH: 20 base pairs
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 62:

ATTGCACATT TGCCTGCTCC                                                        20

(2) INFORMATION FOR SEQ ID NO: 63:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 63:

TATTGCACAT TTGCCTGCTC                                               20

(2) INFORMATION FOR SEQ ID NO: 64:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 64:

GGTATTGCAC ATTTGCCTGC                                               20

(2) INFORMATION FOR SEQ ID NO: 65:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 65:

TGGTATTGCA CATTTGCCTG                                               20

(2) INFORMATION FOR SEQ ID NO: 66:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 66:

TTGGTATTGC ACATTTGCCT                                               20

(2) INFORMATION FOR SEQ ID NO: 67:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 67:

GTTGGTATTG CACATTTGCC                                               20

(2) INFORMATION FOR SEQ ID NO: 68:

(i) SEQUENCE CHARACTERISTICS:
    (A) LENGTH: 20 base pairs
    (B) TYPE: Nucleic Acid
    (C) STRANDEDNESS: Single
    (D) TOPOLOGY: Linear (iv) ANTI-SENSE: Yes (xi) SEQUENCE DESCRIPTION: SEQ ID NO: 68:

TGTTGGTATT GCACATTTGC                                           20

(2) INFORMATION FOR SEQ ID NO: 69:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 69:

ATGTTGGTAT TGCACATTTG                                           20

(2) INFORMATION FOR SEQ ID NO: 70:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 70:

CATGTTGGTA TTGCACATTT                                           20

(2) INFORMATION FOR SEQ ID NO: 71:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 71:

ACATGTTGGT ATTGCACATT                                           20

(2) INFORMATION FOR SEQ ID NO: 72:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 72:

GACATGTTGG TATTGCACAT                                           20

(2) INFORMATION FOR SEQ ID NO: 73:

(i) SEQUENCE CHARACTERISTICS:
        (A) LENGTH: 20 base pairs
        (B) TYPE: Nucleic Acid
        (C) STRANDEDNESS: Single (D) TOPOLOGY: Linear (iv) ANTI-SENSE: Yes (xi) SEQUENCE DESCRIPTION:  SEQ ID NO: 73:

AGACATGTTG GTATTGCACA                                                          20

(2) INFORMATION FOR SEQ ID NO: 74:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION:  SEQ ID NO: 74:

CAGACATGTT GGTATTGCAC                                                          20

(2) INFORMATION FOR SEQ ID NO: 75:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION:  SEQ ID NO: 75:

CAGTAGGTAC AGACATGTTG                                                          20

(2) INFORMATION FOR SEQ ID NO: 76:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION:  SEQ ID NO: 76:

TACAGCACCA TCAGTAGGTA                                                          20

(2) INFORMATION FOR SEQ ID NO: 77:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION:  SEQ ID NO: 77:

GGAATCTGTG AGGTGGTTAC                                                          20

(2) INFORMATION FOR SEQ ID NO: 78:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 78:

TTCCGAAGCT GGAATCTGTG                                    20

(2) INFORMATION FOR SEQ ID NO: 79:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 79:

AGGGTCTCTT GTTCCGAAGC                                    20

(2) INFORMATION FOR SEQ ID NO: 80:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 80:

GCTTTGGTCT AACCAGGGTC                                    20

(2) INFORMATION FOR SEQ ID NO: 81:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 81:

GCAATGGCTT TGGTCTAACC                                    20

(2) INFORMATION FOR SEQ ID NO: 82:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 82:

TAACTTCAAA AGCAATGGCT                                    20

(2) INFORMATION FOR SEQ ID NO: 83:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 83:

GTGCACCAAC AGACTTTAAT                                    20

(2) INFORMATION FOR SEQ ID NO: 84:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 84:

ACCTCTTTCA TAGTATAAGT                                        20

(2) INFORMATION FOR SEQ ID NO: 85:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 85:

ATAATATACT GGCCAAGATA                                        20

(2) INFORMATION FOR SEQ ID NO: 86:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 86:

TAATCGTTTA GTCATAATAT                                        20

(2) INFORMATION FOR SEQ ID NO: 87:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 87:

ATCATATAAT CGTTTAGTCA                                        20

(2) INFORMATION FOR SEQ ID NO: 88:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 88:

GCTTCTCATC ATATAATCGT                                        20

(2) INFORMATION FOR SEQ ID NO: 89:

(i) SEQUENCE CHARACTERISTICS:

(A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 89:

CAATATGTTG TTGCTTCTCA                                       20

(2) INFORMATION FOR SEQ ID NO: 90:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 90:

GAACAATATA CAATATGTTG                                       20

(2) INFORMATION FOR SEQ ID NO: 91:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 91:

TCATTTGAAC AATATACAAT                                       20

(2) INFORMATION FOR SEQ ID NO: 92:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 92:

TAGAAGATCA TTTGAACAAT                                       20

(2) INFORMATION FOR SEQ ID NO: 93:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 93:

AACAAATCTC CTAGAAGATC                                       20

(2) INFORMATION FOR SEQ ID NO: 94:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 94:

TGGCACGCCA AACAAATCTC                                                           20

(2) INFORMATION FOR SEQ ID NO: 95:

(i) SEQUENCE CHARACTERISTICS:
            (A) LENGTH: 20 base pairs
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 95:

AGAAGCTTGG CACGCCAAAC                                                           20

(2) INFORMATION FOR SEQ ID NO: 96:

(i) SEQUENCE CHARACTERISTICS:
            (A) LENGTH: 20 base pairs
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 96:

CTTTCACAGA GAAGCTTGGC                                                           20

(2) INFORMATION FOR SEQ ID NO: 97:

(i) SEQUENCE CHARACTERISTICS:
            (A) LENGTH: 20 base pairs
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 97:

TTTTCCTGTG CTCTTTCACA                                                           20

(2) INFORMATION FOR SEQ ID NO: 98:

(i) SEQUENCE CHARACTERISTICS:
            (A) LENGTH: 20 base pairs
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 98:

TATATATTTT CCTGTGCTCT                                                           20

(2) INFORMATION FOR SEQ ID NO: 99:

(i) SEQUENCE CHARACTERISTICS:
            (A) LENGTH: 20 base pairs
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 99:

ATCATGGTAT ATATTTTCCT                                                    20

(2) INFORMATION FOR SEQ ID NO: 100:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 100:

TTCCTGTAGA TCATGGTATA                                                    20

(2) INFORMATION FOR SEQ ID NO: 101:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 101:

TACTACCAAG TTCCTGTAGA                                                    20

(2) INFORMATION FOR SEQ ID NO: 102:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 102:

TTCCTGCTGA TTGACTACTA                                                    20

(2) INFORMATION FOR SEQ ID NO: 103:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 103:

TGAGTCCGAT GATTCCTGCT                                                    20

(2) INFORMATION FOR SEQ ID NO: 104:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 104:

CAGATGTACC TGAGTCCGAT                                                    20

(2) INFORMATION FOR SEQ ID NO: 105:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 105:

CTGTTCTCAC TCACAGATGT                                         20

(2) INFORMATION FOR SEQ ID NO: 106:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 106:

TTCAAGGTGA CACCTGTTCT                                         20

(2) INFORMATION FOR SEQ ID NO: 107:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 107:

ACTCCCACCT TCAAGGTGAC                                         20

(2) INFORMATION FOR SEQ ID NO: 108:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 108:

GGTCCTTTTG ATCACTCCCA                                         20

(2) INFORMATION FOR SEQ ID NO: 109:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 109:

AAGCTCTTGT ACAAGGTCCT                                         20

(2) INFORMATION FOR SEQ ID NO: 110:

(i) SEQUENCE CHARACTERISTICS:
        (A) LENGTH: 20 base pairs (B) TYPE: Nucleic Acid
           (C) STRANDEDNESS: Single
           (D) TOPOLOGY: Linear (iv) ANTI-SENSE: Yes (xi) SEQUENCE DESCRIPTION: SEQ ID NO: 110:

CTCTTCCTGA AGCTCTTGTA                                              20

(2) INFORMATION FOR SEQ ID NO: 111:

(i) SEQUENCE CHARACTERISTICS:
           (A) LENGTH: 20 base pairs
           (B) TYPE: Nucleic Acid
           (C) STRANDEDNESS: Single
           (D) TOPOLOGY: Linear (iv) ANTI-SENSE: Yes (xi) SEQUENCE DESCRIPTION: SEQ ID NO: 111:

AAGATGAAGG TTTCTCTTCC                                              20

(2) INFORMATION FOR SEQ ID NO: 112:

(i) SEQUENCE CHARACTERISTICS:
           (A) LENGTH: 20 base pairs
           (B) TYPE: Nucleic Acid
           (C) STRANDEDNESS: Single
           (D) TOPOLOGY: Linear (iv) ANTI-SENSE: Yes (xi) SEQUENCE DESCRIPTION: SEQ ID NO: 112:

AAACCAAATG TGAAGATGAA                                              20

(2) INFORMATION FOR SEQ ID NO: 113:

(i) SEQUENCE CHARACTERISTICS:
           (A) LENGTH: 20 base pairs
           (B) TYPE: Nucleic Acid
           (C) STRANDEDNESS: Single
           (D) TOPOLOGY: Linear (iv) ANTI-SENSE: Yes (xi) SEQUENCE DESCRIPTION: SEQ ID NO: 113:

ATGGTCTAGA AACCAAATGT                                              20

(2) INFORMATION FOR SEQ ID NO: 114:

(i) SEQUENCE CHARACTERISTICS:
           (A) LENGTH: 20 base pairs
           (B) TYPE: Nucleic Acid
           (C) STRANDEDNESS: Single
           (D) TOPOLOGY: Linear (iv) ANTI-SENSE: Yes (xi) SEQUENCE DESCRIPTION: SEQ ID NO: 114:

CTAGATGAGG TAGATGGTCT                                              20

(2) INFORMATION FOR SEQ ID NO: 115:

(i) SEQUENCE CHARACTERISTICS:
           (A) LENGTH: 20 base pairs
           (B) TYPE: Nucleic Acid
           (C) STRANDEDNESS: Single
           (D) TOPOLOGY: Linear (iv) ANTI-SENSE: Yes (xi) SEQUENCE DESCRIPTION: SEQ ID NO: 115:

AATTGCTCTC CTTCTAGATG                    20

(2) INFORMATION FOR SEQ ID NO: 116:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 116:

TCTGTCTCAC TAATTGCTCT                    20

(2) INFORMATION FOR SEQ ID NO: 117:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 117:

TCTGAATTTT CTTCTGTCTC                    20

(2) INFORMATION FOR SEQ ID NO: 118:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 118:

CACCAGATAA TTCATCTGAA                    20

(2) INFORMATION FOR SEQ ID NO: 119:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 119:

TTTGTCGTTC ACCAGATAAT                    20

(2) INFORMATION FOR SEQ ID NO: 120:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 120:

```
GTGGCGTTTT CTTTGTCGTT                                                    20

(2) INFORMATION FOR SEQ ID NO: 121:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION:   SEQ ID NO: 121:

TACTATCAGA TTTGTGGCGT                                                    20

(2) INFORMATION FOR SEQ ID NO: 122:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION:   SEQ ID NO: 122:

GAAAGGGAAA TACTATCAGA                                                    20

(2) INFORMATION FOR SEQ ID NO: 123:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION:   SEQ ID NO: 123:

GCTTTCATCA AAGGAAAGGG                                                    20

(2) INFORMATION FOR SEQ ID NO: 124:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION:   SEQ ID NO: 124:

TACACACAGA GCCAGGCTTT                                                    20

(2) INFORMATION FOR SEQ ID NO: 125:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION:   SEQ ID NO: 125:

CTCCCTTATT ACACACAGAG                                                    20

(2) INFORMATION FOR SEQ ID NO: 126:
```

(i) SEQUENCE CHARACTERISTICS:
            (A) LENGTH: 20 base pairs
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 126:

TCACAACATA TCTCCCTTAT                                                    20

(2) INFORMATION FOR SEQ ID NO: 127:

(i) SEQUENCE CHARACTERISTICS:
            (A) LENGTH: 20 base pairs
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 127:

CTACTGCTTC TTTCACAACA                                                    20

(2) INFORMATION FOR SEQ ID NO: 128:

(i) SEQUENCE CHARACTERISTICS:
            (A) LENGTH: 20 base pairs
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 128:

GATTCACTGC TACTGCTTCT                                                    20

(2) INFORMATION FOR SEQ ID NO: 129:

(i) SEQUENCE CHARACTERISTICS:
            (A) LENGTH: 20 base pairs
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 129:

TGGCGTCCCT GTAGATTCAC                                                    20

(2) INFORMATION FOR SEQ ID NO: 130:

(i) SEQUENCE CHARACTERISTICS:
            (A) LENGTH: 20 base pairs
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 130:

AAGATCCGGA TTCGATGGCG                                                    20

(2) INFORMATION FOR SEQ ID NO: 131:

(i) SEQUENCE CHARACTERISTICS:
            (A) LENGTH: 20 base pairs
            (B) TYPE: Nucleic Acid (C) STRANDEDNESS: Single
          (D) TOPOLOGY: Linear (iv) ANTI-SENSE: Yes (xi) SEQUENCE DESCRIPTION: SEQ ID NO: 131:

CAGCATCAAG ATCCGGATTC                                             20

(2) INFORMATION FOR SEQ ID NO: 132:

(i) SEQUENCE CHARACTERISTICS:
          (A) LENGTH: 20 base pairs
          (B) TYPE: Nucleic Acid
          (C) STRANDEDNESS: Single
          (D) TOPOLOGY: Linear (iv) ANTI-SENSE: Yes (xi) SEQUENCE DESCRIPTION: SEQ ID NO: 132:

GTTCACTTAC ACCAGCATCA                                             20

(2) INFORMATION FOR SEQ ID NO: 133:

(i) SEQUENCE CHARACTERISTICS:
          (A) LENGTH: 20 base pairs
          (B) TYPE: Nucleic Acid
          (C) STRANDEDNESS: Single
          (D) TOPOLOGY: Linear (iv) ANTI-SENSE: Yes (xi) SEQUENCE DESCRIPTION: SEQ ID NO: 133:

CAATCACCTG AATGTTCACT                                             20

(2) INFORMATION FOR SEQ ID NO: 134:

(i) SEQUENCE CHARACTERISTICS:
          (A) LENGTH: 20 base pairs
          (B) TYPE: Nucleic Acid
          (C) STRANDEDNESS: Single
          (D) TOPOLOGY: Linear (iv) ANTI-SENSE: Yes (xi) SEQUENCE DESCRIPTION: SEQ ID NO: 134:

CTGATCCAAC CAATCACCTG                                             20

(2) INFORMATION FOR SEQ ID NO: 135:

(i) SEQUENCE CHARACTERISTICS:
          (A) LENGTH: 20 base pairs
          (B) TYPE: Nucleic Acid
          (C) STRANDEDNESS: Single
          (D) TOPOLOGY: Linear (iv) ANTI-SENSE: Yes (xi) SEQUENCE DESCRIPTION: SEQ ID NO: 135:

GAAACTGAAT CCTGATCCAA                                             20

(2) INFORMATION FOR SEQ ID NO: 136:

(i) SEQUENCE CHARACTERISTICS:
          (A) LENGTH: 20 base pairs
          (B) TYPE: Nucleic Acid
          (C) STRANDEDNESS: Single
          (D) TOPOLOGY: Linear (iv) ANTI-SENSE: Yes (xi) SEQUENCE DESCRIPTION: SEQ ID NO: 136:

TGATCTGAAA CTGAATCCTG                                                    20

(2) INFORMATION FOR SEQ ID NO: 137:

(i) SEQUENCE CHARACTERISTICS:
         (A) LENGTH: 20 base pairs
         (B) TYPE: Nucleic Acid
         (C) STRANDEDNESS: Single
         (D) TOPOLOGY: Linear (iv) ANTI-SENSE: Yes (xi) SEQUENCE DESCRIPTION: SEQ ID NO: 137:

CTACACTAAA CTGATCTGAA                                                    20

(2) INFORMATION FOR SEQ ID NO: 138:

(i) SEQUENCE CHARACTERISTICS:
         (A) LENGTH: 20 base pairs
         (B) TYPE: Nucleic Acid
         (C) STRANDEDNESS: Single
         (D) TOPOLOGY: Linear (iv) ANTI-SENSE: Yes (xi) SEQUENCE DESCRIPTION: SEQ ID NO: 138:

CAACTTCAAA TTCTACACTA                                                    20

(2) INFORMATION FOR SEQ ID NO: 139:

(i) SEQUENCE CHARACTERISTICS:
         (A) LENGTH: 20 base pairs
         (B) TYPE: Nucleic Acid
         (C) STRANDEDNESS: Single
         (D) TOPOLOGY: Linear (iv) ANTI-SENSE: Yes (xi) SEQUENCE DESCRIPTION: SEQ ID NO: 139:

AGATTCAACT TCAAATTCTA                                                    20

(2) INFORMATION FOR SEQ ID NO: 140:

(i) SEQUENCE CHARACTERISTICS:
         (A) LENGTH: 20 base pairs
         (B) TYPE: Nucleic Acid
         (C) STRANDEDNESS: Single
         (D) TOPOLOGY: Linear (iv) ANTI-SENSE: Yes (xi) SEQUENCE DESCRIPTION: SEQ ID NO: 140:

GAGTCGAGAG ATTCAACTTC                                                    20

(2) INFORMATION FOR SEQ ID NO: 141:

(i) SEQUENCE CHARACTERISTICS:
         (A) LENGTH: 20 base pairs
         (B) TYPE: Nucleic Acid
         (C) STRANDEDNESS: Single
         (D) TOPOLOGY: Linear (iv) ANTI-SENSE: Yes (xi) SEQUENCE DESCRIPTION: SEQ ID NO: 141:

TAATCTTCTG AGTCGAGAGA                                                    20

(2) INFORMATION FOR SEQ ID NO: 142:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 142:

CTAAGGCTAT AATCTTCTGA                                           20

(2) INFORMATION FOR SEQ ID NO: 143:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 143:

TTCTTCACTA AGGCTATAAT                                           20

(2) INFORMATION FOR SEQ ID NO: 144:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 144:

TCTTGTCCTT CTTCACTAAG                                           20

(2) INFORMATION FOR SEQ ID NO: 145:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 145:

CTGAGAGTTC TTGTCCTTCT                                           20

(2) INFORMATION FOR SEQ ID NO: 146:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 146:

TTCATCTGAG AGTTCTTGTC                                           20

(2) INFORMATION FOR SEQ ID NO: 147:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 147:

CCTCATCATC TTCATCTGAG                                               20

(2) INFORMATION FOR SEQ ID NO: 148:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 148:

CTTGATATAC CTCATCATCT                                               20

(2) INFORMATION FOR SEQ ID NO: 149:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 149:

ATACACAGTA ACTTGATATA                                               20

(2) INFORMATION FOR SEQ ID NO: 150:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 150:

CTCTCCCCTG CCTGATACAC                                               20

(2) INFORMATION FOR SEQ ID NO: 151:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 151:

GAATCTGTAT CACTCTCCCC                                               20

(2) INFORMATION FOR SEQ ID NO: 152:

(i) SEQUENCE CHARACTERISTICS:
        (A) LENGTH: 20 base pairs
        (B) TYPE: Nucleic Acid
        (C) STRANDEDNESS: Single (D) TOPOLOGY: Linear (iv) ANTI-SENSE: Yes (xi) SEQUENCE DESCRIPTION: SEQ ID NO: 152:

TCTTCAAATG AATCTGTATC                                                    20

(2) INFORMATION FOR SEQ ID NO: 153:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 153:

AAATTTCAGG ATCTTCTTCA                                                    20

(2) INFORMATION FOR SEQ ID NO: 154:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 154:

AGTCAGCTAA GGAAATTTCA                                                    20

(2) INFORMATION FOR SEQ ID NO: 155:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 155:

GCATTTCCAA TAGTCAGCTA                                                    20

(2) INFORMATION FOR SEQ ID NO: 156:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 156:

CATTGCATGA AGTGCATTTC                                                    20

(2) INFORMATION FOR SEQ ID NO: 157:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 157:

TCATTTCATT GCATGAAGTG                                           20

(2) INFORMATION FOR SEQ ID NO: 158:

(i) SEQUENCE CHARACTERISTICS:
            (A) LENGTH: 20 base pairs
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 158:

CATCTGTTGC AATGTGATGG                                           20

(2) INFORMATION FOR SEQ ID NO: 159:

(i) SEQUENCE CHARACTERISTICS:
            (A) LENGTH: 20 base pairs
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 159:

GAAGGGCCCA ACATCTGTTG                                           20

(2) INFORMATION FOR SEQ ID NO: 160:

(i) SEQUENCE CHARACTERISTICS:
            (A) LENGTH: 20 base pairs
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 160:

TTCTCACGAA GGGCCCAACA                                           20

(2) INFORMATION FOR SEQ ID NO: 161:

(i) SEQUENCE CHARACTERISTICS:
            (A) LENGTH: 20 base pairs
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 161:

GAAGCCAATT CTCACGAAGG                                           20

(2) INFORMATION FOR SEQ ID NO: 162:

(i) SEQUENCE CHARACTERISTICS:
            (A) LENGTH: 20 base pairs
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 162:

TATCTTCAGG AAGCCAATTC                                           20

(2) INFORMATION FOR SEQ ID NO: 163:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 163:

CTTTCCCTTT ATCTTCAGGA                                          20

(2) INFORMATION FOR SEQ ID NO: 164:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 164:

TCCCCTTTAT CTTTCCCTTT                                          20

(2) INFORMATION FOR SEQ ID NO: 165:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 165:

CTTTCTCAGA GATTTCCCCT                                          20

(2) INFORMATION FOR SEQ ID NO: 166:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 166:

CAGTTTGGCT TTCTCAGAGA                                          20

(2) INFORMATION FOR SEQ ID NO: 167:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 167:

GTGTTGAGTT TTCCAGTTTG                                          20

(2) INFORMATION FOR SEQ ID NO: 168:

(i) SEQUENCE CHARACTERISTICS:

(A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 168:

CCTCTTCAGC TTGTGTTGAG                                               20

(2) INFORMATION FOR SEQ ID NO: 169:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 169:

ACATCAAAGC CCTCTTCAGC                                               20

(2) INFORMATION FOR SEQ ID NO: 170:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 170:

GAATCATTCA CTATAGTTTT                                               20

(2) INFORMATION FOR SEQ ID NO: 171:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 171:

ATGACTCTCT GGAATCATTC                                               20

(2) INFORMATION FOR SEQ ID NO: 172:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 172:

CCTCAACACA TGACTCTCTG                                               20

(2) INFORMATION FOR SEQ ID NO: 173:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 173:

TTATCATCAT TTTCCTCAAC                                                                   20

(2) INFORMATION FOR SEQ ID NO: 174:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 174:

TAATTTTATC ATCATTTTCC                                                                   20

(2) INFORMATION FOR SEQ ID NO: 175:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 175:

GAAGCTTGTG TAATTTTATC                                                                   20

(2) INFORMATION FOR SEQ ID NO: 176:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 176:

TGATTGTGAA GCTTGTGTAA                                                                   20

(2) INFORMATION FOR SEQ ID NO: 177:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 177:

CACTTTCTTG TGATTGTGAA                                                                   20

(2) INFORMATION FOR SEQ ID NO: 178:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 178:

```
GCTGAGAATA GTCTTCACTT                                                    20

(2) INFORMATION FOR SEQ ID NO: 179:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION:  SEQ ID NO: 179:

AGTTGATGGC TGAGAATAGT                                                    20

(2) INFORMATION FOR SEQ ID NO: 180:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION:  SEQ ID NO: 180:

TGCTACTAGA AGTTGATGGC                                                    20

(2) INFORMATION FOR SEQ ID NO: 181:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION:  SEQ ID NO: 181:

TAAATAATGC TACTAGAAGT                                                    20

(2) INFORMATION FOR SEQ ID NO: 182:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION:  SEQ ID NO: 182:

CTTGGCTGCT ATAAATAATG                                                    20

(2) INFORMATION FOR SEQ ID NO: 183:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION:  SEQ ID NO: 183:

ATCTTCTTGG CTGCTATAAA                                                    20
```

(2) INFORMATION FOR SEQ ID NO: 184:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 184:

AACTCTTTCA CATCTTCTTG                                      20

(2) INFORMATION FOR SEQ ID NO: 185:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 185:

CCCTTTCAAA CTCTTTCACA                                      20

(2) INFORMATION FOR SEQ ID NO: 186:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 186:

GGGTTTCTTC CCTTTCAAAC                                      20

(2) INFORMATION FOR SEQ ID NO: 187:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 187:

TCTTTGTCTT GGGTTTCTTC                                      20

(2) INFORMATION FOR SEQ ID NO: 188:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 188:

CTCTCTTCTT TGTCTTGGGT                                      20

(2) INFORMATION FOR SEQ ID NO: 189:

(i) SEQUENCE CHARACTERISTICS:
        (A) LENGTH: 20 base pairs (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 189:

AACTAGATTC CACACTCTCT                                                    20

(2) INFORMATION FOR SEQ ID NO: 190:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 190:

CAAGGTTCAA TGGCATTAAG                                                    20

(2) INFORMATION FOR SEQ ID NO: 191:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 191:

TGACAAATCA CACAAGGTTC                                                    20

(2) INFORMATION FOR SEQ ID NO: 192:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 192:

TCGACCTTGA CAAATCACAC                                                    20

(2) INFORMATION FOR SEQ ID NO: 193:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 193:

ATGGACAATG CAACCATTTT                                                    20

(2) INFORMATION FOR SEQ ID NO: 194:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 194:

TGTTTTGCCA TGGACAATGC                                              20

(2) INFORMATION FOR SEQ ID NO: 195:

(i) SEQUENCE CHARACTERISTICS:
            (A) LENGTH: 20 base pairs
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 195:

TAAGATGTCC TGTTTTGCCA                                              20

(2) INFORMATION FOR SEQ ID NO: 196:

(i) SEQUENCE CHARACTERISTICS:
            (A) LENGTH: 20 base pairs
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 196:

GCAGGCCATA AGATGTCCTG                                              20

(2) INFORMATION FOR SEQ ID NO: 197:

(i) SEQUENCE CHARACTERISTICS:
            (A) LENGTH: 20 base pairs
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 197:

ACATGTAAAG CAGGCCATAA                                              20

(2) INFORMATION FOR SEQ ID NO: 198:

(i) SEQUENCE CHARACTERISTICS:
            (A) LENGTH: 20 base pairs
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 198:

CTTTGCACAT GTAAAGCAGG                                              20

(2) INFORMATION FOR SEQ ID NO: 199:

(i) SEQUENCE CHARACTERISTICS:
            (A) LENGTH: 20 base pairs
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 199:

TTTCTTTAGC TTCTTTGCAC                                              20

(2) INFORMATION FOR SEQ ID NO: 200:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 200:

TTATTCCTTT TCTTTAGCTT                                              20

(2) INFORMATION FOR SEQ ID NO: 201:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 201:

TGGGCAGGGC TTATTCCTTT                                              20

(2) INFORMATION FOR SEQ ID NO: 202:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 202:

ACATACTGGG CAGGGCTTAT                                              20

(2) INFORMATION FOR SEQ ID NO: 203:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 203:

TTGGTTGTCT ACATACTGGG                                              20

(2) INFORMATION FOR SEQ ID NO: 204:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 204:

TCATTTGAAT TGGTTGTCTA                                              20

(2) INFORMATION FOR SEQ ID NO: 205:

(i) SEQUENCE CHARACTERISTICS:
    (A) LENGTH: 20 base pairs
    (B) TYPE: Nucleic Acid
    (C) STRANDEDNESS: Single
    (D) TOPOLOGY: Linear (iv) ANTI-SENSE: Yes (xi) SEQUENCE DESCRIPTION: SEQ ID NO: 205:

AAGTTAGCAC AATCATTTGA                                               20

(2) INFORMATION FOR SEQ ID NO: 206:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 206:

TCTCTTATAG ACAGGTCAAC                                               20

(2) INFORMATION FOR SEQ ID NO: 207:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 207:

AAATATATAA TTCTCTTATA                                               20

(2) INFORMATION FOR SEQ ID NO: 208:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 208:

AGTTAGAAAT ATATAATTCT                                               20

(2) INFORMATION FOR SEQ ID NO: 209:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 209:

ATATAGTTAG AAATATATAA                                               20

(2) INFORMATION FOR SEQ ID NO: 210:

(i) SEQUENCE CHARACTERISTICS:
        (A) LENGTH: 20 base pairs
        (B) TYPE: Nucleic Acid

```
        (C) STRANDEDNESS: Single
        (D) TOPOLOGY: Linear (iv) ANTI-SENSE: Yes (xi) SEQUENCE DESCRIPTION: SEQ ID NO: 210:

CTAGGGTTAT ATAGTTAGAA                                               20

(2) INFORMATION FOR SEQ ID NO: 211:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 211:

TAAATTCCTA GGGTTATATA                                               20

(2) INFORMATION FOR SEQ ID NO: 212:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 212:

CAGGTTGTCT AAATTCCTAG                                               20

(2) INFORMATION FOR SEQ ID NO: 213:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 213:

ATAAATTTCA GGTTGTCTAA                                               20

(2) INFORMATION FOR SEQ ID NO: 214:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 214:

ATATATGTGA ATAAATTTCA                                               20

(2) INFORMATION FOR SEQ ID NO: 215:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes
```

(xi) SEQUENCE DESCRIPTION: SEQ ID NO: 215:

CTTTGATATA TGTGAATAAA                                              20

(2) INFORMATION FOR SEQ ID NO: 216:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 216:

CATTTTCTCA CTTTGATATA                                              20

(2) INFORMATION FOR SEQ ID NO: 217:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 217:

ATTGAGGCAT TTTCTCACTT                                              20

(2) INFORMATION FOR SEQ ID NO: 218:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 218:

AATCTATGTG AATTGAGGCA                                              20

(2) INFORMATION FOR SEQ ID NO: 219:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 219:

AGAAGAAATC TATGTGAATT                                              20

(2) INFORMATION FOR SEQ ID NO: 220:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 220:

ATACTAAAGA GAAGAAATCT                                              20

(2) INFORMATION FOR SEQ ID NO: 221:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 221:

GTCAATTATA CTAAAGAGAA                                           20

(2) INFORMATION FOR SEQ ID NO: 222:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 222:

TAGGTCAATT ATACTAAAGA                                           20

(2) INFORMATION FOR SEQ ID NO: 223:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 223:

CAAAGTAGGT CAATTATACT                                           20

(2) INFORMATION FOR SEQ ID NO: 224:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 224:

CCACTACCAA AGTAGGTCAA                                           20

(2) INFORMATION FOR SEQ ID NO: 225:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 225:

AGTATTCACT ATTCCACTAC                                           20

(2) INFORMATION FOR SEQ ID NO: 226:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION:  SEQ ID NO: 226:

TATAGTAAGT ATTCACTATT                                             20

(2) INFORMATION FOR SEQ ID NO: 227:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION:  SEQ ID NO: 227:

AGTCAAATTA TAGTAAGTAT                                             20

(2) INFORMATION FOR SEQ ID NO: 228:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION:  SEQ ID NO: 228:

CATATTCAAG TCAAATTATA                                             20

(2) INFORMATION FOR SEQ ID NO: 229:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION:  SEQ ID NO: 229:

AAAGGATGAG CTACATATTC                                             20

(2) INFORMATION FOR SEQ ID NO: 230:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION:  SEQ ID NO: 230:

GTGTAAAGGA TGAGCTACAT                                             20

(2) INFORMATION FOR SEQ ID NO: 231:

(i) SEQUENCE CHARACTERISTICS:
        (A) LENGTH: 20 base pairs
        (B) TYPE: Nucleic Acid
        (C) STRANDEDNESS: Single (D) TOPOLOGY: Linear (iv) ANTI-SENSE: Yes (xi) SEQUENCE DESCRIPTION: SEQ ID NO: 231:

TAGGAGTTGG TGTAAAGGAT                                                   20

(2) INFORMATION FOR SEQ ID NO: 232:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 232:

TTTAAAATTA GGAGTTGGTG                                                   20

(2) INFORMATION FOR SEQ ID NO: 233:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 233:

GAAATTATTT AAAATTAGGA                                                   20

(2) INFORMATION FOR SEQ ID NO: 234:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 234:

CAGAGTAGAA ATTATTTAAA                                                   20

(2) INFORMATION FOR SEQ ID NO: 235:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 235:

CTCATTTAAG ACAGAGTAGA                                                   20

(2) INFORMATION FOR SEQ ID NO: 236:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 236:

TACTTCTCAT TTAAGACAGA                                                   20

(2) INFORMATION FOR SEQ ID NO: 237:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 237:

CATATACATA TTTAAGAAAA                                                   20

(2) INFORMATION FOR SEQ ID NO: 238:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 238:

TTAAATGTCA TATACATATT                                                   20

(2) INFORMATION FOR SEQ ID NO: 239:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 239:

TAATAAGTTA CATTTAAATG                                                   20

(2) INFORMATION FOR SEQ ID NO: 240:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 240:

GTAACAGAGC AAGACTCGGT                                                   20

(2) INFORMATION FOR SEQ ID NO: 241:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 241:

CAGCCTGGGT AACAGAGCAA                                                   20

(2) INFORMATION FOR SEQ ID NO: 242:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 242:

CACTCCAGCC TGGGTAACAG                                      20

(2) INFORMATION FOR SEQ ID NO: 243:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 243:

CCCACTGCAC TCCAGCCTGG                                      20

(2) INFORMATION FOR SEQ ID NO: 244:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 244:

GCCAAGATCA CCCACTGCAC                                      20

(2) INFORMATION FOR SEQ ID NO: 245:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 245:

GCAGTGAGCC AAGATCACCC                                      20

(2) INFORMATION FOR SEQ ID NO: 246:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 246:

GAGCTTGCAG TGAGCCAAGA                                      20

(2) INFORMATION FOR SEQ ID NO: 247:

(i) SEQUENCE CHARACTERISTICS:

(A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 247:

GAGGGCAGAG CTTGCAGTGA                                               20

(2) INFORMATION FOR SEQ ID NO: 248:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 248:

CAGGAGAATG GTGCGAACCC                                               20

(2) INFORMATION FOR SEQ ID NO: 249:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 249:

AGGCTGAGGC AGGAGAATGG                                               20

(2) INFORMATION FOR SEQ ID NO: 250:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 250:

ATTGGGAGGC TGAGGCAGGA                                               20

(2) INFORMATION FOR SEQ ID NO: 251:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 251:

CAAGCTAATT GGGAGGCTGA                                               20

(2) INFORMATION FOR SEQ ID NO: 252:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 252:

AGGCCAAGCT AATTGGGAGG                                                    20

(2) INFORMATION FOR SEQ ID NO: 253:

(i) SEQUENCE CHARACTERISTICS:
            (A) LENGTH: 20 base pairs
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 253:

ATGACTGTAG GCCAAGCTAA                                                    20

(2) INFORMATION FOR SEQ ID NO: 254:

(i) SEQUENCE CHARACTERISTICS:
            (A) LENGTH: 20 base pairs
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 254:

CAGATGACTG TAGGCCAAGC                                                    20

(2) INFORMATION FOR SEQ ID NO: 255:

(i) SEQUENCE CHARACTERISTICS:
            (A) LENGTH: 20 base pairs
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 255:

GGTGGCAGAT GACTGTAGGC                                                    20

(2) INFORMATION FOR SEQ ID NO: 256:

(i) SEQUENCE CHARACTERISTICS:
            (A) LENGTH: 20 base pairs
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 256:

AATTAGCCAG GTGTGGTGGC                                                    20

(2) INFORMATION FOR SEQ ID NO: 257:

(i) SEQUENCE CHARACTERISTICS:
            (A) LENGTH: 20 base pairs
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 257:

GTCTCTACTA AAAGTACAAA                                                    20

(2) INFORMATION FOR SEQ ID NO: 258:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 258:

CGGTGAAACC CTGTCTCTAC                                                    20

(2) INFORMATION FOR SEQ ID NO: 259:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 259:

TGGCTAACAC GGTGAAACCC                                                    20

(2) INFORMATION FOR SEQ ID NO: 260:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 260:

AGACCATCCT GGCTAACACG                                                    20

(2) INFORMATION FOR SEQ ID NO: 261:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 261:

GAGATCGAGA CCATCCTGGC                                                    20

(2) INFORMATION FOR SEQ ID NO: 262:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 262:

GAGGTCAGGA GATCGAGACC                                                    20

(2) INFORMATION FOR SEQ ID NO: 263:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 263:

GCGGATCACG AGGTCAGGAG                                      20

(2) INFORMATION FOR SEQ ID NO: 264:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 264:

AGGCCGAGGT GGGCGGATCA                                      20

(2) INFORMATION FOR SEQ ID NO: 265:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 265:

TTTGGGAGGC CGAGGTGGGC                                      20

(2) INFORMATION FOR SEQ ID NO: 266:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 266:

TCCCAGCACT TTGGGAGGCC                                      20

(2) INFORMATION FOR SEQ ID NO: 267:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 267:

CCTGTAATCC CAGCACTTTG                                      20

(2) INFORMATION FOR SEQ ID NO: 268:

(i) SEQUENCE CHARACTERISTICS:
        (A) LENGTH: 20 base pairs

-continued

```
      (B) TYPE: Nucleic Acid
      (C) STRANDEDNESS: Single
      (D) TOPOLOGY: Linear (iv) ANTI-SENSE: Yes (xi) SEQUENCE DESCRIPTION:  SEQ ID NO: 268:

GTGGCTCATG CCTGTAATCC                                               20

(2) INFORMATION FOR SEQ ID NO: 269:

(i) SEQUENCE CHARACTERISTICS:
      (A) LENGTH: 21 base pairs
      (B) TYPE: Nucleic Acid
      (C) STRANDEDNESS: Single
      (D) TOPOLOGY: Linear (iv) ANTI-SENSE: Yes (xi) SEQUENCE DESCRIPTION:  SEQ ID NO: 269:

GGCAAATGTG CAATACCAAC A                                             21

(2) INFORMATION FOR SEQ ID NO: 270:

(i) SEQUENCE CHARACTERISTICS:
      (A) LENGTH: 26 base pairs
      (B) TYPE: Nucleic Acid
      (C) STRANDEDNESS: Single
      (D) TOPOLOGY: Linear (iv) ANTI-SENSE: Yes (xi) SEQUENCE DESCRIPTION:  SEQ ID NO: 270:

TGCACCAACA GACTTTAATA ACTTCA                                        26

(2) INFORMATION FOR SEQ ID NO: 271:

(i) SEQUENCE CHARACTERISTICS:
      (A) LENGTH: 25 base pairs
      (B) TYPE: Nucleic Acid
      (C) STRANDEDNESS: Single
      (D) TOPOLOGY: Linear (iv) ANTI-SENSE: Yes (xi) SEQUENCE DESCRIPTION:  SEQ ID NO: 271:

CCACCTCACA GATTCCAGCT TCGGA                                         25
```